United States Patent [19]

Diana

[11] Patent Number: 5,002,960

[45] Date of Patent: Mar. 26, 1991

[54] N-HALOALKYL-4-(ISOXAZOL-5-YL)AL-KOXY BENZAMIDES

[75] Inventor: Guy D. Diana, Stephentown, N.Y.

[73] Assignee: Sterling Drug, Inc., New York, N.Y.

[21] Appl. No.: 364,928

[22] Filed: Jun. 12, 1989

Related U.S. Application Data

[60] Division of Ser. No. 63,182, Jun. 17, 1987, Pat. No. 4,843,087, which is a continuation-in-part of Ser. No. 751,348, Jul. 2, 1985, abandoned, which is a continuation-in-part of Ser. No. 624,302, Jun. 25, 1984, abandoned, which is a continuation-in-part of Ser. No. 527,583, Aug. 29, 1983, abandoned.

[30] Foreign Application Priority Data

Jun. 24, 1986 [CA] Canada .................................. 512264

[51] Int. Cl.$^5$ .................... A61K 31/42; C07D 261/08; C07D 413/10; C07D 417/10

[52] U.S. Cl. ........................................ 514/378; 544/88; 544/96; 548/206; 548/214; 548/237; 548/247; 548/235; 558/423; 558/425; 560/65; 562/474; 562/840; 564/177

[58] Field of Search .................... 548/247; 514/378

[56] References Cited

U.S. PATENT DOCUMENTS

| | | | |
|---|---|---|---|
| 4,268,678 | 5/1981 | Diana et al. | 548/247 |
| 4,451,476 | 5/1984 | Diana | 548/247 |
| 4,843,087 | 6/1989 | Diana | 514/374 |
| 4,857,539 | 8/1989 | Diana et al. | 548/247 |

FOREIGN PATENT DOCUMENTS 137242 4/1985 European Pat. Off. .

OTHER PUBLICATIONS

Diana et al., Chemical Abstracts, vol. 106, No. 138429 (1987) (Abstract for EP 207454, 1/7/87).

*Primary Examiner*—Mark L. Berch
*Assistant Examiner*—E. Bernhardt
*Attorney, Agent, or Firm*—Thomas L. Johnson; Frederik W. Stonner; Paul E. Dupont

[57] ABSTRACT

Compounds of the formulas:

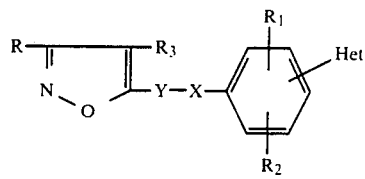

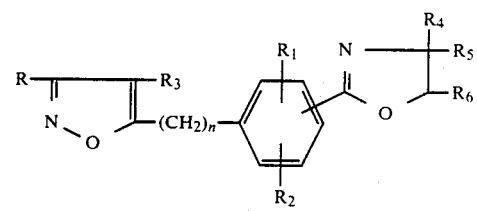

and

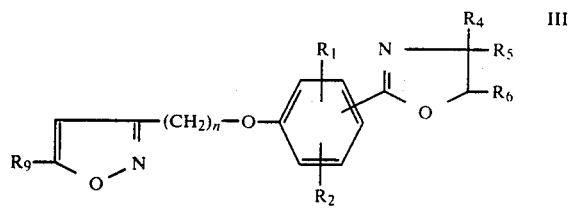

wherein Het is an oxazole or oxazine moiety; X is O, S or SO, n is an integer from 3 to 9, Y is an aliphatic bridge; and the various R groups represent hydrogen or various substituents as described herein, are useful as antiviral agents, especially against picornaviruses. N-(Chloroalkyl)amide intermediates for the compounds of Formula I are also active as antiviral agents. Related compounds outside the scope of the above formulas are also disclosed. Also disclosed are novel intermediates, N-halo-alkyl-4-(isoxazol-5-yl)alkoxybenzamides, also useful as antiviral agents.

7 Claims, No Drawings

N-HALOALKYL-4-(ISOXAZOL-5-YL)ALKOXY BENZAMIDES

This application is a division of application Ser. No. 063,182, filed June 17, 1987, now U.S. Pat. No. 4,843,087, which is a continuation-in-part of application Ser. No. 751,348, filed July 2, 1985, now abandoned; in turn a continuation-in-part of application Ser. No. 624,302, filed June 25, 1984, now abandoned; in turn a continuation-in-part of application Ser. No. 527,583, filed Aug. 29, 1983, now abandoned.

BACKGROUND OF THE INVENTION

1. (a) Field of the Invention

This invention relates to novel heterocyclic substituted-phenyl-aliphatic-lower-alkylisoxazoles and furanes and to compositions and methods for the use thereof as antiviral agents.

2. (b) Information Disclosure Statement

Diana and Carabateas U.S. Pat. No. 4,268,678, issued May 19, 1981, discloses antivirally active compounds having the formula:

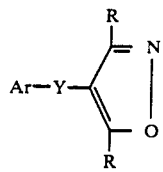

wherein Ar is phenyl substituted by one or two substituents selected from the group consisting of halogen, lower-alkoxy, nitro and hydroxy; Y is $(CH_2)_n$ or $O(CH_2)_n$ where n is an integer from 1 to 8; and R is lower-alkyl.

Sterling Drug Inc. European Patent Application Publ. No. 137,242, published Apr. 17, 1985, discloses antivirally active compounds having the formula

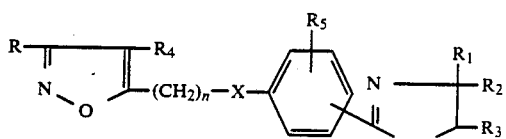

wherein:

$R$, $R_1$, $R_2$, $R_3$ and $R_4$ are each hydrogen or alkyl of 1 to 3 carbon atoms optionally substituted by hydroxy, lower-alkanoyloxy, lower-alkoxy, chloro, or $N=Z$, wherein $N=Z$ is amino, lower-alkanoylamino, lower-alkylamino, di-lower-alkylamino, 1-pyrrolidinyl, 1-piperidinyl or 4-morpholinyl; with the proviso that R is other than hydrogen;

$R_5$ is hydrogen, lower-alkyl, halogen, nitro, lower-alkoxy, lower-alkylthio or trifluoromethyl;

$R_6$ is alkyl of 1 to 3 carbon atoms;

X is O or a single bond; and n is an integer from 3 to 9;

and to pharmaceutically acceptable acid-addition salts thereof.

SUMMARY OF THE INVENTION

In a composition of matter aspect, the invention relates to compounds having the formulas:

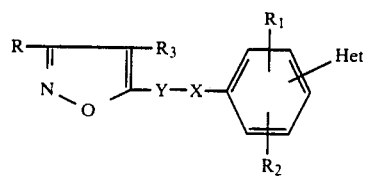

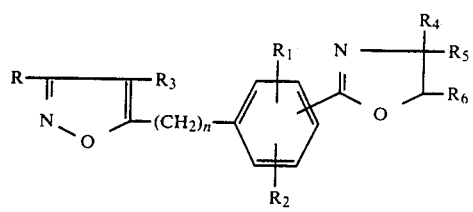

and

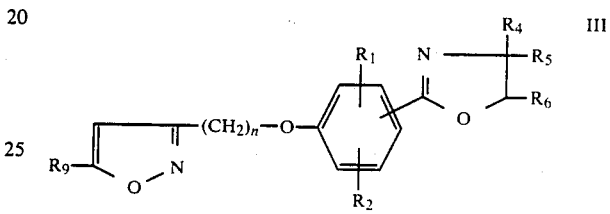

wherein:

Het in Formula I and the oxazolinyl ring in Formulas II and III are in the meta or para position with respect to the phenoxy or phenylalkyl linkage, and Het is selected from the group consisting of:

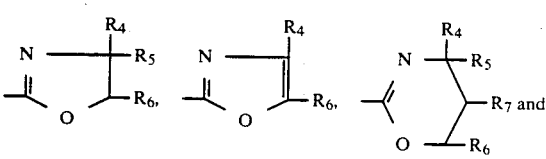

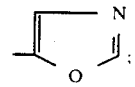

Y is an alkylene bridge of 3 to 9 carbon atoms optionally interrupted by one or two oxygen atoms, by cyclohexyl or by an olefinic linkage;

X is O, S or SO;

n is an integer from 3 to 9;

$R_1$ and $R_2$ are selected from the group consisting of hydrogen, lower-alkyl, lower-alkenyl, halogen, nitro, lower-alkoxy, lower-alkylthio, difluoromethyl, trifluoromethyl, amino, lower-alkanoylamino, di-lower-alkylamino, hydroxy, lower-alkenoyl, lower-alkanoyl, hydroxymethyl and carboxy;

$R$, $R_3$, $R_4$, $R_5$, $R_6$ and $R_7$ are each hydrogen or alkyl of 1 to 3 carbon atoms optionally substituted by a member of the group consisting of hydroxy, lower-alkanoyloxy, lower-alkoxy, halo or $N=Z'$, wherein $N=Z'$ is amino, lower-alkanoylamino, lower-alkylamino, di-lower-alkylamino, 1-pyrrolidyl, 1-piperidinyl or 4-morpholinyl; with the proviso that R is other than hydrogen; and $R_9$ is alkyl of 1 to 3 carbon atoms;

or pharmaceutically acceptable acid-addition salts thereof.

In a further composition of matter aspect, the invention relates to compositions for combating viruses which comprise an antivirally effective amount of a compound of Formulas I, II or III in admixture with a suitable carrier or diluent.

In a further product aspect the invention relates to intermediate compounds having the formula

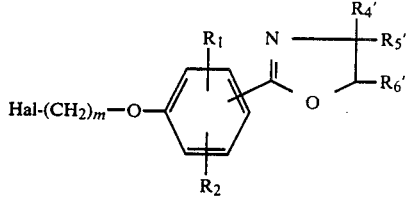

wherein:

R₁ and R₂ are selected from the group consisting of hydrogen, lower-alkyl, lower-alkenyl, halogen, nitro, lower-alkoxy, lower-alkylthio, difluoromethyl, trifluoromethyl, amino, lower-alkanoylamino, di-lower-alkylamino, hydroxy, lower-alkenoyl, lower-alkanoyl, hydroxymethyl and carboxy;

R₄', R₅' and R₆' are each hydrogen, or alkyl or hydroxyalkyl of 1 to 3 carbon atoms;

Hal is chlorine, bromine or iodine;

m is an integer from 2 to 8;

and the oxazoline ring is in the meta or para position with respect to the phenoxy linkage.

In a process aspect, the invention relates to a method for combating viruses which comprises contacting the locus of such viruses with a composition containing an antivirally effective amount of a compound of Formulas I, II or III, including the systemic treatment of viral infections in a mammalian host.

DETAILED DESCRIPTION INCLUSIVE OF PREFERRED EMBODIMENTS

The compounds of Formulas I, II and III are sufficiently basic to form stable acid-addition salts with strong acids, and said salts are within the purview of the invention. The nature of the acid-addition salt is immaterial, provided it is derived from an acid the anion of which is essentially non-toxic to animal organisms. Examples of appropriate acid-addition salts include the hydrochloride, hydrobromide, sulfate, acid sulfate, maleate, citrate, tartrate, methanesulfonate, p-toluenesulfonate, dodecyl sulfate, cyclohexanesulfamate, and the like.

Throughout this specification, when the terms lower-alkyl, lower-alkenyl, lower-alkoxy, lower-alkanoyl, lower-alkanoyloxy, lower-alkylthio, lower-alkenoyl, lower-alkanoylamino, lower-alkylamino, and di-lower-alkylamino are used, they refer to such groups having from one to four carbon atoms. When the term halogen is used to define the substituents R₁ and R₂, any of the four common halogens, fluorine, chlorine, bromine or iodine are contemplated.

The compounds of Formula I wherein X is O are prepared by reacting a compound of the formula

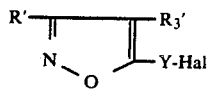

wherein R' and R₃' are each hydrogen, or alkyl or hydroxyalkyl of 1 to 3 carbon atoms, R' being other than hydrogen; Hal is chlorine, bromine or iodine; and Y has the meaning given above, with an alkali metal salt of a compound of the formula

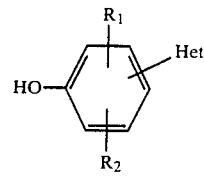

where R₁, R₂ and Het have the meanings given above. The reaction takes place by heating the reactants in an inert solvent in the presence of an alkali metal base, e.g. potassium carbonate at a temperature between about 50° and 150° C.

The intermediates of Formula V are prepared by reacting an alkali metal derivative of an isoxazole of the formula

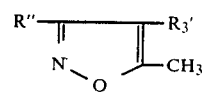

wherein R" is alkyl or hydroxyalkyl of 1 to 3 carbon atoms with a dihalide, Hal-Y'-Hal, where Y' is an alkylene bridge of 2 to 8 carbon atoms optionally interrupted by one or two oxygen atoms or by an olefinic linkage. Said alkali metal derivative is prepared in situ by treating the compound of Formula VII with an organo-alkali metal base under anhydrous conditions. Preferred organo-alkali metal bases are butyllithium and lithium diisopropylamide.

The intermediates of Formula VI are a generically known class of heterocyclic substituted phenols, prepared as described hereinafter in the general description and specific examples.

An alternative approach to the compounds of Formula I where X is O is by the process of reacting a compound of the formula

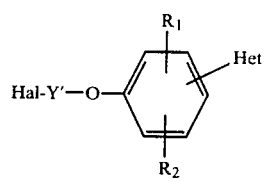

where Hal is chlorine, bromine or iodine; Y' is an alkylene bridge of 2 to 8 carbon atoms optionally interrupted by one or two oxygen atoms or by an olefinic linkage; and R₁, R₂ and Het have the meanings given above, with an alkali metal derivative of a compound of Formula VII above.

A preferred class of compounds within the scope of Formula I are those where X is O and Het is an oxazolinyl group, having the formula

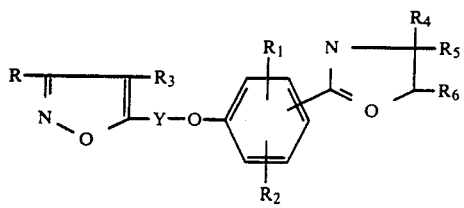

Intermediates for the compounds of Formula IX are conveniently prepared according to the following flow sheet where $R_4'$, $R_5'$ and $R_6'$ are hydrogen or unsubstituted alkyl groups.

alkali metal derivative of an isoxazole of Formula VII to give a compound of Formula IX.

In an alternative approach, the ester X is converted to the amide XV and the latter cyclized to a phenolic dihydro-oxazole (XVI). Etherification with an alkylene dibromide then gives XVII. The ester XVII, upon reaction with an intermediate of Formula V, produces a compound of Formula IX.

In the foregoing flow sheet, if the hydroxyethylamine reactant [$H_2NC(R_4'R_5'CH(R_6'')OH$] is replaced by a homologous hydroxypropylamine reactant of the formula $H_2NC(R_4'R_5')CH(R_7')CH, (R_6')OH$, where $R_4'$, $R_5'$, $R_6'$ and $R_7'$ are hydrogen or unsubstituted alkyl, there is produced a dihydro-oxazine compound analogous to Formula XVI of the formula

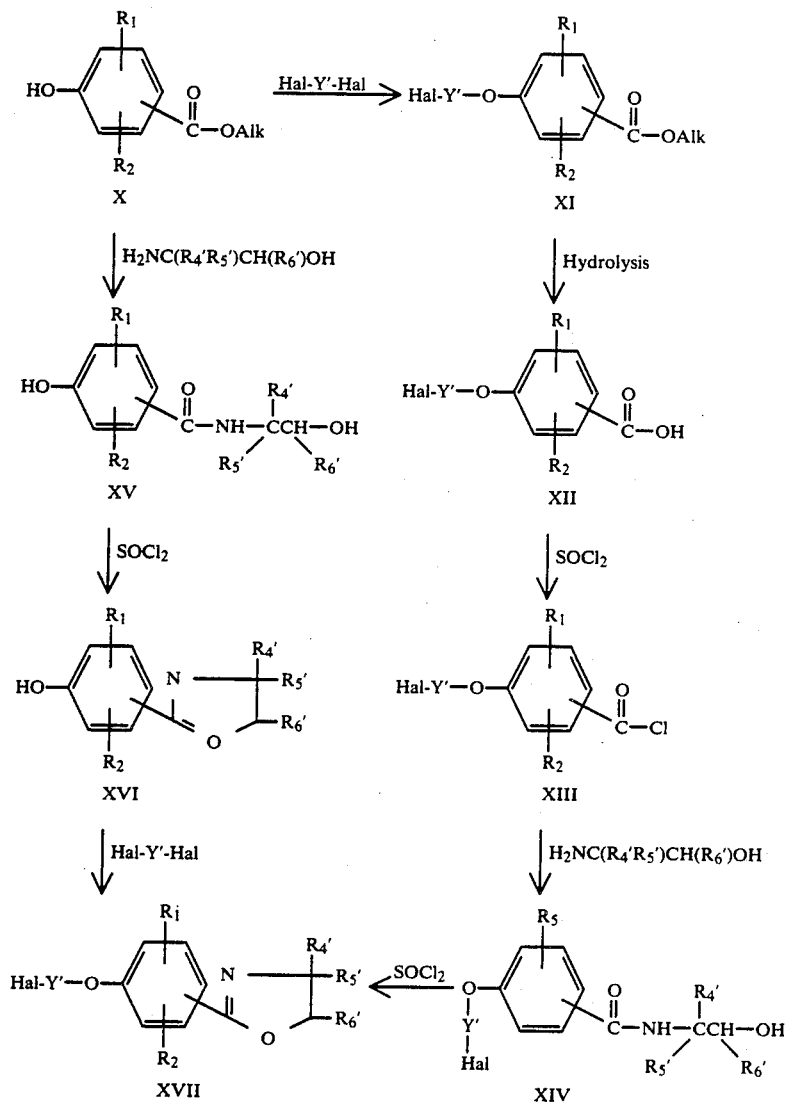

A hydroxybenzoate (X, Alk=lower-alkyl) in the presence of a base reacts with an alkylene dihalide to form a haloalkyl ether (XI). The ester group is then hydrolyzed, preferably with a strong acid, to give the corresponding carboxylic acid (XII). The latter is converted to its acid chloride (XIII) which reacts with hydroxyethylamine or an alkylated derivative thereof to give an amide of the Formula XIV. The amide is then cyclized with thionyl chloride to give the desired intermediate of Formula XVII. The latter reacts with an

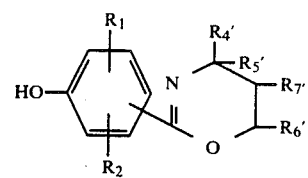

which serves as an intermediate for the compounds of Formula I where Het is

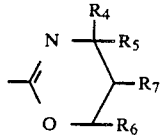

A further alternative process for preparing compounds of Formula IX comprises reacting a compound of the formula

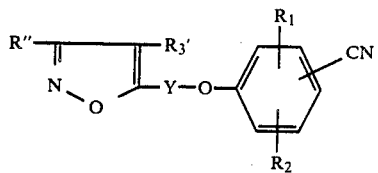

with a lower-alkanol in the presence of a strong acid and heating the resulting imino ester with a compound of the formula

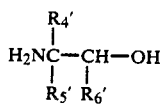

A preferred procedure is to saturate a solution of the nitrile XVIII in a lower-alkanol, preferably methanol or ethanol with gaseous hydrogen chloride at a reduced temperature (0° to −70° C.) and allow the mixture gradually to warm to room temperature until the reaction is complete. The hydrochloride salt of the imino ester is obtained. The latter is then caused to react with a hydroxyalkylamine (XIX) by heating the reactants together at a temperature between about 100° C. and 150° C. to produce a compound of Formula IX.

The intermediate nitriles of Formula XVIII are in turn prepared by reacting an alkali metal derivative of an isoxazole of Formula VII with a halide of the formula

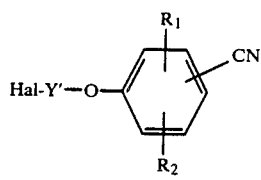

The compounds of Formula XX are obtained by reacting the appropriate cyanophenol with a dihalide Hal-Y'-Hal in the presence of a base. Alternatively, the intermediate nitriles of Formula XVIII are prepared by reacting the appropriate cyanophenol with a 5-haloalkylisoxazole of Formula V.

A preferred species within the scope of Formula IX, having particularly valuable properties as an antiviral agent, is 5-{7-[4-(4,5-dihydro-2-oxazolyl)phenoxy]heptyl}-3-methylisoxazole having the formula

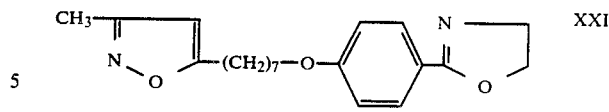

Compound XXI was subjected to the fermentative enzymatic action of a variety of microorganisms. Two microorganisms, *Aspergillus niger* (A₁) and *Trichothecium roseum* (T₁) produced predominantly single oxidation products of the Formulas XXII and XXIII, respectively:

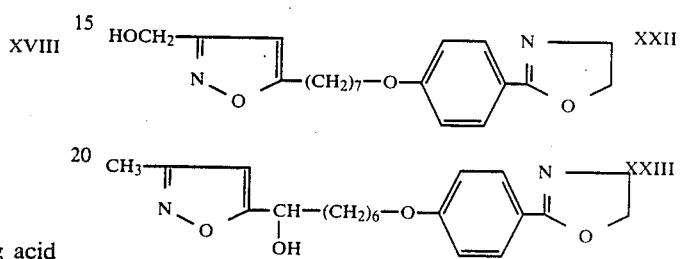

the structures being established by nuclear magnetic resonance data. Compounds XXII and XXIII are also within the purview of the invention.

The compouns of Formula I where Het is a 5-oxazolyl group:

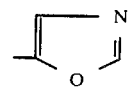

are prepared by reacting a benzaldehyde derivative of the formula:

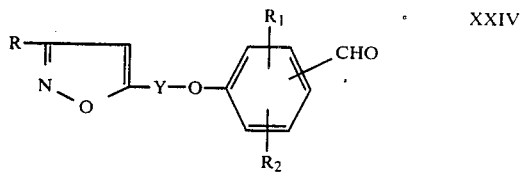

with tosylmethyl isocyanide (4-CH₃C₆H₄SO₂CH₂NC), heated in the presence of potassium carbonate.

The compounds of Formula I where Het is

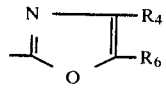

are prepared by a procedure analogous to that described above, namely by reaction of a phenol of formula

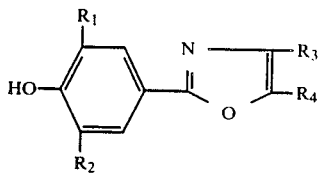

with a compound of Formula V. The intermediates are in turn prepared by reacting an aldehyde of the formula

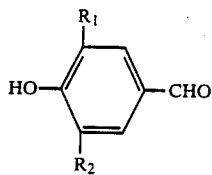

with an oxime of the formula $R_3C(=NOH)—COR_4$ and reducing the resulting oxazole N-oxide with zinc or titanium trichloride.

The compounds of Formula II are prepared from intermediates of the formula

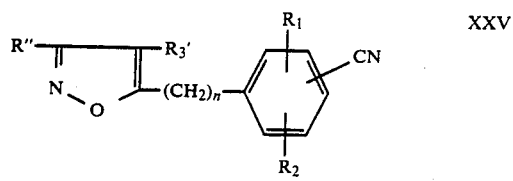

XXV by reaction with a strong acid followed by heating with a hydroxyalkylamine of Formula XIX. This is analogous to the conversion of nitriles of Formula XVIII to compounds of Formula IX.

The intermediates of Formula XXV are prepared by reacting an alkali metal derivative of an isoxazole derivative of Formula VII with a halide of the formula

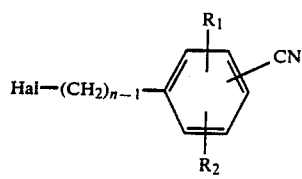

XXVI

The compounds of Formula XXVI are in turn prepared by procedures analogous to those shown in Collins U.S. Pat. No. 4,093,736 (Jun. 6, 1978) starting with the appropriate cyanophenyl compounds. For example, starting with 4-cyanobenzaldehyde and methyl cyclopropyl ketone, and following the reactions of sequence A of said patent, there is obtained 6-(4-cyanophenyl) hexyl bromide.

The compounds of Formula III are prepared in analogous fashion by reacting a compound of the formula

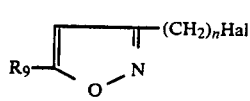

XXVII with a phenol of Formula XVI; or by reacting a compound of Formula XXVII with a cyanophenol and conversion of the cyano group to a 2-oxazolinyl group.

The intermediates of Formula XXVII are in turn prepared by a reaction sequence involving conventional side-chain homologation reactions starting with a 5-$R_9$-isoxazole-3-carboxylic acid. This is illustrated by the procedures described hereafter in Example 7.

The compounds of Formula I, II or III where one or more of R, $R_3$, $R_4$, $R_5$, $R_6$ and $R_7$ are lower-alkyl substituted by lower-alkanoyloxy, lower-alkoxy, chloro or $N=Z$ are prepared from the corresponding compounds of Formula I, II or III where one or more of the recited R groups are hydroxyalkyl.

Esterification of a hydroxyalkyl compound by conventional procedures, as by reaction with a lower-alkanoic acid anhydride or halide gives the corresponding lower-alkanoyloxy derivative. The lower-alkanoyl groups preferably have from one to four carbon atoms.

Etherification of a hydroxyalkyl compound by conventional procedures, as by reaction with a lower-alkyl halide in the presence of a strong base, gives the corresponding lower-alkoxy derivative. The lower-alkoxy groups preferably have from one to four carbon atoms.

A hydroxyalkyl compound can be converted to a chloroalkyl compound by reaction with a reagent such as thionyl chloride or phosphorus trichloride, capable of replacing aliphatic hydroxy groups by chlorine.

The chloroalkyl compounds are in turn convertible to aminoalkyl compounds by reaction with ammonia or an amine, $HN=Z$. Compounds where $HN=Z$ is lower-alkanoylamino are prepared by acylation of the compounds where $HN=Z$ is $NH_2$ with a lower-alkanoyl halide or anhydride, lower-alkanoyl preferably having from 1 to 4 carbon atoms.

The compounds of Formula I wherein X is S are prepared by methods analogous to those used for the corresponding compounds wherein X is O. An alternative process for preparing the sulfur analogs of compounds of Formula IX, involves the reaction of a disulfide of the formula

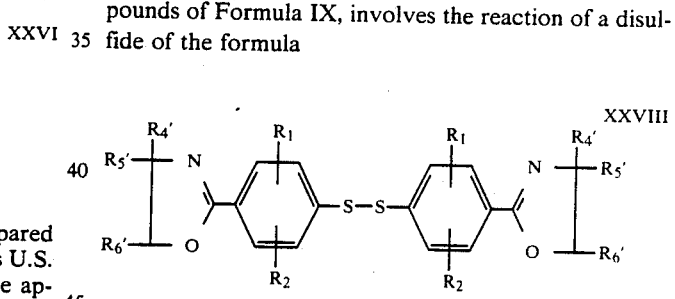

XXVIII with a 5-haloalkylisoxazole of Formula V. The compounds of Formula XXVIII are in turn prepared from the corresponding bis-benzoic acid disulfides of the formula

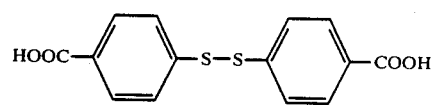

by forming the dihydro-oxazole moieties according to the methods described above.

The compounds of Formula I where X is SO are prepared by oxidation of the compounds where X is S by conventional oxidation procedures, for example with hydrogen peroxide or organic peracids.

Further aspects of the invention which are outside the scope of Formula I relate to the following structures:

Compounds of the formula:

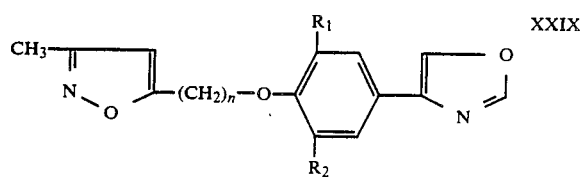   XXIX wherein n is an integer from 3 to 8 and $R_1$ and $R_2$ are selected from methyl and chloro. These compounds are prepared from the appropriate 5-(haloalkyl)-3-methylisoxazole and 4-(4-oxazolyl)phenol.

Compounds of the formula:

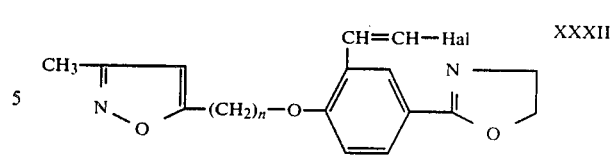   XXXII wherein n is an integer from 3 to 8 and Hal is halogen selected from chlorine and bromine. These compounds are prepared by reacting the corresponding aldehydes within the scope of Formula I ($R_1$=CHO) with triphenylphosphine halide.

Compounds of the formula:

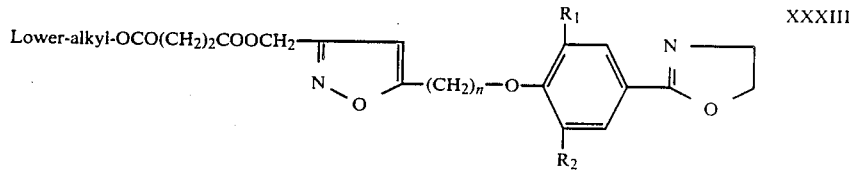   XXXIII

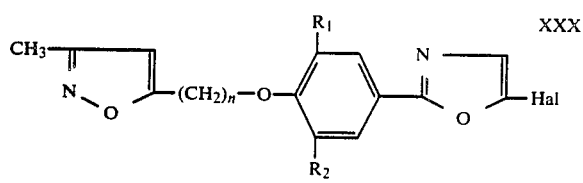   XXX wherein n is an integer from 3 to 8, $R_1$ and $R_2$ are selected from methyl and chloro, and lower-alkyl has from 1 to 6 carbon atoms. These compounds are prepared by esterification of the corresponding compounds of Formula I where R is hydroxymethyl with a mono-lower-alkyl succinate.

Compounds of the formula:

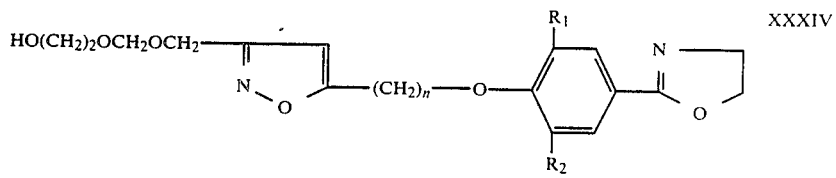   XXXIV wherein n is an integer from 3 to 8, $R_1$ and $R_2$ are selected from methyl and chloro, and Hal is halogen selected from chlorine and bromine. These compounds are prepared from the appropriate 5-(haloalkyl)-3-methylisoxazole and 4-(5-halo-2-oxazolyl)phenol. The latter can be prepared by reaction of a 4-(2-oxazolyl)-phenol and thionyl halide.

Compounds of the formula:

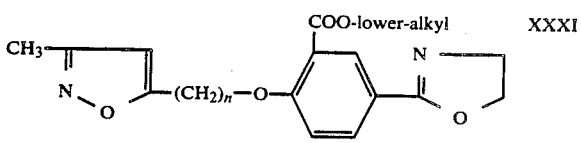   XXXI wherein n is an integer from 3 to 8 and lower-alkyl has from 1 to 6 carbon atoms. These compounds are prepared by esterification of the corresponding carboxylic acids within the scope of Formula I ($R_1$=COOH).

Compounds of the formula:

wherein n is an integer from 3 to 8 and $R_1$ and $R_2$ are selected from methyl and chloro. These compounds are prepared by etherification of the corresponding compounds of Formula I where R is hydroxyethyl with 2-acetoxyethoxymethyl bromide followed by hydrolysis of the acetyl group.

Compounds of the formula:

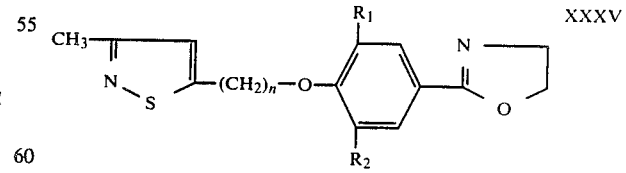   XXXV wherein n is an integer from 3 to 8 and $R_1$ and $R_2$ are selected from methyl and chloro. These compounds are prepared by reacting the appropriate 4-(4,5-dihydro-2-oxazolyl)phenol and 5-(haloalkyl)-3-methylisothiazole. The latter can be prepared by alkylation of 3-methylisothiazole with a bromoalkyl chloride.

Compounds of the formula:

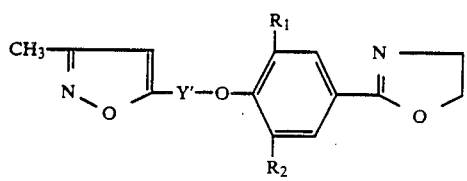

XXXVI where Y' is an alkylene bridge of 3-8 carbon atoms interrupted by an acetylenic linkage, and $R_1$ and $R_2$ are selected from methyl and chloro. These compounds are prepared by reacting the appropriate 4-(4,5-dihydro-2-oxazolyl)phenol and 5-(halo-Y')-3-methylisoxazole. The latter can be prepared by alkylation of 3-methylisoxazole with an α,ω-dihaloalkyne.

Compounds of the formula:

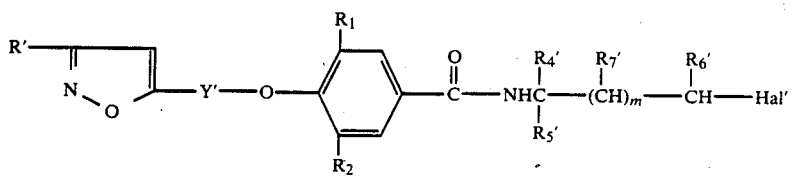

XXXVII wherein:
Y is an alkylene bridge of 3-9 carbon atoms;
m is 0 or 1;
$R_1'$ and $R_2'$ are selected from the group consisting hydrogen, lower-alkyl, halogen, nitro, lower-alkoxy, lower-alkoxycarbonyl and trifluoromethyl;
R', $R_4'$, $R_5'$, $R_6'$ and $R_7'$ are hydrogen or alkyl of 1-5 carbon atoms; R' being other than hydrogen; and
Hal is chlorine or bromine.

The compounds of Formula XXXVII are prepared according to the following flow sheet:

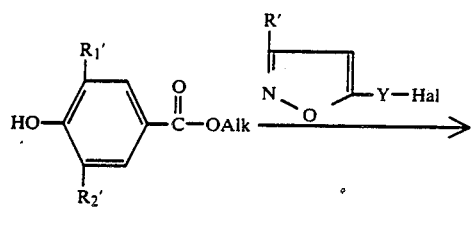

XXXVIII

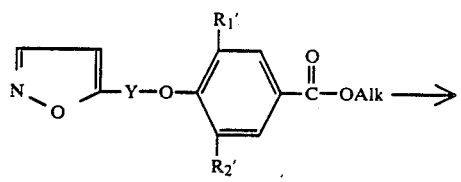

XXXIX

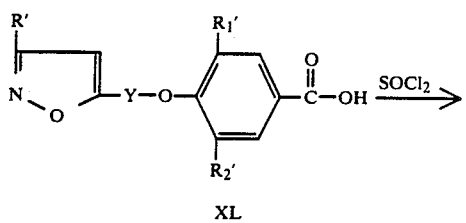

XL

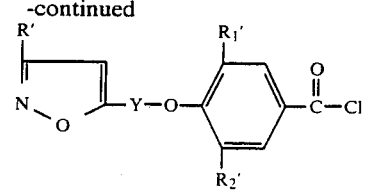

XLI

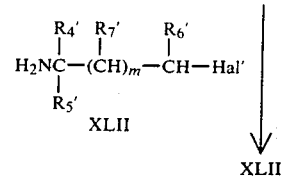

XLII

↓

XLII

The hydroxybenzoate (XXXVIII) is caused to react with a haloalkylisoxazole to give the ester (XXXIX) which is hydrolyzed to the corresponding acid (XL). The latter is then converted to its acid chloride (XLI) which is reacted with a haloalkylamine (XLII) to give a haloalkylamide of Formula XXXVII. Variations in the sequence of steps XXXVII→XL can be employed using compounds with nitrile or formyl groups in place of the ester moiety, with eventual conversion to the free carboxyl group.

The haloalkylamides (XXXVII) per se have antirhinovirus activity and are also useful as intermediates in the preparation of compounds of Formula I by cyclization in the presence of an acid-acceptor. The cyclization takes place in an inert solvent at a temperature between 50° C. and 150° C., conveniently at the reflux temperature of the solvent mixture. The acid-acceptor can be any basic substance capable of absorbing the hydrogen halide produced in the reaction while otherwise inert in the reaction. Such acid-acceptors may be tertiary-amines or inorganic bases such as potassium carbonate. A preferred acid-acceptor is 1,8-diazabicyclo[5.4.0]undec-7-ene.

The structures of the compounds of the invention were established by the modes of synthesis, by elementary analysis, and by infrared and nuclear magnetic resonance spectra.

The following examples will further illustrate the invention.

EXAMPLE 1

(a) 4-(6-Bromohexyloxy)benzonitrile [XX; Hal=Br, Y'=$(CH_2)_6$, $R_1$ and $R_2$=H, CN at 4-position]

A mixture of 23.8 g (0.2 mole) of 4-cyanophenol, 55.3 g (0.4 mole) of milled potassium carbonate, 97.6 g of 1,6-dibromohexane, 0.5 g of sodium iodide and 750 ml of acetone was stirred at reflux for two days. The solid was filtered off and the filtrate concentrated in vacuo. The residue was partitioned between water and methylene dichloride, and the organic phase was dried and concentrated. The residue was distilled to give 40 g of 4-(6-bromohexyloxy)benzonitrile, b.p. 150°-160° C. (0.05 mm).

(b) 5-[7-(4-Cyanophenoxy)heptyl]-3-methylisoxazole [XVIII; R″=CH$_3$, R$_1$, R$_2$ and R$_3$′=H, Y=(CH$_2$)$_7$, CN at 4-position]

To a suspension of 301 mg of lithium wire (¼ inch portions) in 10 ml of tetrahydrofuran under nitrogen was added 6.72 ml of diisopropylamine and 3.44 ml of styrene while maintaining the temperature at 25° C. The mixture was stirred until all the lithium had dissolved (about four hours) and then cooled to −55° C. 3,5-Dimethylisoxazole (4.3 g) in 10 ml of tetrahydrofuran was then added dropwise and the mixture stirred for an hour at −55° C. 4-(6-Bromohexyloxy)benzonitrile (12 g) in 10 ml of tetrahydrofuran was then added dropwise over a period of one hour, and the mixture was allowed to warm to room temperature and stirred for three days. The solvent was removed in vacuo, the residue treated with 5% ammonium chloride solution and extracted with ether. The ether extracts were dried and concentrated, and the residue subjected to high pressure liquid chromatography with ether-hexane (1:1) mixture to give 3.9 g of 5-[7-(4-cyanophenoxy)heptyl]-3-methylisoxazole, used directly in the next reaction.

(c) 5-{7-[4-(4,5-Dihydro-2-oxazolyl)phenoxy]heptyl}-3-methylisoxazole [XXI]

A solution of 3.9 g of 5-[7-(4-cyanophenoxy)heptyl]-3-methylisoxazole in 10 ml of ethanol and 20 ml of ether was treated with gaseous hydrogen chloride at −70° C. until the solution was saturated. The solution was then allowed to warm to room temperature, allowed to stand for about 20 hours and the solvent removed in vacuo. The residue was crystallized from ethanol-ether to give 4.2 g of the corresponding ethyl imino-ester hydrochloride. The latter was mixed with 0.84 g of 2-hydroxyethylamine and heated at 120° C. for about three hours. The reaction mixture was cooled and crystallized from isopropyl acetate. A recrystallization from the same solid afforded 2.7 g of 5-{7-[4-(4,5-dihydro-2-oxazolyl)phenoxy]heptyl}-3-methylisoxazole, colorless solid, m.p. 89°-90° C.

A sample of the compound was treated with methanesulfonic acid in ethyl acetate solution to give the monomethanesulfonate salt, m.p. 134°-135° C.

A sample of the compound was treated with sodium lauryl sulfate in aqueous methanol to give the monododecyl sulfate salt, m.p. 142°-144° C. when recrystallized from acetone.

EXAMPLE 2

(a) 4-(4-Bromobutyloxy)benzonitrile [XX; Hal=Br, Y′=(CH$_2$)$_4$, R$_1$ and R$_2$=H, CN at 4-position] was prepared from 4-cyanophenol and 1,4-dibromobutane according to the procedure of Example 1, part (a), and was obtained in 52% yield; b.p. 155° C. (0.05 mm), m.p. 48°-50° C.

(b) 5-[5-(4-Cyanophenoxy)pentyl]-3-methylisoxazole [XVIII; R″=CH$_3$, R$_1$, R$_2$ and R$_3$′=H, Y=(CH$_2$)$_5$, CN at 4-position]

To a solution of 5.86 g of 3,5-dimethylisoxazole in 120 ml of dry tetrahydrofuran at −70° C. under nitrogen was added during 14 minutes 36 ml of n-butyllithium (1.7M in hexane). The mixture was stirred at −70° C. for 30 minutes, and then 15.2 g of 4-(4-bromobutyloxy)-benzonitrile in 40 ml of tetrahydrofuran was added over a 15 minute period. The reaction mixture was stirred for 1.5 hours at −70° C. and then allowed to warm to room temperature and stirred for 2.5 hours longer. Evaporation of the solvent gave a residue which was treated with 300 ml of ethyl acetate, 150 ml of concentrated sodium chloride solution and 12 ml of hydrochloric acid. The material which was soluble in ethyl acetate was isolated, combined with material from another run of the same scale and subjected to high pressure liquid chromatography with ether-hexane (1:1) to give 20 g of 5-[5-(4-cyanophenoxy)pentyl]-3-methylisoxazole as a colorless solid, m.p. 57° C.

(c) 5-{5-[4-(4,5-Dihydro-2-oxazolyl)phenoxy]pentyl}-3-methylisoxazole [IX; R=CH$_3$, R$_1$, R$_2$, R$_3$, R$_4$, R$_5$ and R$_6$=H, Y=(CH$_2$)$_5$, oxazole at 4-position] was prepared by conversion of 5-[5-(4-cyanophenoxy)pentyl]-3-methylisoxazole to the corresponding ethyl imino-ester hydrochloride (m.p. 120°-121° C.) and reaction of the latter with 2-hydroxyethylamine in accordance with the procedure of Example 1, part (c). The product was obtained in 68% yield as a colorless solid, m.p. 87°-88° C.; monomethanesulfonate salt, m.p. 124°-125° C. The free base was obtained as a colorless solid, m.p. 102°-103.5° C.

EXAMPLE 3

5-{7-[4-(4,5-Dihydro-4-methyl-2-oxazolyl)phenoxy]-heptyl}-3-methylisoxazole [IX; R and R$_4$=CH$_3$, R$_1$, R$_2$, R$_3$, R$_5$ and R$_6$=H, Y=(CH$_2$)$_7$, oxazole at 4-position] was prepared from 5-[7-(4-cyanophenoxy)heptyl]-3-methylisoxazole following the procedure of Example 1, part (c) but substituting racemic 2-amino-1-propanol for the 2-hydroxyethylamine used therein. The product was obtained in about 65% yield as a colorless solid, m.p. 72° C. when recrystallized from isopropyl acetate.

EXAMPLE 4

(−)-5-{7-[4-(4,5-Dihydro-4-methyl-2-oxazolyl)-phenoxy]heptyl}-3-methylisoxazole [IX; R and R$_4$=CH$_3$, R$_1$, R$_2$, R$_3$, R$_5$ and R$_6$=H, Y=(CH$_2$)$_7$, oxazole at 4-position, levoisomer] was prepared from 5-[7-(4-cyanophenoxy)heptyl]-3-methylisoxazole following the procedure of Example 1, part (c), but substituting methanol for ethanol in the iminoester formation, and using L-2-amino-1-propanol in place of 2-hydroxyethylamine. Milder conditions (reflux in triethylamine) were used in the last step. The product was obtained in about 50% yield as a colorless solid, m.p. 71° C., $[\alpha]_D^{25}$ (1% in ethanol)=−31.7°.

The corresponding dextro-isomer, m.p. 71°-72° C., $[\alpha]_D^{25}$ (1% in ethanol)=+32.9° was obtained when D-2-amino-1-propanol was used in the reaction.

EXAMPLE 5

5-{7-[4-(4,5-Dihydro-4,4-dimethyl-2-oxazolyl)-phenoxy]heptyl}-3-methylisoxazole [IX; R, R$_4$, R$_5$=CH$_3$, R$_1$, R$_2$, R$_3$ and R$_6$=H, Y=(CH$_2$)$_7$, oxazole at 4-position] was prepared from 5-[7-(4-cyanophenoxy)-heptyl]-3-methylisoxazole following the procedure of Example 1, part (c) but substituting 2-amino-2-methyl-1-propanol for the 2-hydroxyethylamine used therein. The product was obtained in about 65% yield as a colorless solid, m.p. 45°-46° C. when recrystallized from n-hexane.

It is further contemplated that by replacing the 2-hydroxyethylamine in Example 1, part (c) by a molar equivalent amount of tris(hydroxymethyl)aminomethane [tromethamine, (HOCH$_2$)$_3$CNH$_2$] there can be obtained 5-{7-[4-(4,5-dihydro-4,4-bishydroxymethyl-2-oxazolyl)phenoxy]heptyl}-3-methylisoxazole [IX; R=CH$_3$, R$_4$ and R$_5$=CH$_2$OH, R$_1$, R$_2$, R$_3$ and R$_6$=H, Y=(CH$_2$)$_7$]

EXAMPLE 6

(a) 4-Cyanophenylvinyl cyclopropyl ketone

To a solution of 39.3 g of 4-cyanobenzaldehyde and 25.2 g of cyclopropyl methyl ketone in 60 ml of absolute ethanol was added 21 ml of 20% sodium hydroxide solution over a 25 minute period. The mixture was stirred for one hour at room temperature, cooled to 1° C. and 40 ml of cold water added. The solid material was collected by filtration and triturated with 450 ml of methylene dichloride and 150 ml of water at room temperature. The aqueous phase was extracted with methylene dichloride and the combined organic layers dried and concentrated in vacuo. The residue was recrystallized from absolute ethanol to give 45.0 g of 4-cyanophenylvinyl cyclopropyl ketone, m.p. 104° C.

(b) 4-Cyanophenylethyl cyclopropyl ketone

A solution of 11.83 g of 4-cyanophenylvinyl cyclopropyl ketone in 200 ml of absolute ethanol containing 0.3 g of 10% palladium-on-carbon catalyst was hydrogenated at an initial pressure of 45 pounds per sq. in. for one hour. The catalyst was filtered off, and the product isolated from the filtrate and recrystallized from methanol to give 8.9 g of 4-cyanophenylethyl cyclopropyl ketone, m.p. 76° C.

(c) 4-Cyanophenylethyl cyclopropyl carbinol

To a solution of 30.9 g of 4-cyanophenylethyl cyclopropyl ketone in 90 ml of absolute ethanol was added 1.48 g of sodium borohydride, and the mixture was stirred at room temperature for three hours. The product isolated from the reaction still contained unreacted starting material, so the material was redissolved in 90 ml of ethanol and treated with 0.7 g additional sodium borohydride for three hours. The product obtained by evaporation of the solvent, trituration of the residue with methylene dichloride and water, and isolation of the product from the organic phase, gave 31.0 g of 4-cyanophenylethyl cyclopropyl carbinol as an oil which crystallized to a colorless solid, m.p. 70°–71° C.

(d) 4-(6-Bromohex-3-enyl)benzonitrile

To a solution of 9.8 g of 4-cyanophenylethyl cyclopropyl carbinol in 140 ml of ether was added 4.24 g of lithium bromide and 3 ml of 2,4,6-collidine. The mixture was cooled to −60° C. and 9.8 g of phosphorus tribromide was added over a five minute period. The reaction mixture was allowed to warm to 0° C., kept at that temperature for two hours and then allowed to warm to 18° C. Collidine (18 ml) was added, and after 15 minutes of stirring, the mixture was poured into 200 ml of water and 100 ml of ether. The ether extracts were washed with dilute aqueous sulfuric acid and water, dried over anhydrous magnesium sulfate and concentrated to a volume of 150 ml. Zinc bromide (11.6 g) was then added with cooling, and the mixture was stirred at room temperature for 29 hours. The ether solution was washed with water, dried and concentrated to give 12.5 g of 4-(6-bromohex-3-enyl)benzonitrile as a yellow oil.

(e) 4-(6-Bromohexyl)benzonitrile

A solution of 10.5 g of 4-(6-bromohex-3-enyl)benzonitrile in 200 ml of absolute ethanol was hydrogenated in the presence of 0.25 g of platinum oxide catalyst. Isolation of the product afforded 10.4 g of 4-(6-bromohexyl)benzonitrile as a yellow oil which was distilled at 168°–170° C. (0.01 mm) to produce the compound as a colorless oil which solidified upon cooling.

(f) 5-[7-(4-Cyanophenyl)heptyl]-3-methylisoxazole [XXV; R″=CH$_3$, R$_1$, R$_2$ and R$_3'$=H, CN at 4-position] was prepared from 4-(6-bromohexyl)benzonitrile and the lithium derivative of 3,5-dimethylisoxazole according to the procedure of Example 2(b). The crude product was chromatographed on magnesium silicate (Florisil) using the solvent series hexane:ether:methanol for elution. Ether-hexane 30:70 and 40:60 brought out the desired 5-[7-(4-cyanohexyl)heptyl]-3-methylisoxazole, obtained as a colorless solid, m.p. 61° C., when recrystallized from ether.

(g) 5-{7-[4-(4,5-Dihydro-2-oxazolyl)phenyl]heptyl}-3-methylisoxazole [II; R=CH$_3$, R$_1$, R$_2$, R$_3$, R$_4$ and R$_5$=H, n=7, CN at 4-position]

A suspension of 5.08 g of 5-[7-(4-cyanophenyl)heptyl]-3-methylisoxazole in 35 ml of dry methanol at −5°–0° C. was saturated with hydrogen chloride gas (55 minutes). The mixture was kept cold for two days, then concentrated in vacuo at 25°–30° C. and the residue stirred with 70 ml ether and cooled. The product was collected and dried to give 6.1 g of the methyl imino-ester hydrochloride, m.p. 116° C. (decompn.).

A mixture of 3.5 g of the imino-ester hydrochloride, 1 ml of triethylamine, 0.67 g of 2-aminoethanol and 15 ml of ethylene dichloride was stirred at room temperature for two hours. Additional triethylamine (1 ml) was then added and the mixture heated at reflux for one hour. The reaction mixture was cooled, filtered, diluted with 50 ml of methylene dichloride and washed with water. The water layer was back-washed with methylene chloride, and the combined organic layers were dried over anhydrous magnesium sulfate and concentrated to dryness. There was thus obtained 2.8 g of 5-{7-[4-(4,5-dihydro-2-oxazolyl)phenyl]heptyl}-3-methylisoxazole, colorless solid, m.p. 66°–67° C. Recrystallization from hexane caused no change in melting point.

EXAMPLE 7

(a) 3-Hydroxymethyl-5-methylisoxazole was prepared from 93.4 g of methyl 5-methylisoxazole-3-carboxylate and 62.5 g of sodium borohydride in 1200 ml of t-butyl alcohol and 600 ml of methanol. Isolation of the product and distillation gave 59.2 g of 3-hydroxymethyl-5-methylisoxazole, b.p. 68°–70° C. (0.05 mm).

(b) 3-Chloromethyl-5-methylisoxazole

To a solution of 119.6 g of 3-hydroxymethyl-5-methylisoxazole in 600 ml of ether was slowly added 155 ml of thionyl chloride in 200 ml of ether over a five hour period. The solution was concentrated to an oily residue which was distilled to give 121.2 g of 3-chloromethyl-5-methylisoxazole, b.p. 70°–71° C. (11 mm).

(c) 5-Methyl-3-isoxazolepropanoic acid

To a stirred suspension of 78.5 g of sodium hydride in 1 liter of tetrahydrofuran under nitrogen was added in portions 261 g of diethyl malonate. When evolution of hydrogen had ceased, 108 g of 3-chloromethyl-5-methylisoxazole was added and the reaction mixture was heated at reflux for four hours. A portion of the tetrahydrofuran (800 ml) was distilled off and 1 liter of 5% sodium hydroxide solution was added to the remaining mixture which was then heated at reflux for three hours and allowed to stand at room temperature for three days. The reaction mixture was filtered and the filtrate extracted with hexane. The aqueous layer was acidified with concentrated hydrochloric acid and extracted repeatedly with ethyl acetate. The ethyl acetate was removed in vacuo, 100 ml of pyridine added to the residue, and the mixture heated at reflux for three hours until evolution of carbon dioxide ceased. The mixture was concentrated in vacuo and the residue acidified with 6N hydrochloric acid and cooled. The solid which separated was collected and dissolved in methylene dichloride. The layers were separated and the methylene dichloride layer concentrated in vacuo. The residual solid was slurried with isopropyl acetate-hexane to give 75.4 g of 5-methyl-3-isoxazolepropanoic acid, m.p. 82°–84° C.

(d) Methyl 5-methyl-3-isoxazolepropanoate

A mixture of 75.4 g of 5-methyl-3-isoxazolepropanoic acid, 150 ml of boron trifluoride etherate and 400 ml of methanol was heated at reflux for eight hours. The reaction mixture was concentrated in vacuo, made basic with sodium bicarbonate solution and extracted with methylene dichloride. The extracts were concentrated in vacuo and the residue distilled at 90°–100° C. (0.05 mm) to give 73 g of methyl 5-methyl-3-isoxazolepropanoate which crystallized to a solid, m.p. 54°–55° C.

(e) 5-Methyl-3-(3-hydroxypropyl)isoxazole

To a suspension of 7.6 g of lithium aluminum hydride in 250 ml of tetrahydrofuran was added a solution of 64.9 g of methyl 5-methyl-3-isoxazolepropanoate in 100 ml of tetrahydrofuran. The reaction mixture was stirred at reflux for three hours, then cooled and 15.2 ml of water in 30 ml of tetrahydrofuran added. The mixture was filtered and the filtrate concentrated in vacuo. The residue was distilled to give 44.1 g of 5-methyl-3-(3-hydroxypropyl)isoxazole, b.p. 84°–85° C. (0.1 mm).

(f) 5-Methyl-3-(3-bromopropyl)isoxazole

Bromine (33.8 g) was added to a suspension of 55.5 g of triphenylphosphine in 400 ml of acetonitrile. The mixture was stirred for 30 minutes and concentrated in vacuo to remove the solvent. To the residue was added 200 ml of dimethylformamide, and with stirring 29.8 g of 5-methyl-3-(3-hydroxypropyl)isoxazole was added. An exothermic reaction ensued and the solid materials dissolved to form an orange solution which was poured into water and extracted with methylene dichloride. The methylene dichloride extracts were concentrated and the residue distilled to give 34.1 g of 5-methyl-3-(3-bromopropyl)isoxazole, b.p. 115°–125° C. (0.05 mm).

(g) 3-(4-Carboxybutyl)-5-methylisoxazole was prepared from 5-methyl-3-(3-bromopropyl)isoxazole and diethyl malonate according to the procedure of part (c) above, and was obtained in 56% yield as a colorless solid, m.p. 58°–60° C. when recrystallized from carbon tetrachloride.

(h) 3-(5-Hydroxypentyl)-5-methylisoxazole was prepared by reduction of 3-(4-carboxybutyl)-3-methylisoxazole with lithium aluminum hydride according to the procedure of part (e) above, and was obtained in 84% yield as an oil, b.p. 115°–125° C. (0.1 mm).

(i) 3-(5-Bromopentyl)-5-methylisoxazole [XXVII; $R_9=CH_3$, Hal=Br] was prepared by reacting 3-(5-hydroxypentyl)-5-methylisoxazole with bromine and triphenylphosphine according to the procedure of part (f) above, and was obtained in 77% yield as an oil, b.p. 140°–150° C. (0.05 mm).

(j) 3-[5-(4-Cyanophenoxy)pentyl]-5-methylisoxazole

A mixture of 5.1 g of 4-cyanophenol, 10 g of 3-(5-bromopentyl)-5-methylisoxazole, 8 g of potassium carbonate, 1 g of potassium iodide and 75 ml of acetonitrile was heated at reflux for 24 hours. The product was isolated and distilled, first at 115°–200° C. (0.1 mm) and then at 160°–190° C. (0.05 mm) to yield a yellow oil which crystallized upon cooling. Recrystallization from hexane-ether afforded 6.2 g of 3-[5-(4-cyanophenoxy)-pentyl]-5-methylisoxazole, m.p. 61°–62° C.

(k) 3-{5-[4-(4,5-Dihydro-2-oxazolyl)phenoxy]pentyl}-5-methylisoxazole [III; $R_1$, $R_2$, $R_4$, $R_5$ and $R_6=H$, $R_9=CH_3$, n=5, oxazole at 4-position]

A solution of 6.2 g of 3-[5-(4-cyanophenoxy)pentyl]-5-methylisoxazole in 15 ml of absolute ethanol and 30 ml of ether was cooled to −60° C. and saturated with hydrogen chloride gas over a 45 minute period. The reaction mixture was warmed to room temperature, allowed to stand for three days and then concentrated in vacuo to a solid residue. The latter was recrystallized from ethanol by addition of ether to give 9.6 g of the ethyl imino-ester hydrochloride. The latter was dissolved in 25 ml of chloroform, 3.5 ml of triethylamine was added, and the mixture stirred for one hour. The solution was washed with water, dried over magnesium sulfate and concentrated in vacuo. To the residual oil was added 1.4 g of 2-hydroxyethylamine and the mixture was heated at 115°–120° C. for 1.5 hours. The reaction mixture was cooled and the solid product recrystallized three times from isopropyl acetate to give 4.4 g of 3-{5-[4-(4,5-dihydro-2-oxazolyl)phenoxy]pentyl}-5-methylisoxazole, m.p. 91°–92° C.

EXAMPLE 8

(a) Ethyl 4-(6-bromohexyloxy)benzoate [XI; Alk=$C_2H_5$, $R_1$ and $R_2=H$, $Y'=(CH_2)_6$, Hal=Br]

To a solution of 232 g of ethyl 4-hydroxybenzoate [XII; Alk=$C_2H_5$] in 1.2 liters of dimethylsulfoxide was added 100 g of potassium hydroxide. The mixture was stirred for five minutes, 678 g of 1,6-dibromohexane was then added, and the mixture stirred for four hours during which an exothermic reaction occurred (max. temp. 46° C.). The reaction mixture was added to 1500 ml of water and extracted three times with 800 ml of cyclohexane. The cyclohexane layer was washed with 800 ml of water, 200 ml 2N potassium hydroxide and 800 ml concentrated sodium chloride solution, then filtered and concentrated in vacuo. The residue was triturated with ether to give 328.1 g of ethyl 4-(6-bromohexyloxy)benzoate.

(b) 4-(6-Bromohexyloxy)benzoic acid [XII; $R_1$ and $R_2=H$, $Y'=(CH_2)_6$, Hal=Br]

Concentrated sulfuric acid (1036 ml) was added gradually to 338 ml of water, followed by 622 g of ethyl 4-(6-bromohexyloxy)benzoate. The mixture was heated at 100°–110° C. for 35 minutes and then poured onto 2.5 kg ice with stirring. The mixture was treated with 2520 ml of ammonium hydroxide to bring the pH to 6.0. The product was collected by filtration, washed with water and hexane, and dried in an oven to give 452 g of 4-(6-bromohexyloxy)benzoic acid.

(c) 4-(6-Bromohexyloxy)benzoyl chloride [XIII; $R_1$ and $R_2=H$, $Y=(CH_2)_6$, Hal=Br]

A mixture of 452 g of 4-(6-bromohexyloxy)benzoic acid and 1000 g of thionyl chloride was stirred at room temperature for about 20 hours. The reaction mixture was concentrated in vacuo and residual thionyl chloride removed by repeated addition of toluene and concentration in vacuo. The oily product comprising 4-(6-bromohexyloxy)benzoyl chloride (450 ml) was used directly in the next reaction.

(d) 4-(6-Bromohexyloxy)-N-(2-hydroxyethyl)benzamide [XIV; $R_1$, $R_2$, $R_4'$, $R_5'$ and $R_6'$=H, Y=$(CH_2)_6$, Hal=Br]

To a stirred solution of 300 ml of 2-hydroxyethylamine in 1.2 liter of dimethylformamide at 0° C. was added dropwise 450 ml of 4-(6-bromohexyloxy)benzoyl chloride in 50 ml of toluene over a 30 minute period. After an additional 30 minutes of stirring, 48% hydrobromic acid (about 200 ml) was added until the pH reached 5-5.5, and the mixture was diluted with 1200 ml of water and extracted with isopropyl acetate (total of 2500 ml). The extracts were washed with water and saturated sodium chloride solution, filtered, and concentrated to a volume of about 1 liter. The mixture was cooled and the solid which separated was collected by filtration and dried at 40° C. to give 332.7 g of 4-(6-bromohexyloxy)-N-(2-hydroxyethyl)benzamide.

(e) 2-[4-(6-Bromohexyloxy)phenyl]-4,5-dihydro-oxazole [XVII; Hal=Br, $R_1$, $R_2$, $R_4'$, $R_5'$ and $R_6'$=H, Y=$(CH_2)_6$, oxazole at 4-position]

To 100 g of 4-(6-bromohexyloxy)-N-(2-hydroxyethyl)benzamide was added dropwise 112 g (75 ml) of thionyl chloride over a 20 minute period. The mixture was stirred for 45 minutes and then diluted with several volumes of ether. A solid product separated which was collected and rinsed with ether to give 90 g of 2-[4-(6-bromohexyloxy)phenyl]-4,5-dihydro-oxazole.

(f) 5-{7-[4-(4,5-Dihydro-2-oxazolyl)phenoxy]heptyl}-3-methylisoxazole [XXI]

To a stirred solution of 6.0 ml of diisopropylamine in 50 ml of tetrahydrofuran at 0° C. was added 22 ml of 2.1M n-butyllithium in hexane over a period of 20 minutes. The mixture was stirred 30 minutes at 5° C., then cooled to −55° C., and 4.5 g of 3,5-dimethylisoxazole was added dropwise during 15 minutes. The resulting slurry was stirred for 30 minutes at −60° C. and 12.4 g of 2-[4-(6-bromohexyloxy)phenyl]-4,5-dihydro-oxazole in 35 ml of tetrahydrofuran was then added dropwise. After the addition was complete, the mixture was stirred for one hour during which the temperature rose to −40° C. The reaction mixture was allowed to warm to room temperature, 75 ml of water was then added dropwise, and the mixture was extracted with ethyl acetate. The ethyl acetate extracts were dried and concentrated in vacuo, and the residue triturated with ether. The ether insoluble fraction (10.5) consisted essentially of 5-{7-[4-(4,5-dihydro-2-oxazolyl)phenoxy]-heptyl}-3-methylisoxazole, identical with the product of Example 1, part (c).

EXAMPLE 9

(a) N-(2-Hydroxyethyl)-4-hydroxybenzamide [XV; $R_1$, $R_2$, $R_4'$, $R_5'$ and $R_6'$=H, OH at 4-position]

A mixture of 80 g of methyl 4-hydroxybenzoate and 120 ml of ethanolamine was heated at 150° C. for five hours during which time 14.2 ml of methanol was distilled off. The excess ethanolamine was removed in vacuo, and the residue was treated with two 150 ml portions of chloroform. The chloroform was removed in vacuo and the residual oil dissolved in acetone from which the product crystallized to give 45.3 g of N-(2-hydroxyethyl)-4-hydroxybenzamide.

(b) 4,5-Dihydro-2-(4-hydroxyphenyl)oxazole [XVI; $R_1$, $R_2$, $R_4'$, $R_5'$ and $R_6'$=H, OH at 4-position]

Thionyl chloride (160 ml) was added to 40 g of N-(2-hydroxyethyl)-4-hydroxybenzamide with evolution of gas. The reaction mixture was ultrasonicated for 1.75 hours, then cooled and diluted with ether. The resulting solid product was collected by filtration, washed with ether and dried overnight in a vacuum oven at 40° C. to give 42.5 g of 4,5-dihydro-2-(4-hydroxyphenyl)oxazole in the form of its hydrochloride salt, m.p. 162°-163° C.

(c) 5-(7-Bromoheptyl)-3-methylisoxazole [V; $R'$=$CH_3$, $R_3'$=H, Y=$(CH_2)_7$, Hal=Br]

To a stirred solution of 46.1 ml of diisopropylamine in 100 ml of tetrahydrofuran at 0°-5° C. was added 126 ml of 2.6M n-butyllithium in hexane over a period of about 20 minutes. The mixture was cooled to −50° C., 31.95 g of 3,5-dimethylisoxazole was added and the mixture stirred for 30 minutes. The latter mixture was cooled to −78° C. and 101.6 ml of 1,6-dibromohexane was added dropwise. After the addition was complete, the temperature of the reaction mixture was allowed to rise to room temperature and kept there for about 40 hours. Saturated aqueous ammonium chloride solution was then added and the mixture extracted with ethyl acetate. The ethyl acetate extracts were dried over anhydrous magnesium sulfate and concentrated in vacuo. The residue was distilled to remove excess dibromide (b.p. 50° C., 0.5 mm) and suspended in hexane. The suspension was decolorized with charcoal, filtered and cooled in a refrigerator overnight. The mixture was filtered and the filtrate concentrated in vacuo to give 57 g of 5-(7-bromoheptyl)-3-methylisoxazole as a colorless oil.

(d) 5-{7-[4-(4,5-Dihydro-2-oxazolyl)phenoxy]heptyl}-3-methylisoxazole [XXI]

Sodium iodide (6.43 g, 0.043 m) was added to a solution of 9.36 g (0.036 m) of 5-(7-bromoheptyl)-3-methylisoxazole in 100 ml of acetonitrile, and the mixture was stirred at reflux for two hours and then cooled to room temperature. Potassium carbonate (11.8 g, 0.086 m) and 10.12 g (0.043 m) of 4,5-dihydro-2-(4-hydroxyphenyl)oxazole hydrochloride were then added, and the reaction mixture was heated at reflux for 24 hours. The reaction mixture was cooled, poured into water and extracted with three 75 ml portions of ethyl acetate. The extracts were dried over anhydrous magnesium sulfate and concentrated in vacuo. The solid residue was recrystallized from acetonitrile to give a first crop consisting of recovered 4,5-dihydro-2-(4-hydroxyphenyl)oxazole (1.0 g) and a second crop consisting of the desired product, 5-{7-[4-(4,5-dihydro-2-oxazolyl)phenoxy]heptyl}-3-methylisoxazole, m.p. 85°-86° C., identical with the compound obtained in Example 1, part (c) and Example 8, part (f), as determined by thin layer chromatography analysis.

EXAMPLE 10

(a) N-(2-Hydroxyethyl)-4-hydroxybenzamide [XV; $R_1$, $R_2$, $R_4'$, $R_5'$ and $R_6'$=H, OH at 4-position]

A 5 liter, three-necked flask, equipped with a Dean-Stark trap, mechanical stirrer and thermometer was charged with 608 g (4.0 moles) of methyl p-hydroxybenzoate and 488 g (8.0 moles) of 2-aminoethanol. The mixture, when stirred and heated to 135° C., gave a clear solution. After heating the mixture for 2.5 hrs at 135°-140° C., 114 ml of methanol was collected in the Dean-Stark trap. The solution was cooled to 70° C. at which time some thickening occurred. The solution was treated with 2 liters of 2N hydrochloric acid and allowed to cool. A white crystalline precipitate formed and the mixture was stirred and cooled to 0° C. to complete crystallization. The solid was filtered and dried in vacuo at 65° C. overnight. Wt.=634.6 g (87.6%), m.p. 156°-157° C.

(b) 4,5-Dihydro-2-(4-hydroxyphenyl)oxazole [XVI; $R_1$, $R_2$, $R_4'$, $R_5'$ and $R_6'$=H, OH at 4-position]

A 22 liter, three-necked flask was charged with 634 g (3.5 moles) of the β-hydroxyamide of part (a) and 5.2 liters of isopropyl acetate. The flask was cooled externally in a bath with tap water (10°–15° C.) and 390 ml (5.25 moles) of thionyl chloride was added to the stirred suspension over 45 minutes. A mild exotherm was apparent, but the temperature was maintained between 25° and 30° C. After stirring 2 hr at ambient temperature, the suspension was filtered and the cake washed with isopropyl acetate. After air drying for two hours, the solid was transferred to a 22 liter flask and dissolved in 1.4 liters of water. The solution was treated with saturated sodium bicarbonate solution until slightly basic. A heavy white precipitate formed during the addition. The suspension was filtered and the resulting white solid was washed with cold water and dried overnight in vacuo at 65° C. A total of 522 g (91.5%) of the 4,5-dihydro-2-(4-hydroxyphenyl)oxazole, m.p. 209°–211° C., was obtained.

(c) 2-[4-(6-Bromohexyloxy)phenyl]-4,5-dihydrooxazole [XVII; $R_1$, $R_2$, $R_4'$, $R_5'$ and $R_6'$=H, Hal=Br, $Y=(CH_2)_6$, oxazole at 4-position]

A stirring suspension of 163 g (1.0 mole) of 4,5-dihydro-2-(4-hydroxyphenyl)oxazole and 276 g (2.0 mole) milled potassium carbonate in 750 ml acetonitrile was heated to reflux in a 5 liter round-bottomed flask. A total of 457.5 ml (3.0 mole) of 1,6-dibromohexane was added all at once and reflux continued for 1 hour. The reaction mixture was filtered and the cake of inorganic salts washed with 100 ml of acetonitrile. The filtrate was evaporated on a rotary evaporator (bath temperature <40° C.) and the resulting residue slurried in 1.6 liters of hexane and chilled to 0° C. The resulting white solid was filtered and washed with 500 ml cold hexane. The recovery was 263 g (80%) of white solid. A total of 535 g of crude product was slurried in 1.1 liter of refluxing tert-butyl methyl ether. The mixture was allowed to cool to 30° C. and filtered with suction. The filtrate was cooled to 0° C. and the product crystallized. The solid was filtered off and dried to yield 372 g (70% recovery) of 2-[4-(6-bromohexyloxy)phenyl]-4,5-dihydro-oxazole, m.p. 79°–81° C. The crude product can also be recrystallized from acetonitrile. This removes excess dibromohexane and most of an undesired byproduct formed by reaction of 1 mole of dibromohexane with 2 moles of 4,5-dihydro-2-(4-hydroxyphenyl)oxazole, namely 1,6-bis[4-(4,5-dihydro-2-oxazolyl)phenoxy]hexane, m.p. 174°–175° C. when isolated and purified.

(d) 5-{7-[4-(4,5-Dihydro-2-oxazolyl)phenoxy]heptyl}-3-methylisoxazole [XXI]

To a stirring solution of 48.6 g (0.48 moles) diisopropylamine in 520 ml tetrahydrofuran (THF) at −5° C. (ice/acetone bath) was added 185 ml of 2.6M n-butyllithium (0.48 moles) under nitrogen. The addition was complete after 30 minutes and the pale yellow solution was maintained at −5° to +5° C. for an additional 30 minutes. The ice/acetone bath was replaced by Dry Ice/acetone and when the internal temperature reached −55° C., 46.6 g (0.48 moles) 3,5-dimethylisoxazole was added dropwise over 20 minutes. This solution was allowed to stir an additional 30–40 minutes at −55° C. or lower. A solution containing 135 g (0.41 moles) 2-[4-(6-bromohexyloxy)phenyl]-4,5-dihydro-oxazole dissolved in 400 ml THF was added dropwise (via nitrogen pump) over 35 minutes. The temperature during the addition was kept below −50° C. by carefully controlling the rate of the addition. The heavy suspension was stirred for an additional hour. The Dry Ice bath was removed and the reaction was quenched by dropwise addition of 10 ml water. The reaction mixture was allowed to warm to about 5°–10° C. and then poured into 1 liter water and 1 liter ethyl acetate. The aqueous layer was set aside and the organic layer was washed once with water and brine. The extract was dried over magnesium sulfate and evaporated to near dryness under water vacuum. The crude crystalline product was dissolved in 600 ml warm acetonitrile, filtered thru a pad of solka floc and allowed to crystallize at room temperature. After two hours, the heavy crystalline precipitate was cooled to 10° C. and filtered to give 108 g (76%) 5-{7-[4-(4,5-dihydro-2-oxazolyl)phenoxy]heptyl}-3-methylisoxazole, m.p. 97°–98° C., after drying 24 hrs at 60° C.

An effective way of removing traces of the by-product produced in part (c) carried through to the final product is by recrystallization from ethanol (solution formation at 50° C., crystallization at 40° C. and collection at 35° C.).

EXAMPLE 11

5-{7-[4-(4,5-Dihydro-2-oxazolyl)phenoxy]heptyl}-3-isoxazolemethanol [XXII]

5-{7-[4-(4,5-Dihydro-2-oxazolyl)phenoxy]heptyl}-3-methylisoxazole (Example 1c) (1 g) was added to each of three 10-liter fermentation tanks containing a culture of Aspergillus niger ($A_1$) in soy-dextrose medium. After 24 hours, thin layer chromatography showed essentially complete conversion to a more polar product. The total fermentation brews were extracted with two volumes each of dichloromethane. These were combined and concentrated in vacuo. The concentrate was washed with 0.05N sodium hydroxide and with water, leaving an oily material upon removal of remaining solvent. Several crystallizations from ethyl acetate and from acetone yielded 330 mg of 5-{7-[4-(4,5-dihydro-2-oxazolyl)phenoxy]heptyl}-3-isoxazolemethanol, colorless needles, m.p. 122°–124° C. The structure was established by nmr, ir and uv spectra.

EXAMPLE 12

The procedure of Example 11 was repeated but using Trichothecium roseum ($T_1$) as the microorganism. From 1.5 g of starting material there was obtained, using preparative silica gel thin layer chromatography for purification, 200 mg of α-{6-[4-(4,5-dihydro-2-oxazolyl)phenoxy]hexyl}-3-methyl-5-isoxazolemethanol [XXIII], colorless crystals, m.p. 132°–133° C.; structure established by mass spectrum and nmr spectrum.

EXAMPLE 13

(a) N-(2-Hydroxyethyl)-3-chloro-4-hydroxybenzamide [XV; $R_1$=3-Cl, $R_2$=H, $R_4'$, $R_5'$ and $R_6'$=H, OH at 4-position] was prepared from methyl 3-chloro-4-hydroxybenzoate and ethanolamine according to the procedure of Example 9, part (a). The product thus obtained had the m.p. 148°–150° C.

(b) 4,5-Dihydro-2-(3-chloro-4-hydroxyphenyl)oxazole [XVI; $R_1$=3-Cl, $R_2$=H, $R_4'$, $R_5'$ and $R_6'$=H, oxazole at 4-position] was prepared by reacting N-(2-hydroxyethyl)-2-chloro-4-hydroxybenzamide with thionyl chloride according to the procedure of Example 9, part (a). The product was obtained in the form of its hydrochloride salt, m.p. 153°–155° C.

(c) 5-{7-[2-Chloro-4-(4,5-dihydro-2-oxazolyl)phenoxy]heptyl}-3-methylisoxazole [IX; R=CH$_3$, R$_2$, R$_3$, R$_4$, R$_5$ and R$_6$=H, R$_1$=2-Cl, Y=(CH$_2$)$_7$, oxazole at 4-position] was prepared from 5-(7-bromoheptyl)-3-methylisoxazole (Example 9, part c) and 4,5-dihydro-2-(3-chloro-4-hydroxyphenyl)oxazole according to the procedure of Example 9, part (d), and was obtained in the form of a colorless solid, m.p. 120°–120.5° C. when recrystallized from methanol and further purified by chromatography.

EXAMPLE 14

(a) 5-(6-Bromohexyl)-3-methylisoxazole [V; R'=CH$_3$, R$_3$'=H, Y=(CH$_2$)$_6$, Hal=Br] was prepared from 1,5-dibromopentane and 3,5-dimethylisoxazole according to the procedure of Example 9, part (c), and was obtained as a yellow oil in 46% yield.

(b) 5-{6-[4-(4,5-Dihydro-2-oxazolyl)phenoxy]hexyl}-3-methylisoxazole [IX; R=CH$_3$, R$_1$, R$_2$, R$_3$, R$_4$, R$_5$ and R$_6$=H, Y=(CH$_2$)$_6$, oxazole at 4-position] was prepared by reacting 5-(6-bromohexyl)-3-methylisoxazole and 4,5-dihydro-2-(4-hydroxyphenyl)oxazole (free base, m.p. 200°–202° C.) according to the procedure of Example 9, part (d), and was obtained as a colorless solid, m.p. 88° C. when recrystallized from hexane.

EXAMPLE 15

(a) 5-(5-Bromopentyl)-3-methylisoxazole [V; R'=CH$_3$, R$_3$'=H, Y=(CH$_2$)$_5$, Hal=Br] was prepared from 1,4-dibromobutane and 3,5-dimethylisoxazole according to the procedure of Example 9, part (c), and was obtained as an oil in 52% yield.

(b) 5-{5-[2-Chloro-4-(4,5-dihydro-2-oxazolyl)phenoxy]pentyl}-3-methylisoxazole [IX; R=CH$_3$, R$_1$=2-Cl, R$_2$, R$_3$, R$_4$, R$_5$ and R$_6$=H, Y=(CH$_2$)$_5$, oxazole at 4-position] was prepared from 5-(5-bromopentyl)-3-methylisoxazole and 4,5-dihydro-2-(3-chloro-4-hydroxyphenyl)oxazole (Example 13b) according to the procedure of Example 9, part (d), and was obtained in the form of a colorless solid, m.p. 102°–104° C. when recrystallized from isopropyl alcohol.

EXAMPLE 16

5-{6-[2-Chloro-4-(4,5-dihydro-2-oxazolyl)phenoxy]hexyl}-3-methylisoxazole [IX; R=CH$_3$, R$_1$=2-Cl, R$_2$, R$_3$, R$_4$, R$_5$ and R$_6$=H, Y=(CH$_2$)$_6$, oxazole at 4-position] was prepared from 5-(6-bromohexyl)-3-methylisoxazole (Example 14a) and 4,5-dihydro-2-(3-chloro-4-hydroxyphenyl)oxazole (Example 13b) according to the procedure of Example 9, part (b), and was obtained in the form of a colorless solid, m.p. 64.5°–65.5° C. when recrystallized from etherpentane.

EXAMPLE 17

(a) 4,5-Dihydro-2-(3-chloro-4-hydroxyphenyl)-4-methyloxazole [XVI; R$_4$'=CH$_3$, R$_2$, R$_5$' and R$_6$'=H, R$_1$=3-Cl, OH at 4-position] was prepared from methyl 3-chloro-4-hydroxybenzoate and 2-aminopropanol, and cyclization of the resulting N-(2-hydroxypropyl)-4-hydroxybenzamide with thionyl chloride according to the procedures of Example 9, parts (a) and (b), and was obtained in 60% yield as a colorless solid, m.p. 176°–178° C. when recrystallized from acetone.

(b) 5-{7-[2-Chloro-4-(4,5-dihydro-4-methyl-2-oxazolyl)phenoxy]heptyl}-3-methylisoxazole [IX; R and R$_4$=CH$_3$, R$_2$, R$_3$, R$_5$ and R$_6$=H, R$_1$=2-Cl, Y=(CH$_2$)$_7$, oxazole at 4-position] was prepared from 3,5-dihydro-2-(3-chloro-4-hydroxyphenyl)-4-methyloxazole and 5-(7-bromoheptyl)-3-methylisoxazole according to the procedure of Example 9, part (d), and was obtained in 69% yield as a colorless solid, m.p. 80°–82° C. when recrystallized first from cyclohexane and then from tertiary-butyl methyl ether.

EXAMPLE 18

(a) 5-(8-Bromooctyl)-3-methylisoxazole [V; R'=CH$_3$, R$_3$'=H, Y=(CH$_2$)$_8$, Hal=Br] was prepared from 1,7-dibromoheptane and 3,5-dimethylisoxazole according to the procedure of Example 9, part (c) and was obtained in 52% yield as a yellow oil.

(b) 5-{8-[4-(4,5-Dihydro-2-oxazolyl)phenoxy]octyl}-3-methylisoxazole [IX; R=CH$_3$, R$_1$, R$_2$, R$_3$, R$_4$, R$_5$ and R$_6$=H, Y=(CH$_2$)$_8$, oxazole at 4-position] was prepared from 5-(8-bromooctyl)-3-methylisoxazole and 4,5-dihydro-2-(4-hydroxyphenyl)oxazole according to the procedure of Example 9, part (d), and was obtained as a colorless solid, m.p. 73.5°–74.5° C. when recrystallized from pentane.

EXAMPLE 19

(a) 4,5-Dihydro-2-(3-fluoro-4-hydroxyphenyl)oxazole [XVI; R$_2$, R$_4$', R$_5$' and R$_6$'=H, R$_1$=3-F, oxazole at 4-position] was prepared by reacting methyl 3-fluoro-4-hydroxybenzoate with ethanolamine, and treating the resulting N-(2-hydroxyethyl)-3-fluoro-4-hydroxybenzamide with thionyl chloride, according to the procedures of Example 9, parts (a) and (b), and was obtained in 41% yield as a colorless solid, m.p. 201°–203° C., when recrystallized from tetrahydrofuran.

(b) 5-{7-[4-(4,5-Dihydro-2-oxazolyl)-2-fluorophenoxy]heptyl}-3-methylisoxazole [IX; R=CH$_3$, R$_2$, R$_3$, R$_4$, R$_5$ and R$_6$=H, R$_1$=2-F, Y=(CH$_2$)$_7$, oxazole at 4-position] was prepared from 4,5-dihydro-2-(3-fluoro-4-hydroxyphenyl)oxazole and 5-(7-bromoheptyl)-3-methylisoxazole according to the procedure of Example 9, part (d), and was obtained in 55% yield as a colorless solid, m.p. 83°–84° C., when recrystallized first from methanol and then from tertiary-butyl methyl ether.

EXAMPLE 20

5-{5-[4-(4,5-Dihydro-2-oxazolyl)-2-fluorophenoxy]pentyl}-3-methylisoxazole [IX; R=CH$_3$, R$_2$, R$_3$, R$_4$, R$_5$ and R$_6$=H, R$_1$=2-F, Y=(CH$_2$)$_5$, oxazole at 4-position] was prepared from 4,5-dihydro-2-(3-fluoro-4-hydroxyphenyl)oxazole (Example 19a) and 5-(5-bromopentyl)-3-methylisoxazole (Example 15a), according to the procedure of Example 9, part (d), and was obtained in 51% yield as a colorless solid, m.p. 95°–96° C., when recrystallized from tertiary-butyl methyl ether.

EXAMPLE 21

(a) 5-(4-Bromobutyl)-3-methylisoxazole [V; R'=CH$_3$, R$_3$'=H, Y=(CH$_2$)$_4$, Hal=Br] was prepared from 1,3-dibromopropane and 3,5-dimethylisoxazole according to the procedure of Example 9, part (c), and was obtained in 54% yield as a yellow oil after chromatography on silica gel.

(b) 5-{4-[4-(4,5-Dihydro-2-oxazolyl)phenoxy]butyl}-3-methylisoxazole [IX; R=CH$_3$, R$_1$, R$_2$, R$_3$, R$_4$, R$_5$ and R$_6$=H, Y=(CH$_2$)$_4$, oxazole at 4-position] was prepared from 5-(4-bromobutyl)-3-methylisoxazole and 4,5-dihydro-2-(4-hydroxyphenyl)oxazole according to the procedure of Example 9, part (d), and was obtained in 75% yield as a colorless solid, m.p. 93°–94° C., when recrystallized from isopropyl acetate.

EXAMPLE 22

5-{8-[2-Chloro-4-(4,5-dihydro-2-oxazolyl)phenoxy]octyl}-3-methylisoxazole [IX; R=CH$_3$, R$_2$, R$_3$, R$_4$, R$_5$ and R$_6$=H, R$_1$=2-Cl, Y=(CH$_2$)$_8$, oxazole at 4-position] was prepared from 4,5-dihydro-2-(3-chloro-4-hydroxyphenyl)oxazole (Example 13b) and 5-(8-bromooctyl)-3-methylisoxazole (Example 18a) according to the procedure of Example 9, part (d), and was obtained in the form of a colorless solid, m.p. 63°–64° C. when recrystallized from ether.

EXAMPLE 23

5-{7-[4-(4,5-Dihydro-5-hydroxymethyl-2-oxazolyl)phenoxy]heptyl}-3-methylisoxazole [IX; R=CH$_3$, R$_1$, R$_2$, R$_3$, R$_4$ and R$_5$=H, R$_6$=CH$_2$OH, Y=(CH$_2$)$_7$, oxazole at 4-position] was prepared from the ethyl iminoester hydrochloride of 5-[7-(4-cyanophenoxy)heptyl]-3-methylisoxazole and 3-amino-1,2-propanediol according to the procedure of Example 1, part (c), and was obtained in about 60% yield in the form of a colorless solid, m.p. 75°–76° C., when recrystallized first from isopropyl acetate and then from acetonitrile.

EXAMPLE 24

5-{4-[2-Chloro-4-(4,5-dihydro-2-oxazolyl)phenoxy]butyl}-3-methylisoxazole [IX; R=CH$_3$, R$_2$, R$_3$, R$_4$, R$_5$ and R$_6$=H, R$_1$=2-Cl, Y=(CH$_2$)$_4$, oxazole at 4-position] was prepared from 4,5-dihydro-2-(3-chloro-4-hydroxyphenyl)oxazole (Example 13b) and 5-(4-bromobutyl)-3-methylisoxazole (Example 21a), according to the procedure of Example 9, part (d), and was obtained in 69% yield in the form of a colorless solid, m.p. 75°–76° C., when recrystallized from isopropyl acetate.

EXAMPLE 25

5-{7-[4-(4,5-Dihydro-4-hydroxymethyl-2-oxazolyl)phenyl]heptyl}-3-methylisoxazole [IX; R=CH$_3$, R$_4$=CH$_2$OH, R$_1$, R$_2$, R$_3$ and R$_5$=H, n=7, oxazole at 4-position] was prepared from the methyl imino-ester hydrochloride of 5-[7-(4-cyanophenyl)heptyl]-3-methylisoxazole and 2-amino-1,3-propanediol, according to the procedure of Example 6, part (g), and was obtained in about 40% yield in the form of a pale pink solid, m.p. 68°–69° C., when recrystallized first from isopropyl acetate-pentane and then from acetonitrile.

EXAMPLE 26

(a) 4,5-Dihydro-2-(3-hydroxyphenyl)oxazole [XVI; R$_1$, R$_2$, R$_4$', R$_5$' and R$_6$'=H, OH at 3-position] was prepared by reacting methyl 3-hydroxybenzoate and ethanolamine, and treating the resulting N-(2-hydroxyethyl)-3-hydroxybenzamide with thionyl chloride according to the procedures of Example 9, parts (a) and (b), and was obtained in 84% yield in the form of a colorless solid, m.p. 184°–185° C., when recrystallized from an acetone-tetrahydrofuran mixture.

(b) 5-{7-[3-(4,5-Dihydro-2-oxazolyl)phenoxy]heptyl}-3-methylisoxazole [IX; R=CH$_3$, R$_1$, R$_2$, R$_3$, R$_4$, R$_5$ and R$_6$=H, Y=(CH$_2$)$_7$, oxazole at 3-position], was prepared from 4,5-dihydro-2-(3-hydroxyphenyl)oxazole and 5-(7-bromoheptyl)-3-methylisoxazole according to the procedure of Example 9, part (d), and was obtained in 35% yield in the form of a colorless solid, m.p. 54°–55° C., when chromatographed and recrystallized from ether-hexane.

EXAMPLE 27

(a) 4,5-Dihydro-2-(3-chloro-4-hydroxyphenyl)-4-methyloxazole [XVI; R$_4$'=CH$_3$, R$_2$, R$_5$' and R$_6$'=H, R$_1$=3-Cl, OH at 4-position] was prepared by reacting methyl 3-chloro-4-hydroxybenzoate with 2-amino-1-propanol, and treating the resulting N-(1-methyl-2-hydroxyethyl)-3-chloro-4-hydroxybenzamide with thionyl chloride according to the procedures of Example 9, parts (a) and (b), and was obtained in 69% yield as a colorless solid, m.p. 174°–176° C., when recrystallized from acetone.

(b) 5-{8-[2-Chloro-4-(4,5-dihydro-4-methyl-2-oxazolyl)phenoxy]octyl}-3-methylisoxazole [IX; R and R$_4$=CH$_3$, R$_2$, R$_3$, R$_5$ and R$_6$=H, R$_1$=2-Cl, Y=(CH$_2$)$_8$, oxazole at 4-position] was prepared by reacting 4,5-dihydro-2-(3-chloro-4-hydroxyphenyl)-4-methyloxazole with 5-(8-bromooctyl)-3-methylisoxazole (Example 18a) according to the procedure of Example 9, part (d), and was obtained in 67% yield in the form of a pale yellow oil, m.p. below room temperature.

EXAMPLE 28

5-{7-[4-(4,5-Dihydro-2-oxazolyl)phenoxy]heptyl}-3-isoxazolemethanol acetate [IX; R=CH$_3$COOCH$_2$, R$_1$, R$_2$, R$_3$, R$_4$, R$_5$ and R$_6$=H, Y=(CH$_2$)$_7$, oxazole at 4-position]

A solution of 2.80 g of 5-{7-[4-(4,5-dihydro-2-oxazolyl)phenoxy]heptyl}-3-isoxazolemethanol (Example 11) and 0.82 g of acetic anhydride in pyridine was allowed to stand overnight at room temperature. The reaction mixture was poured into ice water and the solid material which formed was collected, dried and recrystallized from isopropyl alcohol to give 2.5 g of 5-{7-[4-(4,5-dihydro-2-oxazolyl)phenoxy]heptyl}-3-isoxazolemethanol acetate, colorless solid, m.p. 76°–77° C.

EXAMPLE 29

(a) 3,5-Dimethyl-4-hydroxymethylisoxazole

To a suspension of 23.53 g of lithium aluminum hydride in 600 ml of ether was added dropwise 64 g of 4-carbethoxy-3,5-dimethylisoxazole in 100 ml of ether at a rate so that gentle reflux occurred. The addition was complete in about two hours, and the mixture was stirred overnight under nitrogen. A saturated solution of sodium sulfate was added dropwise under nitrogen until the excess lithium aluminum hydride was decomposed. The resulting suspension was filtered and the filtrate concentrated to an oil which was distilled to give 36.4 g of 3,5-dimethyl-4-hydroxymethylisoxazole, b.p. 130°–140° C. (0.1 mm).

(b) 5-{7-[4-(4,5-Dihydro-2-oxazolyl)phenoxy]heptyl}-3-methyl-4-isoxazolemethanol [IX; R=CH$_3$, R$_1$, R$_2$, R$_4$, R$_5$ and R$_6$=H, R$_3$=CH$_2$OH, Y=(CH$_2$)$_7$, oxazole at 4-position] was prepared from 3,5-dimethyl-4-hydroxymethylisoxazole and 2-[4-(6-bromohexyloxy)phenyl]-4,5-dihydroxazole (Example 10c), according to the procedure described in Example 10, part (d), and was obtained in the form of a colorless solid, m.p. 95°–97° C., when recrystallized from acetonitrile.

EXAMPLE 30

5-{5-[3-(4,5-Dihydro-2-oxazolyl)phenoxy]pentyl}-3-methylisoxazole [IX; R=CH$_3$, R$_1$, R$_2$, R$_3$, R$_4$, R$_5$ and R$_6$=H, Y=(CH$_2$)$_5$, oxazole at 3-position] was prepared from 4,5-dihydro-2-(3-hydroxyphenyl)oxazole (Example 26a) and 5-(5-bromopentyl)-3-methylisoxazole (Example 15a) according to the procedure of Example 9, part (d), and was obtained in 49% yield in the form of colorless needles, m.p. 65°–67° C., when recrystallized from isopropyl acetate-hexane.

EXAMPLE 31

(a) 4,5-Dihydro-2-(4-hydroxy-3-methylphenyl)oxazole [XVI; $R_2$, $R_4'$, $R_5'$ and $R_6'$=H, $R_1$=3-$CH_3$, OH at 4-position] was prepared by reacting methyl 4-hydroxy-3-methylbenzoate and ethanolamine, and treating the resulting N-(2-hydroxyethyl)-4-hydroxy-3-methylbenzamide with thionyl chloride according to the procedures of Example 9, parts (a) and (b), and was obtained in 43% yield in the form of a colorless solid, m.p. 190°–191° C., when recrystallized from methanol.

(b) 5-{7-[4-(4,5-Dihydro-2-oxazolyl)-2-methylphenoxy]heptyl}-3-methylisoxazole [IX; R=$CH_3$, $R_2$, $R_3$, $R_4$, $R_5$ and $R_6$=H, $R_1$=2-$CH_3$, Y=$(CH_2)_7$, oxazole at 4-position] was prepared from 4,5-dihydro-2-(4-hydroxy-3-methylphenyl)oxazole and 5-(7-bromoheptyl)-3-methylisoxazole according to the procedure of Example 9, part (d), and was obtained in 45% yield as a light-tan solid, m.p. 90°–92° C., when recrystallized first from methanol and then from tertiary-butyl methyl ether.

EXAMPLE 32

5-{5-[2-Chloro-4-(4,5-dihydro-4-methyl-2-oxazolyl)-phenoxy]pentyl}-3-methylisoxazole [IX; R and $R_4$=$CH_3$, $R_2$, $R_3$, $R_5$ and $R_6$=H, $R_1$=2-Cl, Y=$(CH_2)_5$, oxazole at 4-position] was prepared from 3,5-dihydro-2-(3-chloro-4-hydroxyphenyl)-4-methyloxazole (Example 17a) and 5-(5-bromopentyl)-3-methylisoxazole (Example 15a) according to the procedure of Example 9, part (d), and was obtained in 51% yield in the form of a colorless solid, m.p. 81°–83° C. when recrystallized from a tertiary-butyl methyl ether-hexane mixture.

EXAMPLE 33

5-{7-[4-(4,5-Dihydro-4-hydroxymethyl-2-oxazolyl)-phenoxy]heptyl}-3-methylisoxazole [IX; R=$CH_3$, $R_4$=$CH_2OH$, $R_1$, $R_2$, $R_3$, $R_5$ and $R_6$=H, Y=$(CH_2)_7$, oxazole at 4-position] was prepared from the ethyl imino-ester hydrochloride of 5-[7-(4-cyanophenoxy)-heptyl]-2-methylisoxazole and 2-amino-1,3-propanediol, according to the procedure of Example 1, part (c), and was obtained in 73% yield in the form of a colorless solid, m.p. 77°–78° C. when recrystallized from an isopropyl acetate-hexane mixture.

EXAMPLE 34

(a) 4,5-Dihydro-2-(4-hydroxyphenyl)-5-methyloxazole [XVI; $R_1$, $R_2$, $R_4'$ and $R_5'$=H, $R_6'$=$CH_3$, OH at 4-position] was prepared by reacting methyl 4-hydroxybenzoate with 1-amino-2-propanol and treating the resulting N-(2-hydroxypropyl)-4-hydroxybenzamide with thionyl chloride according to the procedures of Example 9, parts (a) and (b) and was obtained in 29% yield in the form of a colorless solid, m.p. 207°–209° C., when recrystallized from an acetonitrile-tetrahydrofuran mixture.

(b) 5-{7-[4-(4,5-Dihydro-5-methyl-2-oxazolyl)-phenoxy]heptyl}-3-methylisoxazole [IX; R and $R_6$=$CH_3$, $R_1$, $R_2$, $R_3$, $R_4$ and $R_5$=H, Y=$(CH_2)_7$, oxazole at 4-position] was prepared from 4,5-dihydro-2-(4-hydroxyphenyl)-5-methyloxazole and 5-(7-bromopentyl)-3-methylisoxazole according to the procedure of Example 9, part (d), and was obtained in the form of a colorless solid, m.p. 81°–82° C. when recrystallized from acetonitrile.

EXAMPLE 35

4-Chloromethyl-5-{7-[4-(4,5-dihydro-2-oxazolyl)-phenoxy]heptyl}-3-methylisoxazole [IX; R=$CH_3$, $R_1$, $R_2$, $R_4$, $R_5$ and $R_6$=H, $R_3$=$CH_2Cl$, Y=$(CH_2)_7$, oxazole at 4-position]

To a solution of 2.1 ml of thionyl chloride in 5.0 ml of methylene dichloride cooled in an ice-bath was added over a 30 minute period a suspension of 5 g of 5-{7-[4-(4,5-dihydro-2-oxazolyl)phenoxy]heptyl}-3-methyl-4-isoxazolemethanol (Example 29b) in 20 ml of methylene dichloride. The reaction mixture was stirred at 0° C. for 2 hours and then at room temperature for 3 hours. The solvent was then removed in vacuo and the residue triturated with ether. The solid product was collected and recrystallized from acetonitrile to give 4.5 g of 4-chloromethyl-5-{7-[4-(4,5-dihydro-2-oxazolyl)-phenoxy]heptyl}-3-methylisoxazole in the form of its monohydrochloride salt, tan solid, m.p. 103°–104° C.

EXAMPLE 36

5-{7-[4-(4,5-Dihydro-2-oxazolyl)phenoxy]heptyl}-3-methyl-4-(1-pyrrolidylmethyl)isoxazole [IX; R=$CH_3$, $R_1$, $R_2$, $R_4$, $R_5$ and $R_6$=H, $R_3$=1-pyrrolidylmethyl, Y=$(CH_2)_7$, oxazole at 4-position]

A solution of 2.8 g of 4-chloromethyl-5-}7-[4-(4,5-dihydro-2-oxazolyl)phenoxy]heptyl}-3-methylisoxazole (Example 35) and 1.3 g of pyrrolidine in 50 ml of dimethylformamide was heated on a steam bath for six hours and then kept overnight at room temperature. The solvent was removed in vacuo, and the residue was dissolved in water and made basic with sodium bicarbonate solution. The solid product which separated was collected and dried to give 1.3 g of 5-{7-[4-(4,5-dihydro-2-oxazolyl)phenoxy]heptyl}-3-methyl-4-(1-pyrrolidylmethyl)isoxazole, m.p. 98°–99° C.

By replacing the pyrrolidine in the foregoing example by a molar equivalent amount of ammonia, ethylamine, dimethylamoine, piperidine or morpholine, it is contemplated that there can be obtained, respectively, 4-aminomethyl-5-{7-[4-(4,5-dihydro-2-oxaz/lyl)phenoxy]heptyl}-3-methylisoxazole; 5-{7-[4-(4,5-dihydro-2-oxazolyl)phenoxy]heptyl}-4-ethylaminomethyl-3-methylisoxazole; 5-{7-[4-(4,5-dihydro-2-oxazolyl)-phenoxy]heptyl}-4-dimethylaminomethyl-3-methylisoxazole; 5-{7-[4-(4,5-dihydro-2-oxazolyl)-phenoxy]heptyl}-3-methyl-4-(1-piperidylmethyl)isoxazole; or 5-{7-[4-(4,5-dihydro-2-oxazolyl)phenoxy]heptyl}-3-methyl-4-(4-morpholinylmethyl)isoxazole.

It is further contemplated that the 4-aminomethyl-5-{7-[4-(4,5-dihydro-2-oxazolyl)phenoxy]heptyl}-3-methylisoxazole can be caused to react with acetyl chloride to produce the corresponding 4-acetylamino compound.

EXAMPLE 37

3-{5-[2-Chloro-4-(4,5-dihydro-2-oxazolyl)phenoxy]-pentyl}-5-methylisoxazole [III; $R_2$, $R_4$, $R_5$ and $R_6$=H, $R_1$=2-Cl, $R_9$=$CH_3$, n=5, oxazole at 4-position] was prepared from 3-(5-bromopentyl)-5-methylisoxazole (Example 7f) and 4,5-dihydro-2-(3-chloro-4-hydroxyphenyl)oxazole (Example 13b) according to the procedure of Example 9, part (d), and was obtained in 62% yield in the form of a colorless solid, m.p. 102°–103° C. when recrystallized from methanol.

EXAMPLE 38

(a) 4,5-Dihydro-2-(4-hydroxy-2-methylphenyl)oxazole [XVI; $R_2$, $R_4'$, $R_5'$ and $R_6'$=H, $R_1$=2-$CH_3$, OH at 4-position] was prepared by reacting methyl 4-hydroxy-2-methylbenzoate and ethanolamine, and treating the resulting N-(2-hydroxyethyl)-4-hydroxy-2-methylbenzamide with thionyl chloride according to the procedures of Example 9, parts (a) and (b), and was obtained in 34% yield, m.p. 147°–149° C., when recrystallized first from acetonitrile and then from methanol.

(b) 5-{7-[4-(4,5-Dihydro-2-oxazolyl)-3-methylphenoxy]heptyl}-3-methylisoxazole [IX; R=$CH_3$, $R_2$, $R_3$, $R_4$, $R_5$ and $R_6$=H, $R_1$=3-$CH_3$, Y=$(CH_2)_7$, oxazole at 4-position] was prepared from 4,5-dihydro-2-(4-hydroxy-2-methylphenyl)oxazole and 5-(7-bromoheptyl)-3-methylisoxazole according to the procedure of Example 9, part (d) and was obtained in 27% yield as a colorless solid, m.p. 58°–59° C. when recrystallized from an isopropyl acetate-hexane mixture.

EXAMPLE 39

5-{7-[4-(5-Chloromethyl-4,5-dihydro-2-oxazolyl)-phenoxy]heptyl}-3-methylisoxazole [IX; R=$CH_3$, $R_1$, $R_2$, $R_3$, $R_4$ and $R_5$=H, $R_6$=$CH_2Cl$, Y=$(CH_2)_7$, oxazole at 4-position] was prepared from 5-{7-[4-(4,5-dihydro-5-hydroxymethyl-2-oxazolyl)phenoxy]heptyl}-3-methylisoxazole (Example 23) and thionyl chloride, according to the procedure of Example 35, and was obtained in the form of a tan solid, m.p. 107°–109° C., when recrystallized from ethyl acetate.

EXAMPLE 40

5-{7-[4-(4,5-Dihydro-5-methoxymethyl-2-oxazolyl)-phenoxy[heptyl}-3-methylisoxazole [IX; R=$CH_3$, $R_1$, $R_2$, $R_3$, $R_4$ and $R_5$=H, $R_6$=$CH_2OCH_3$, Y=$(CH_2)_7$, oxazole at 4-position]

To a stirred suspension of 1.08 g of sodium hydride (60% in mineral oil) in 50 ml of dry tetrahydrofuran was added over 33 minutes a solution of 6.6 g of 5-{7-[4-(4,5-dihydro-5-hydroxymethyl-2-oxazolyl)phenoxy]heptyl}-3-methylisoxazole (Example 23). The mixture was heated at gentle reflux for one hour, then cooled to room temperature, and 4.30 g of methyl iodide in 25 ml of dry tetrahydrofuran was added over a 15 minute period. The reaction mixture was stirred overnight at room temperature, then filtered and concentrated in vacuo. The residue was washed with n-pentane and dissolved in ethyl acetate and the soluble portion isolated (6.31 g, m.p. 53°–55° C.). The latter was recrystallized from hexane to give 5.1 g of 5-{7-[4-(4,5-dihydro-5-methoxymethyl-2-oxazolyl)phenoxy]heptyl}-3-methylisoxazole, m.p. 60°–61° C.

EXAMPLE 41

(a) 4,5-Dihydro-2-(4-hydroxy-3-methoxyphenyl)oxazole [XVI; $R_2$, $R_4'$, $R_5'$ and $R_6'$=H, $R_1$=3-$OCH_3$, OH at 4-position] was prepared by reacting methyl 4-hydroxy-3-methoxybenzoate and ethanolamine, and treating the resulting N-(2-hydroxyethyl)-4-hydroxy-3-methoxybenzamide with thionyl chloride according to the procedures of Example 9, parts (a) and (b), and was obtained in 48% yield in the form of a colorless solid, m.p. 184°–185° C. when recrystallized from methanol.

(b) 5-{7-[4-(4,5-Dihydro-2-oxazolyl)-2-methoxyphenoxy]heptyl}-3-methylisoxazole [IX; R=$CH_3$, $R_2$, $R_3$, $R_4$, $R_5$ and $R_6$=H, $R_1$=2-$OCH_3$, Y=$(CH_2)_7$, oxazole at 4-position] was prepared from 4,5-dihydro-2-(4-hydroxy-3-methoxyphenyl)oxazole and 5-(7-bromoheptyl)-3-methylisoxazole according to the procedure of Example 9, part (d), and was obtained in the form of colorless crystals, m.p. 71°–73° C. when recrystallized from a hexane-isopropyl acetate mixture.

EXAMPLE 42

5-{5-[4-(4,5-Dihydro-2-oxazolyl)-2-methoxyphenoxy]pentyl}-3-methylisoxazole [IX; R=$CH_3$, $R_2$, $R_3$, $R_4$, $R_5$ and $R_6$=H, $R_1$=2-$OCH_3$, Y=$(CH_2)_5$, oxazole at 4-position] was prepared from 4,5-dihydro-2-(4-hydroxy-3-methoxyphenyl)oxazole (Example 41a) and 5-(5-bromopentyl)-3-methylisoxazole according to the procedure of Example 9, part (d), and was obtained in the form of a colorless solid, m.p. 97°–99° C., when recrystallized from isopropyl acetate.

It is further contemplated that by carrying out the procedures of Example 9 but replacing the methyl 4-hydroxybenzoate in part (a) of that example by a molar equivalent amount of methyl 3-nitro-4-hydroxybenzoate, methyl 3-methylthio-4-hydroxybenzoate, or methyl 3-trifluoromethyl-4-hydroxybenzoate, there can be obtained, respectively, 5-{7-[4-(4,5-dihydro-2-oxazolyl)-2-nitrophenoxy]heptyl}-3-methylisoxazole [IX; R=$CH_3$, $R_2$, $R_3$, $R_4$, $R_5$ and $R_6$=H, $R_1$=2-$NO_2$, Y=$(CH_2)_7$, oxazole at 4-position]; 5-{7-[4-(4,5-dihydro-2-oxazolyl)-2-methylthiophenoxy]heptyl}-3-methylisoxazole [IX; R=$CH_3$, $R_2$, $R_3$, $R_4$, $R_5$ and $R_6$=H, $R_1$=2-$SCH_3$, Y=$(CH_2)_7$, oxazole at 4-position]; or 5-{7-[4-(4,5-dihydro-2-oxazolyl)-2-trifluoromethylphenoxy]heptyl}-3-methylisoxazole [IX; R=$CH_3$, $R_2$, $R_3$, $R_4$, $R_5$ and $R_6$=H, $R_1$=2-$CF_3$, Y=$(CH_2)_7$, oxazole at 4-position].

According to the procedures described in the foregoing examples, the compounds of the following Examples (43–83) were prepared:

EXAMPLE 43

5-{7-[2-Chloro-4-(4,5-dihydro-2-oxazolyl)phenoxy]-heptyl}-3-methyl-4-isoxazolemethanol [IX; R=$CH_3$, $R_1$=2-Cl, $R_3$=$CH_2OH$, $R_2$, $R_4$, $R_5$ and $R_6$=H, Y=$(CH_2)_7$, oxazole at 4-position], m.p. 71°–73° C. (from hexane-isopropyl acetate).

Intermediates: 2-[4-(6-bromohexyloxy)-3-chlorophenyl]-4,5-dihydrooxazole, m.p. 60°–61° C. (colorless needles from hexane-isopropyl acetate); 3,5-dimethyl-4-isoxazolemethanol, m.p. 70°–73° C. (Example 29a).

EXAMPLE 44

5-{5-[2-Bromo-4-(4,5-dihydro-2-oxazolyl)phenoxy]-pentyl}-3-methylisoxazole [IX; R=$CH_3$, $R_1$=2-Br, $R_2$, $R_3$, $R_4$, $R_5$ and $R_6$=H, Y=$(CH_2)_5$, oxazole at 4-position], m.p. 123°–124° C. (from acetonitrile).

Intermediates: 5-(5-bromopentyl)-3-methylisoxazole, and 2-bromo-4-(4,5-dihydro-2-oxazolyl)phenol, m.p. 200°–201° C. (from tetrahydrofuran).

EXAMPLE 45

5-{7-[2-Bromo-4-(4,5-dihydro-2-oxazolyl)phenoxy]-heptyl}-3-methylisoxazole [IX; R=$CH_3$, $R_1$=2-Br, $R_2$, $R_3$, $R_4$, $R_5$ and $R_6$=H, Y=$(CH_2)_7$, oxazole at 4-position], m.p. 131°–132° C. (from tetrahydrofuran).

Intermediates: 5-(7-bromoheptyl)-3-methylisoxazole, and 2-bromo-4-(4,5-dihydro-2-oxazolyl)phenol.

EXAMPLE 46

5-{5-[4-(4,5-Dihydro-2-oxazolyl)-2-methylphenoxy]-pentyl}-3-methylisoxazole [IX; R=$CH_3$, $R_1$=2-$CH_3$, R$_2$, R$_3$, R$_4$, R$_5$ and R$_6$=H, Y=(CH$_2$)$_5$, oxazole at 4-position], m.p. 90°-91° C. (from n-hexane).

Intermediates: 5-(5-bromopentyl)-3-methylisoxazole, and 4-(4,5-dihydro-2-oxazolyl)-2-methylphenol (Example 31a).

EXAMPLE 47

5-{5-[3-chloro-4-(4,5-dihydro-2-oxazolyl)phenoxy]pentyl}-3-methylisoxazole [IX; R=CH$_3$, R$_1$=3-Cl, R$_2$, R$_3$, R$_4$, R$_5$ and R$_6$=H, Y=(CH$_2$)$_5$, oxazole at 4-position], m.p. 73°-74° C. (from isopropyl acetate-hexane).

Intermediates: 5-(5-bromopentyl)-3-methylisoxazole, and 4-(4,5-dihydro-2-oxazolyl)-3-chlorophenol (Example 13b).

EXAMPLE 48

5-{6-[2-Chloro-4-(4,5-dihydro-4-methyl-2-oxazolyl)phenoxy]hexyl}-3-methylisoxazole [IX; R=CH$_3$, R$_1$=2-Cl, R$_2$, R$_3$, R$_4$, R$_5$ and R$_6$=H, Y=(CH$_2$)$_6$, oxazole at 4-position], colorless viscous oil obtained by chromatography.

Intermediates: 5-(6-bromohexyl)-3-methylisoxazole, and 2-chloro-4-(4,5-dihydro-4-methyl-2-oxazolyl)phenol (Example 17a).

EXAMPLE 49

5-{5-[2-Amino-4-(4,5-dihydro-2-oxazolyl)phenoxy]pentyl}-3-methylisoxazole [IX; R=CH$_3$, R$_1$=2-NH$_2$, R$_2$, R$_3$, R$_4$, R$_5$ and R$_6$=H, Y=(CH$_2$)$_5$, oxazole at 4-position], m.p. 131°-132° C. (from methanol-t-butyl methyl ether).

Intermediates: 5-(5-bromopentyl)-3-methylisoxazole, and 2-amino-4-(4,5-dihydro-2-oxazolyl)phenol.

EXAMPLE 50

5-{7-[3-Chloro-4-(4,5-dihydro-2-oxazolyl)phenoxy]heptyl}-3-methylisoxazole [IX; R=CH$_3$, R$_1$=3-Cl, R$_2$, R$_3$, R$_4$, R$_5$ and R$_6$=H, Y=(CH$_2$)$_7$, oxazole at 4-position], m.p. 57°-59° C. (colorless needles from hexane-isopropyl acetate).

Intermediates: 5-(7-bromoheptyl)-3-methylisoxazole, and 3-chloro-4-(4,5-dihydro-2-oxazolyl)phenol.

EXAMPLE 51

5-{5-[4-(4,5-Dihydro-2-oxazolyl)-3-methylphenoxy]pentyl}-3-methylisoxazole [IX; R=CH$_3$, R$_1$=3-CH$_3$, R$_2$, R$_3$, R$_4$, R$_5$ and R$_6$=H, Y=(CH$_2$)$_5$, oxazole at 4-position], m.p. 50°-51° C. (from hexane); monomethanesulfonate salt, m.p. 113°-114° C.

Intermediates: 5-(5-bromopentyl)-3-methylisoxazole, and 3-methyl-4-(4,5-dihydro-2-oxazolyl)phenol, m.p. 145°-146° C.

EXAMPLE 52

5-{5-[4-(4,5-Dihydro-2-oxazolyl)-3-hydroxyphenoxy]pentyl}-3-methylisoxazole [IX; R=CH$_3$, R$_1$=3-OH, R$_2$, R$_3$, R$_4$, R$_5$ and R$_6$=H, Y=(CH$_2$)$_5$, oxazole at 4-position], m.p. 95°-96° C. (from acetonitrile).

Intermediates: 5-(5-bromopentyl)-3-metyhylisoxazole, and 2-(2,4-dihydroxyphenyl)-4,5-dihydrooxazole, m.p. 196°-198° C. (from methanol).

EXAMPLE 53

5-{5-[4-(4,5-Dihydro-2-oxazolyl)-2-nitrophenoxy]pentyl}-3-methylisoxazole [IX; R=CH$_3$, R$_1$=2-NO$_2$, R$_2$, R$_3$, R$_4$, R$_5$ and R$_6$=H, Y=(CH$_2$)$_5$, oxazole at 4-position], m.p. 94°-95° C. (from hexane-isopropyl acetate).

Intermediates: 5-(5-bromopentyl)-3-methylisoxazole, and 4-(4,5-dihydro-2-oxazolyl)-2-nitrophenol, hydrochloride salt, m.p. 125°-126° C. (yellow needles from ethanol).

EXAMPLE 54

5-55 5-[4-(4,5-Dihdyro-2-oxazolyl)-2-trifluoromethylphenoxy]pentyl]-3-methylisoxazole [IX; R=CH$_3$, R$_1$=2-CF$_3$, R$_2$, R$_3$, R$_4$, R$_5$ and R$_6$=H, Y=(CH$_2$)$_5$, oxazole at 4-position], m.p. 85°-85.5° C. (from triethylamine).

Intermediates: 5-(4-cyano-2-trifluoromethylphenoxy)pentyl-3-methylisoxazole, m.p. 93°-95° C. (from methyl t-butyl ether), prepared from 4-cyano-2-trifluoromethylphenol and 5-(5-bromopentyl)-3-methylisoxazole.

EXAMPLE 55

5-{5-[4-(4,5-Dihydro-2-oxazolyl)phenoxy]-3-pentenyl}-b 3-methylisoxazole [IX; R=CH$_3$, R$_1$, R$_2$, R$_3$, R$_4$, R$_5$ and R$_6$=H, Y=CH$_2$CH$_2$CH=CHCH$_2$, oxazole at 4-position], m.p. 108°-110° C. (from isopropyl acetate).

Intermediates: 3,5-dimethylisoxazole and 2-[4-(4-bromo-2-butenyloxy)phenyl]-4,5-dihydrooxazole, the latter in turn prepared from 4-(4,5-dihydro-2-oxazolyl)phenol and 1,4-dibromo-2-butene.

EXAMPLE 56

5-{5-[4-(4,5-Dihydro-4-methyl-2-oxazolyl)phenoxy]pentyl}-3-methylisoxazole [IX; R and R$_4$=CH$_3$, R$_1$, R$_2$, R$_3$, R$_5$ and R$_6$=H, Y=(CH$_2$)$_5$, oxazole at 4-position], m.p. 61°-62° C. (from hexane-methylene dichloride).

Intermediates: 5-[5-(4-cyanophenoxy)pentyl]-3-methylisoxazole (Example 2b) via the methyl iminoester hydrochloride (m.p. 164°-167° C.) and reaction with 2-amino-1-propanol.

EXAMPLE 57

5-{[2-Chloro-4-(4,5-dihydro-4,4-dimethyl-2-oxazolyl)phenoxy]pentyl}-3-methylisoxazole [IX; R, R$_4$ and R$_5$=CH$_3$, R$_1$=2-Cl, R$_2$, R$_3$ and R$_6$=H, Y=(CH$_2$)$_5$, oxazole at 4-position], m.p. 75°-76° C. (from n-hexane).

Intermediates: 5-[5-(2-chloro-4-chanophenoxy)pentyl]-3-methylisoxazole, m.p. 89.8°-90.5° C. (from 2-propanol) via the methyl imino-ester and reaction with 2-amino-2-methyl-1-propanol.

EXAMPLE 58

5-{5-[4-(4,5-Dihydro-2-oxazolyl)-2,6-dimethylphenoxy]pentyl}-3-methylisoxazole [IX; R=CH$_3$, R$_1$=2-CH$_3$, R$_2$=6-CH$_3$, R$_3$, R$_4$, R$_5$ and R$_6$=H, Y=(CH$_2$)$_5$, oxazole at 4-position], amber oil by chromatography, m.p. below room temperature; methanesulfonate salt, m.p. 114°-115° C.

Intermediates: 5-(5-bromopentyl)-3-methylisoxazole, and 4-(4,5-dihydro-2-oxazolyl)-2,6-dimethylphenol, hydrochloride salt, m.p. 208°-210° C. (from methanol).

EXAMPLE 59

5-{7-[4-(4,5-Dihydro-2-oxazolyl)-3-hydroxyphenoxy]heptyl}-3-methylisoxazole [IX; R=CH$_3$, R$_1$=3-OH, R$_2$, R$_3$, R$_4$, R$_5$ and R$_6$=H, Y=(CH$_2$)$_7$, oxazole at 4-position], m.p. 82°-83° C. (from carbon tetrachloride).

Intermediates: 5-(7-bromoheptyl)-3-methylisoxazole and 2-(2,4-dihydroxyphenyl)-4,5-dihydrooxazole.

EXAMPLE 60

5-{5-[4-(4,5-Dihydro-2-oxazolyl)-2-ethylphenoxy]pentyl}-3-methylisoxazole [IX; $R=CH_3$, $R_1=2\text{-}CH_2CH_3$, $R_2$, $R_3$, $R_4$, $R_5$ and $R_6=H$, $Y=(CH_2)_5$, oxazole at 4-position], m.p. 83°–85° C. (from methyl t-butyl ether).

Intermediates: 5-(5-bromopentyl)-3-methylisoxazole, and 4-(4,5-dihydro-2-oxazolyl)-2-ethylphenol, hydrochloride salt, m.p. 158°–159° C. (from methanol).

EXAMPLE 61

5-{5-[4-(4,5-Dihydro-2-oxazolyl)-2-(2-propenyl)phenoxy]pentyl}-3-methylisoxazole [IX; $R=CH_3$, $R_1=2\text{-}CH_2CH=CH_2$, $R_2$, $R_3$, $R_4$, $R_5$ and $R_6=H$, $Y=(CH_2)_5$, oxazole at 4-position], m.p. 68°–69° C. (from methyl t-butyl ether).

Intermediates: 5-(5-bromopentyl)-3-methylisoxazole and 4-(4,5-dihydro-2-oxazolyl)-2-(2-propenyl)phenol, m.p. 158°–159° C. (from methanol).

EXAMPLE 62

5-{5-[4-(4,5-Dihydro-4,4-dimethyl-2-oxazolyl)phenoxy]pentyl}-3-methylisoxazole [IX; R, $R_4$ and $R_5=CH_3$, $R_1$, $R_2$, $R_3$ and $R_6=H$, $Y=(CH_2)_5$, oxazole at 4-position], m.p. 50°–50.5° C.

Intermediates: 5-[5-(4-cyanophenoxy)pentyl]-3-methylisoxazole (Example 2a) via methyl imino-ester and reaction with 2-amino-2-methyl-1-propanol.

EXAMPLE 63

5-{5-[4-(4,5-Dihydro-2-oxazolyl)-2-acetylphenoxy]pentyl}-3-methylisoxazole [IX; $R=CH_3$, $R_1=2\text{-}COCH_3$, $R_2$, $R_3$, $R_4$, $R_5$ and $R_6=H$, $Y=(CH_2)_5$, oxazole at 4-position], m.p. 117°–118° C. (from methanol).

Intermediates: 5-(5-bromopentyl)-3-methylisoxazole, and 2-acetyl-4-(4,5-dihydro-2-oxazolyl)phenol, yellow solid, m.p. 134°–136° C. (from hexane-isopropyl acetate).

EXAMPLE 64

5-{4-[4-(4,5-Dihydro-4-methyl-2-oxazolyl)phenoxy]butyl}-3-methylisoxazole [IX; R and $R_4=CH_3$, $R_1$, $R_2$, $R_3$, $R_5$ and $R_6=H$, $Y=(CH_2)_4$, oxazole at 4-position], m.p. 60°–60.5° C. (from n-hexane).

Intermediates: 5-[4-(4-cyanophenoxy)butyl]-3-methylisoxazole, m.p. 57°–58° C. (from 2-propanol), via methyl imino-ester hydrochloride and reaction with 2-amino-1-propanol.

EXAMPLE 65

5-{4-[2-Chloro-4-(4,5-dihydro-4-methyl-2-oxazolyl)phenoxy]butyl}-3-methylisoxazole [IX; R and $R_4=CH_3$, $R_1=2\text{-}Cl$, $R_2$, $R_3$, $R_5$ and $R_6=H$, $Y=(CH_2)_4$, oxazole at 4-position], m.p. 47.5°–49° C.

Intermediates: 5-[4-(2-chloro-4-cyanophenoxy)butyl]-3-methhylisoxazole, m.p. 82°–83° C. (from 2-propanol), via methyl imino-ester hydrochloride and reaction with 2-amino-1-propanol.

EXAMPLE 66

5-{4-[2-Chloro-4-(4,5-dihydro-4,4-dimethyl-2-oxazolyl)phenoxy]butyl}-3-methylisoxazole [IX; R, $R_4$ and $R_5=CH_3$, $R_1=2\text{-}Cl$, $R_2$, $R_3$ and $R_6=H$, $Y=(CH_2)_4$, oxazole at 4-position], m.p. 63°–64° C.

Intermediates: 5-[4-(2-chloro-4-cyanophenoxy)butyl]-3-methylisoxazole, via the methyl imino-ester hydrochloride and reaction with 2-amino-2-methyl-1-propanol.

EXAMPLE 67

5-{4-[4-(4,5-Dihydro-4,4-dimethyl-2-oxazolyl)phenoxy]butyl}-3-methylisoxazole [IX; R, $R_4$ and $R_5=CH_3$, $R_1$, $R_2$, $R_3$ and $R_6=H$, $Y=(CH_2)_4$, oxazole at 4-position], m.p. 61.5°–62° C.

Intermediates: 5-[4-(4-cyanophenoxy)butyl]-3-methylisoxazole, via the methyl imino-ester hydrochloride and reaction with 2-amino-2-methyl-1-propanol.

EXAMPLE 68

5-{5-[2-Chloro-4-(4,5-dihydro-2-oxazolyl)phenoxy]-3-pentenyl}-3-methylisoxazole [IX; $R=CH_3$, $R_2=2\text{-}Cl$, $R_2$, $R_3$, $R_4$, $R_5$ and $R_6=H$, $Y=CH_2CH_2CH=CHCH_2$, oxazole at 4-position], m.p. 107°–108° C. (needles from triethylamine).

Intermediates: 3,5-dimethylisoxazole and 2-[4-(4-bromo-2-butenyloxy)-3-chlorophenyl]-4,5-dihydrooxazole, the latter in turn prepared from 2-chloro-4-(4,5-dihydro-2-oxazolyl)phenol and 1,4-dibromo-2-butene.

EXAMPLE 69

5-{7-[4-(4,5-Dihydro-2-oxazolyl)-2-formylphenoxy]heptyl}-3-methylisoxazole [IX; $R=CH_3$, $R_1=2\text{-}CHO$, $R_2$, $R_3$, $R_4$, $R_5$ and $R_6=H$, $Y=(CH_2)_7$, oxazole at 4-position], m.p. 72°–73° C. (from isopropyl acetate).

Intermediates: 5-(7-bromoheptyl)-3-methylisoxazole, and 4-(4,5-dihydro-2-oxazolyl)-2-formylphenol, hydrochloride salt, m.p. 111°–112° C.

EXAMPLE 70

5-{5-[4-(4,5-Dihydro-2-oxazolyl)-2-formylphenoxy]pentyl}-3-methylisoxazole [IX; $R=CH_3$, $R_1=2\text{-}CHO$, $R_2$, $R_3$, $R_4$, $R_5$ and $R_6=H$, $Y=(CH_2)_5$, oxazole at 4-position], m.p. 103°–104° C. (from ethyl acetate).

Intermediates: 5-(5-bromopentyl)-3-methylisoxazole, and 4-(4,5-dihydro-2-oxazolyl)-2-formylphenol.

EXAMPLE 71

5-{5-[4-(4,5-Dihydro-2-oxazolyl)-2-(1-methylethyl)phenoxy]pentyl}-3-methylisoxazole [IX; $R=CH_3$, $R_1=2\text{-}(CH_3)_2CH$, $R_2$, $R_3$, $R_4$, $R_5$ and $R_6=H$, $Y=(CH_2)_5$, oxazole at 4-position], m.p. 69°–71° C. (from hexane).

Intermediates: 5-(5-bromopentyl)-3-methylisoxazole, and 4-(4,5-dihydro-2-oxazolyl)-2-(1-methylethyl)phenol, m.p. 195°–196° C. (from ethanol).

EXAMPLE 72

5-{5-[2,3-Dichloro-4-(4,5-dihydro-2-oxazolyl)phenoxy]pentyl}-3-methylisoxazole [IX; $R=CH_3$, $R_1=2\text{-}Cl$, $R_2=3\text{-}Cl$, $R_3$, $R_4$, $R_5$ and $R_6=H$, $Y=(CH_2)_5$, oxazole at 4-position], m.p. 109°–110° C. (from triethylamine).

Intermediates: 5-(5-bromopentyl)-3-methylisoxazole, and 2,3-dichloro-4-(4,5-dihydro-2-oxazolyl)phenol.

EXAMPLE 73

5-{3-[[2-[4-(4,5-Dihydro-2-oxazolyl)phenoxy]ethoxy]methoxy]propyl}-3-methylisoxazole [IX; $R=CH_3$, $R_1$, $R_2$, $R_3$, $R_4$, $R_5$ and $R_6=H$, $Y=(CH_2)_3OCH_2O(CH_2)_2$, oxazole at 4-position], buff-colored solid, m.p. 43°–44° C.

Intermediates: 4-(4,5-dihydro-2-oxazolyl)phenol, and 5-(chloroethoxymethoxypropyl)-3-methylisoxazole, $n_D^{22} = 1.4735$, in turn prepared from 3,5-dimethylisoxazole and bis(2-chloroethoxy)methane.

EXAMPLE 74

5-{5-[2,6-Dibromo-4-(4,5-dihydro-2-oxazolyl)phenoxy]pentyl}-3-methylisoxazole [IX; $R = CH_3$, $R_1 = 2$-Br, $R_2 = 6$-Br, $R_3$, $R_4$, $R_5$ and $R_6 = H$, $Y = (CH_2)_5$, oxazole at 4-position], light yellow oil by chromatography, Intermediates: 5-(5-bromopentyl)-3-methylisoxazole, and 2,6-dibromo-4-(4,5-dihydro-2-oxazolyl)phenol hydrochloride, in turn prepared from 3,5-dibromo-4-hydroxy-N-(2-hydroxyethyl)benzamide, m.p. 172°-173° C.

EXAMPLE 75

5-{5-[4-(4,5-Dihydro-5-hydroxymethyl-2-oxazolyl)phenoxy]pentyl}-3-methylisoxazole [IX; $R = CH_3$, $R_6 = CH_2OH$, $R_1$, $R_2$, $R_3$, $R_4$ and $R_5 = H$, $Y = (CH_2)_5$, oxazole at 4-position], m.p. 82°-84° C. (from acetonitrile).

Intermediates: 5-[5-(4-cyanophenoxy)pentyl]-3-methylisoxazole, via methyl imino-ester hydrochloride and reaction with 3-amino-1,2-propanediol.

EXAMPLE 76

5-{5-[4-(4,5-Dihydro-2-oxazolyl)-2-(1,1-dimethylethyl)phenoxy]pentyl}-3-methylisoxazole [IX; $R = CH_3$, $R_1 = 2$-C(CH_3)_3, $R_2$, $R_3$, $R_4$, $R_5$ and $R_6 = H$, $Y = (CH_2)_5$, oxazole at 4-position], m.p. 103°-104° C. (from ethyl acetate).

Intermediates: 5-(5-bromopentyl)-3-methylisoxazole, and 4-(4,5-dihydro-2-oxazolyl)-2-(1,1-dimethylethyl)phenol.

EXAMPLE 77

5-{5-[3-Chloro-4-(4,5-dihydro-4-methyl-2-oxazolyl)phenoxy]pentyl}-3-methylisoxazole [IX; R and $R_4 = CH_3$, $R_1 = 3$-Cl, $R_2$, $R_3$, $R_5$ and $R_6 = H$, $Y = (CH_2)_5$, oxazole at 4-position], m.p. 48°-50° C. (from methyl t-butyl ether).

Intermediates: 5-(5-bromopentyl)-3-methylisoxazole, and 3-chloro-4-(4,5-dihydro-4-methyl-2-oxazolyl)phenol, m.p. 140°-142° C. (from acetonitrile). The latter in turn was prepared from 2-chloro-4-hydroxy-N-(2-hydroxy-1-methylethyl)benzamide, m.p. 139°-140° C. (from acetonitrile).

EXAMPLE 78

5-{5-[2-Chloro-4-(4,5-dihydro-2-oxazolyl)-6-(1,1-dimethylethyl)phenoxy]pentyl}-3-methylisoxazole [IX; $R = CH_3$, $R_1 = 2$-Cl, $R_2 = 6$-C(CH_3)_3, $R_3$, $R_4$, $R_5$ and $R_6 = H$, $Y = (CH_2)_5$, oxazole at 4-position], monomethanesulfonate salt, m.p. 98°-100° C. (from acetone).

Intermediates: 5-(5-bromopentyl)-3-methylisoxazole, and 2-chloro-4-(4,5-dihydro-2-oxazolyl)-6-(1,1-dimethylethyl)phenol.

EXAMPLE 79

5-{5-[4-(4,5-Dihydro-2-oxazolyl)-2,3-dimethylphenoxy]pentyl}-3-methylisoxazole [IX; $R = CH_3$, $R_1 = 2$-CH_3, $R_2 = 3$-CH_3, $R_3$, $R_4$, $R_5$ and $R_6 = H$, $Y = (CH_2)_5$, oxazole at 4-position], m.p. 76°-77° C. (from methyl t-butyl ether).

Intermediates: 5-(5-bromopentyl)-3-methylisoxazole, and 4-(4,5-dihydro-2-oxazolyl)-2,3-dimethylphenol, m.p. 160°-162° C. (from acetonitrile).

EXAMPLE 80

5-{5-[4-(4,5-Dihydro-2-oxazolyl)-3-hydroxy-2-methylphenoxy]pentyl}-3-methylisoxazole [IX; $R = CH_3$, $R_1 = 2$-CH_3, $R_2 = 3$-OH, $R_3$, $R_4$, $R_5$ and $R_6 = H$, $Y = (CH_2)_5$, oxazole at 4-position], m.p. 110°-111° C. (from acetonitrile).

Intermediates: 5-(5-bromopentyl)-3-methylisoxazole, and 4-(4,5-dihydro-2-oxazolyl)-3-hydroxy-2-methylphenol, m.p. 174°-177° C.

EXAMPLE 81

5-{5-[4-(4,5-Dihydro-2-oxazolyl)-2,6-bis(1,1-dimethylethyl)phenoxy]pentyl}-3-methylisoxazole [IX; $R = CH_3$, $R_1 = 2$-C(CH_3)_3, $R_2 = 6$-C(CH_3)_3, $R_3$, $R_4$, $R_5$ and $R_6 = H$, $Y = (CH_2)_5$, oxazole at 4-position], red viscous oil by chromatography.

Intermediates: 5-(5-bromopentyl)-3-methylisoxazole, and 4-(4,5-dihydro-2-oxazolyl)-2,6-bis(1,1-dimethylethyl)phenol, m.p. 178°-179° C.

EXAMPLE 82

5-{3-[[2-[2-Chloro-4-(4,5-dihydro-2-oxazolyl)phenoxy]ethoxy]methoxy]propyl}-3-methylisoxazole [IX; $R = CH_3$, $R_1 = 2$-Cl, $R_2$, $R_3$, $R_4$, $R_5$ and $R_6 = H$, $Y = (CH_2)_3OCH_2O(CH_2)_2$, oxazole at 4-position], m.p. 48.5°-49° C.

Intermediates: 2-chloro-4-(4,5-dihydro-2-oxazolyl)phenol, and 5-(chloroethoxymethoxypropyl)-3-methylisoxazole.

EXAMPLE 83

5-{3-[[2-[4-(4,5-dihydro-2-oxazolyl)-2-methylphenoxy]ethoxy]methoxy]propyl}-3-methylisoxazole [IX; $R = CH_3$, $R_1 = 2$-CH_3, $R_2$, $R_3$, $R_4$, $R_5$ and $R_6 = H$, $Y = (CH_2)_3OCH_2O(CH_2)_2$, oxazole at 4-position], m.p. 56°-56.5° C.

Intermediates: 4-(4,5-dihydro-2-oxazolyl)phenol, and 5-(chloroethoxymethoxypropyl)-3-methylisoxazole.

EXAMPLE 84

5-{5-[2-Difluoromethyl-4-(4,5-dihydro-2-oxazolyl)phenoxy]pentyl}-3-methylisoxazole [IX; $R = CH_3$, $R_1 = 2$-CHF_2, $R_2$, $R_3$, $R_4$, $R_5$ and $R_6 = H$, $Y = (CH_2)_5$, oxazole at 4-position].

To a solution of 1.61 g of diethylaminosulfur trifluoride in 10 ml of methylene dichloride was added dropwise 3.42 g of 5-{5-[4-(4,5-dihydro-2-oxazolyl)-2-formylphenoxy]pentyl}-3-methylisoxazole (Example 70) in 5 ml of methylene dichloride. The mixture was stirred for about 24 hours, then diluted with methylene dichloride to 50 ml and extracted with water and saturated sodium chloride solution. The organic layer was dried over anhydrous sodium sulfate and the solvent removed. The residue was purified by chromatography and recrystallized from isopropyl acetate to give 1 g of 5-{5-[2-difluoromethyl-4-(4,5-dihydro-2-oxazolyl)phenoxy]pentyl}-3-methylisoxazole, m.p. 80°-89° C.

EXAMPLE 85

5-{5-[4-(4,5-Dihydro-2-oxazolyl)-2-hydroxymethylphenoxy]pentyl}-3-methylisoxazole [IX; $R = CH_3$, $R_1 = 2$-CH_2OH, $R_2$, $R_3$, $R_4$, $R_5$ and $R_6 = H$, $Y = (CH_2)_5$, oxazole at 4-position].

To a solution of 1.2 g of 5-{5-[4-(4,5-dihydro-2-oxazolyl)-2-formylphenoxy]pentyl}-3-methylisoxazole (Example 70) in 10 ml of methanol was added in portions 0.2 g of sodium borohydride. The mixture was stirred for one hour, then treated with a few drops of glacial acetic acid and diluted to 50 ml with water. The solid product was collected, washed with aqueous methanol and recrystallized from ethyl acetate to give 1.2 g of 5-{5-[4-(4,5-dihydro-2-oxazolyl)-2-hydroxymethylphenoxy]pentyl}-3-methylisoxazole, m.p. 140°–141° C.

EXAMPLE 86

5-{5-[2-Carboxy-4-(4,5-dihydro-2-oxazolyl)phenoxy]pentyl}-3-methylisoxazole [IX; R=CH$_3$, R$_1$=2-COOH, R$_2$, R$_3$, R$_4$, R$_5$ and R$_6$=H, Y=(CH$_2$)$_5$, oxazole at 4-position].

A solution of 4.7 g of silver nitrate in 6 ml of distilled water was added to a stirred suspension of 4.0 g of 5-{5-[4-(4,5-dihydro-2-oxazolyl)-2-formylphenoxy]pentyl}-3-methylisoxazole (Example 70) in 60 ml of ethanol. The mixture was stirred for about two minutes, and then a solution of 8.4 g of potassium hydroxide in 140 ml of water was slowly added. The latter mixture was stirred for two hours, then filtered and the filtrate acidified. The solid product was collected, washed with dilute hydrochloric acid, dried and recrystallized from methanol to give 1.6 g of 5-{5-[2-carboxy-4-(4,5-dihydro-2-oxazolyl)phenoxy]pentyl}-3-methylisoxazole, m.p. 170°–171° C.

EXAMPLE 87

(a) 4-(2-Oxazolyl)phenol 2-(4-Aminophenyl)oxazole [m.p. 121°–123° C.; Rosenbaum et al., J. Am. Chem. Soc. 64, 2444 (1942)] (10.3 g) was diazotized with 4.93 g of sodium nitrite and 215 ml of 2N sulfuric acid. The resulting diazonium salt was heated until no more nitrogen was evolved, and the product was isolated and recrystallized from ethylene dichloride to give 4.96 g of 4-(2-oxazolyl)phenol, yellow crystals, m.p. 167°–168° C.

(b) 3-Methyl-5-{7-[4-(2-oxazolyl)phenoxy]heptyl}isoxazole [I; Het=4-(2-oxazolyl), R=CH$_3$, R$_1$, R$_2$ and R$_3$=H, X=O, Y=(CH$_2$)$_7$] was prepared from 5.43 g of 4-(2-oxazolyl)phenol and 8.77 g of 5-(7-bromoheptyl)-3-methylisoxazole according to the procedure of Example 9, part (d), and was obtained in 21% yield as a colorless solid, m.p. 71°–73° C. (from hexane-methyl t-butyl ether).

EXAMPLE 88

3-Methyl-5-{5-[4-(2-oxazolyl)phenoxy]pentyl}isoxazole [I; Het=4-(2-oxazolyl), R=CH$_3$, R$_1$, R$_2$ and R$_3$=H, X=O, Y=(CH$_2$)$_5$], m.p. 90°–91° C. (from methyl t-butyl ether), was prepared by a procedure analogous to that of Example 87. A sample of the compound was converted to its monomethanesulfonate salt, m.p. 114°–116° C.

EXAMPLE 89

(a) 2-(4-Methoxyphenyl)-4,5-dimethyloxazole N-oxide hydrochloride

A mixture of 68.07 g of anisaldehyde, 50.5 g of 2,3-butanedione mono-oxime and 150 ml of acetic acid was saturated with hydrogen chloride gas and the mixture was allowed to stand at room temperature for 3 hours. The solid product was collected and recrystallized from methanol to give 2-(4-methoxyphenyl)-4,5-dimethyloxazole N-oxide hydrochloride, m.p. 194°–196° C. The latter was converted to the free base for use in the next reaction by treatment with sodium bicarbonate solution.

(b) 2-(4-Methoxyphenyl)-4,5-dimethyloxazole

Zinc dust (325 mesh, 60 g) was added in portions over 15 minutes to a solution of 43.8 g of 2-(4-methoxyphenyl)-4,5-dimethyloxazole N-oxide in 400 ml of acetic acid, stirred and heated on a steam bath. After an additional 15 minutes of heating, the reaction mixture was filtered and concentrated in vacuo. The residue was stirred with concentrated ammonium hydroxide and ethyl acetate. The layers were separated, the aqueous layer extracted with ethyl acetate, and the combined ethyl acetate solutions dried and concentrated to yield 32.6 g of 2-(4-methoxyphenyl)-4,5-dimethyloxazole as a yellow oil.

(c) 4-(4,5-Dimethyl-2-oxazolyl)phenol

A mixture of 32.0 g of 2-(4-methoxyphenyl)-4,5-dimethyloxazole and 250 ml of 48% hydrogen bromide solution was stirred and heated at reflux for 2.5 hours. The reaction mixture was concentrated in vacuo, the residue dissolved in 2N sodium hydroxide and the solution acidified with acetic acid. The solid product was collected and recrystallized from methanol to give 24.3 g of 4-(4,5-dimethyl-2-oxazolyl)phenol, m.p. 202°–203° C.

(d) 5-{5-[4-(4,5-Dimethyl-2-oxazolyl)phenoxy]pentyl}-3-methylisoxazole [I; Het=4-(4,5-dimethyl-2-oxazolyl), R=CH$_3$, R$_1$, R$_2$ and R$_3$=H, X=O, Y=(CH$_2$)$_5$], m.p. 88°–90° C. (from triethylamine) was prepared in 73% yield from 6.47 g of 4-(4,5-dimethyl-2-oxazolyl)phenol, 7.9 g of 5-(5-bromopentyl)-3-methylisoxazole, 8 g of potassium carbonate and 1 g of potassium iodide in 50 ml of dimethylformamide, heated 6 hours at 100° C.

EXAMPLE 90

5-{5-[4-(4,5-Dimethyl-2-oxazolyl)-2-methylphenoxy]pentyl}-3-methylisoxazole [I; Het=4-(4,5-dimethyl-2-oxazolyl), R=CH$_3$, R$_1$=2-CH$_3$, R$_2$ and R$_3$=H, X=O, Y=(CH$_2$)$_5$], m.p. 71°–72° C. (from triethylamine), was prepared in 59% yield in accordance with the procedure of Example 89.

Intermediates: 5-(5-bromopentyl)-3-methylisoxazole, and 4-(4,5-dimethyl-2-oxazolyl)-2-methylphenol, m.p. 224°–225° C. (from tetrahydrofuran). The latter was in turn prepared from 3-methyl-4-methoxybenzaldehyde according to the procedures of Example 89, parts (a)–(c).

EXAMPLE 91

5-{5-[4-(4,5-Dimethyl-2-oxazolyl)-2-trifluoromethylphenoxy]pentyl}-3-methylisoxazole [I; Het=4-(4,5-dimethyl-2-oxazolyl), R=CH$_3$, R$_1$=2-CF$_3$, R$_2$ and R$_3$=H, X=O, Y=(CH$_2$)$_5$], m.p. 79°–80° C. (from cyclohexane), was prepared in 54% yield in accordance with the procedure of Example 89.

Intermediates: 5-(5-bromopentyl)-3-methylisoxazole, and 4-(4,5-dimethyl-2-oxazolyl)-2-trifluoromethylphenol, m.p. 210°–213° C. (from acetonitrile). The latter was in turn prepared from 4-methoxy-3-trifluoromethylbenzaldehyde via 2-(4-methoxy-3-trifluoromethylphenyl)-4,5-dimethyloxazole N-oxide, m.p. 159.5°–160° C. (from ethanol).

EXAMPLE 92

5-{5-[2-Bromo-4-(2-oxazolyl)phenoxy]pentyl}-3-methylisoxazole [I; Het=4-(2-oxazolyl), R=CH$_3$, R$_1$=2-Br, R$_2$ and R$_3$=H, X=O, Y=(CH$_2$)$_5$], m.p. 89°–90° C. (from methyl t-butyl ether); yield 58.5%.

Intermediates: 5-(5-bromopentyl)-3-methylisoxazole, and 4-(2-oxazolyl)-2-bromophenol, m.p. 130°–135° C. (from acetonitrile). The latter was prepared by bromination of 4-(2-oxazolyl)phenol (Example 87a) with bromine in acetic acid solution.

EXAMPLE 93

(a) 2-(4-Methoxyphenyl)-4-carbethoxy-5-methyloxazole N-oxide hydrochloride was prepared in 67% yield from anisaldehyde and ethyl 2-oximino-3-oxobutanoate according to the procedure of Example 89, part (a). The crude product was used directly in the next reaction.

(b) 2-(4-Methoxyphenyl)-4-carbethoxy-5-methyloxazole was prepared in 61% yield by zinc dust reduction of the compound of part (a) in accordance with the procedure of Example 89, part (b), and obtained as a crystalline material, m.p. 74°–76° C. (from methyl t-butyl ether).

(c) 2-(4-Methoxyphenyl)-4-carboxy-5-methyloxazole was prepared in 80% yield by hydrolysis of the ethyl ester of part (b) with concentrated hydrochloric acid, refluxed 4.5 hours. The isolated solid product was used directly in the next reaction.

(d) 2-(4-Methoxyphenyl)-5-methyloxazole was prepared in 35.5% yield of decarboxylation of the compound of part (c) with copper powder in Dowtherm at reflux temperature. The isolated product was distilled, b.p. 136°–140° C. (0.1 mm).

(e) 4-(5-Methyl-2-oxazolyl)phenol was prepared by demethylation of the compound of part (d) with hydrobromic acid, 6.5 hours at reflux, and was obtained as a crystalline solid, m.p. 177°–178° C.

(f) 3-Methyl-5-{5-[4-(5-methyl-2-oxazolyl)phenoxy]pentyl}isoxazole [I; Het=4-(5-methyl-2-oxazolyl), R=CH$_3$, R$_1$, R$_2$ and R$_3$=H, X=O, Y=(CH$_2$)$_5$], m.p. 90°–91° C. (from methyl t-butyl ether), was prepared in 50% yield from 5-(5-bromopentyl)-3-methylisoxazole and 4-(5-methyl-2-oxazolyl)phenol.

EXAMPLE 94

(a) N-(3-Hydroxypropyl)-4-hydroxybenzamide

A mixture of 76 g of methyl 4-hydroxybenzoate and 112.5 g of 3-amino-1-propanol was heated and stirred at 120° C. for 8 hours. The reaction mixture was acidified with 2N hydrochloric acid and then extracted with ethyl acetate and butanol. The combined extracts were concentrated in vacuo and the residue was recrystallized from acetonitrile to give 37.8 g of N-(3-hydroxypropyl)-4-hydroxybenzamide, m.p. 118°–120° C.

(b) 4-(5,6-Dihydro-4H-1,3-oxazin-2-yl)phenol

A mixture of 37.8 g of N-(3-hydroxypropyl)-4-hydroxybenzamide and 100 ml of thionyl chloride was stirred for 1.5 hours. The reaction mixture was concentrated in vacuo, the solid residue triturated with ethyl acetate, and converted to the free base by treatment with ammonium hydroxide. There was obtained 10.2 g of 4-(5,6-dihydro-4H-1,3-oxazin-2-yl)phenol, m.p. 196°–198° C. (from methanol).

(c) 5,6-Dihydro-2-{4-[7-(3-methyl-5-isoxazolyl)heptyloxy]phenyl}-4H-1,3-oxazine [I; Het=4-(5,6-dihydro-4H-1,3-oxazin-2-yl), R=CH$_3$, R$_1$, R$_2$ and R$_3$=H, X=O, Y=(CH$_2$)$_7$] was prepared from 7.1 g of 4-(5,6-dihydro-4H-1,3-oxazin-2-yl)phenol and 9.25 g of 5-(7-bromopentyl)-3-methylisoxazole according to the procedure of Example 9, part (d): yield 3.2 g, m.p. 88°–89° C. (from methyl t-butyl ether).

EXAMPLE 95

5,6-Dihydro-2-{4-[5-(3-methyl-5-isoxazolyl)pentyloxy]phenyl}-4H-1,3-oxazine [I; Het=4-(5,6-dihydro-4H-1,3-oxazin-2-yl), R=CH$_3$, R$_1$, R$_2$ and R$_3$=H, X=O, Y=(CH$_2$)$_5$], m.p. 80°–81° C. (from triethylamine) was prepared from 4-(5,6-dihydro-4H-1,3-oxazin-2-yl)phenol (Example 94b) and 5-(5-bromopentyl)-3-methylisoxazole.

EXAMPLE 96

(a) 4-[5-(3-Methyl-5-isoxazolyl)pentyloxy]benzaldehyde

A solution of 7.2 g of 4-hydroxybenzaldehyde, 14.6 g of 5-(5-bromopentyl)-3-methylisoxazole, 4 g of potassium hydroxide in 100 ml of acetonitrile was heated at reflux for 1.5 hours. The reaction mixture was cooled and filtered, the solvent removed, and the residue recrystallized from isopropyl acetate-hexane to give 10.8 g of 4-[5-(3-methyl-5-isoxazolyl)pentyloxy]benzaldehyde as a pale yellow powder.

(b) 3-Methyl-5-{5-[4-(5-oxazolyl)phenoxy]pentyl}isoxazole [I; Het=4-(5-oxazolyl), R=CH$_3$, R$_1$, R$_2$ and R$_3$=H, X=O, Y=(CH$_2$)$_5$].

A suspension of 10.00 g of 4-[5-(3-methyl-5-isoxazolyl)pentyloxy]benzaldehyde, 10.0 g of potassium carbonate and 7.14 g of tosylmethyl isocyanide (4-CH$_3$C$_6$H$_4$—SO$_2$CH$_2$NC) in 90 ml of methanol was heated at reflux for 3 hours. The reaction mixture was concentrated in vacuo, and the residue was extracted with methylene dichloride. The extract was washed with water, the product isolated and recrystallized from isopropyl acetate-hexane. Further purification by flash filtration through a silica gel pad, eluting with isopropyl acetate, and recrystallization from isopropyl acetate-hexane gave 5.43 g (48%) of 3-methyl-5-{5-[4-(5-oxazolyl)phenoxy]pentyl}isoxazole, yellow powder, m.p. 91°–93° C.

EXAMPLE 97

(a) 3,5-Dimethyl-4-[5-(3-methyl-5-isoxazolyl)pentyloxy]benzaldehyde was prepared from 3,5-dimethyl-4-hydroxybenzaldehyde and 5-(5-bromopentyl)-3-methylisoxazole according to the procedure of Example 96(a), and was obtained in 82% yield as a pale-orange solid, m.p. 51°–53° C. (from hexane-isopropyl acetate).

(b) 5-{5-[2,6-Dimethyl-4-(5-oxazolyl)phenoxy]pentyl}-3-methylisoxazole [I; Het=4-(5-oxazolyl), R=CH$_3$, R$_1$=2-CH$_3$, R$_2$=6-CH$_3$, R$_3$=H, X=O, Y=(CH$_2$)$_5$] was prepared from 3,5-dimethyl-4-[5-(3-methyl-5-isoxazolyl)pentyloxy]benzaldehyde and tosylmethyl isocyanide according to the procedure of Example 96(b), and was obtained in 69% yield as a pale yellow powder, m.p. 56°–58° C. (from isopropyl acetate-hexane).

EXAMPLE 98

5-{5-[2,6-Dichloro-4-(5-oxazolyl)phenoxy]pentyl}-3-methylisoxazole [I; Het=4-(5-oxazolyl), R=CH$_3$, R$_1$=2-Cl, R$_2$=6-Cl, R$_3$=H, X=O, Y=(CH$_2$)$_5$] was prepared from 3,5-dichloro-4-[5-(3-methyl-5-isoxazolyl)pentyloxy]benzaldehyde and tosylmethyl isocyanide according to the method of Example 96(b) and was obtained in 59% yield in the form of its methanesulfonate salt hemihydrate, m.p. 113°–115° C. (from 2-propanol).

The intermediate benzaldehyde was prepared from 3,5-dichloro-4-hydroxybenzaldehyde and 5-(5-bromopentyl)-3-methylisoxazole according to the procedure of Example 96(a).

EXAMPLE 99

5-{[[5-[4-(4,5-Dihydro-2-oxazolyl)phenoxy]pentyl]oxy]methyl}-3-methylisoxazole [IX; R=CH$_3$, R$_1$, R$_2$, R$_3$, R$_4$, R$_5$ and R$_6$=H, Y=CH$_2$O(CH$_2$)$_5$, oxazole at 4-position] was prepared from 3-methyl-5-isoxazolylmethanol and 5-[4-(4,5-dihydro-2-oxazolyl)phenoxy]pentyl iodide in the presence of either sodium hydride or lithium hydride in tetrahydrofuran solution. The product was purified by chromatography to give the above-indicated product as an off-white solid, m.p. 53°-54° C.

EXAMPLE 100

5-{5-[4-(4,5-Dihydro-2-oxazolyl)-2-(dimethylamino)phenoxy]pentyl}-3-methylisoxazole [IX; R=CH$_3$, R$_1$=2-N(CH$_3$)$_2$, R$_2$, R$_3$, R$_4$, R$_5$ and R$_6$=H, Y=(CH$_2$)$_5$, oxazole at 4-position], m.p. 80°-80.2° C. (from propanol-pentane), was prepared from 4-(4,5-dihydro-2-oxazolyl)-2-(dimethylamino)phenol, m.p. 145.5°-146° C. (from acetone) and 5-(5-bromopentyl)-3-methylisoxazole. The final product was separated from a by-product by chromatographic procedures.

EXAMPLE 101

(a) 5-[2-(4-Bromomethylcyclohexyl)ethyl]-3-methylisoxazole

Butyllithium (23.3 ml, 8.0M in tetrahydrofuran) was added dropwise to a solution of 18.3 g of 3,5-dimethylisoxazole in 800 ml of tetrahydrofuran held at −77° C. under nitrogen, and the mixture was stirred for 30 minutes. 1,4-bis(Bromomethyl)cyclohexane (50.4 g) was then added, and the reaction mixture was stirred for 3 hours at −70° C. and at room temperature overnight. The product was isolated and purified by chromatography to give 31 g (58%) of 5-[2-(4-bromomethylcyclohexyl)ethyl]-3-methylisoxazole as a liquid used directly in the next reaction.

(b) 5-{2-[4-[[4-(4,5-Dihydro-2-oxazolyl)phenoxy]methyl]cyclohexyl]ethyl}-3-methylisoxazole [IX; R=CH$_3$, R$_1$, R$_2$, R$_3$, R$_4$, R$_5$ and R$_6$=H, Y=—CH$_2$CH$_2$-cyclohexyl-CH$_2$—, oxazole at 4-position], m.p. 159°-160° C., was prepared from 5-[2-(4-bromomethylcyclohexyl)ethyl]-3-methylisoxazole and 4-(4,5-dihydro-2-oxazolyl)phenol according to the procedure of Example 9, part (d).

EXAMPLE 102

5-{5-[4-(4,5-Dihydro-2-oxazolyl)-2-(propionylamino)phenoxy]pentyl}-3-methylisoxazole [IX; R=CH$_3$, R$_1$=2-CH$_3$CH$_2$—CONH, R$_2$, R$_3$, R$_4$, R$_5$ and R$_6$=H, Y=(CH$_2$)$_5$, oxazole at 4-position]

To a mixture of 1.5 g of 3-{5-[2-amino-4-(4,5-dihydro-2-oxazolyl)phenoxy]pentyl}-3-methylisoxazole (Example 49) and 0.51 g of triethylamine in 30 ml of methylene dichloride held at 0° C. was slowly added a solution of 0.42 g of propionyl chloride in methylene dichloride. After the addition was complete, the product (0.8 g) was isolated and purified by chromatography on silica gel to give 5-{5-[4-(4,5-dihydro-2-oxazolyl)-2-(propionylamino)phenoxy]pentyl}-3-methylisoxazole, m.p. 133°-134° C. when recrystallized from isopropyl acetate.

EXAMPLE 103

(a) N,N'-bis(2-Hydroxyethyl)-4,4'-dithiobis[benzamide] [(HOCH$_2$CH$_2$NHCOC$_6$H$_4$S)$_2$]

A mixture of 16.5 g of dimethyl 4,4'-dithiobis[benzoate] [Werbel et al., *J. Heterocycl. Chem.* 17, 497 (1980)] and 13.0 g of ethanolamine was heated at 140° C. while collecting the methanol which distilled from the reaction. After evolution of methanol had ceased, the reaction mixture was cooled and acidified with dilute hydrochloric acid. The solid product which formed was collected and dried to give 13.3 g of N,N'-bis(2-hydroxyethyl)-4,4'-dithiobis[benzamide], used directly in the next reaction.

(b) bis[4-(4,5-Dihydro-2-oxazolyl)phenyl]disulfide [XXVIII; R$_1$, R$_2$, R$_4$', R$_5$' and R$_6$'=H]

Thionyl chloride (20.0 g) was added to a stirred suspension of 13.3 g of N,N'-bis(2-hydroxyethyl)-4,4'-dithiobis[benzamide] in 250 ml of isopropyl acetate. The reaction mixture was allowed to stand for 3 days and the solid product was collected and dried to give 10.3 g of bis[4-(4,5-dihydro-2-oxazolyl)phenyl]disulfide, used directly in the next reaction.

(c) 5-{5-[[4-(4,5-Dihydro-2-oxazolyl)phenyl]thio]pentyl}-3-methylisoxazole [I; Het=4-(4,5-dihydro-2-oxazolyl), R=CH$_3$, R$_1$, R$_2$ and R$_3$=H, X=S, Y=(CH$_2$)$_5$]

To a mixture of 9.3 g of bis[4-(4,5-dihydro-2-oxazolyl)phenyl]disulfide and 12.1 g of 5-(5-bromopentyl)-3-methylisoxazole in 150 ml of tetrahydrofuran, stirred under nitrogen, was added 90 ml of 33% aqueous sodium hydroxide and 0.23 g of cetyltrimethylammonium bromide. The reaction mixture was heated at reflux for one hour, and then cooled and poured into 1.5 liter of ethyl acetate. The latter solution was washed with water and saturated sodium chloride solution, dried and concentrated in vacuo. The residue was recrystallized from triethylamine to give 6.8 g of 5-{5-[[4-(4,5-dihydro-2-oxazolyl)phenyl]thio]pentyl}-3-methylisoxazole, m.p. 89°-91° C.

EXAMPLE 104

5-{5-[[4-(4,5-Dihydro-2-oxazolyl)phenyl]sulfinyl]pentyl}-3-methylisoxazole [I; Z=N, Het=4-(4,5-dihydro-2-oxazolyl), R=CH$_3$, R$_1$, R$_2$ and R$_3$=H, X=SO, Y=(CH$_2$)$_5$]

A solution of 1.40 g (0.00811 mole) of m-chloroperbenzoic acid in 30 ml of chloroform was slowly added to a solution of 2.69 g (0.00814 mole) of 5-{5-[[4-(4,5-dihydro-2-oxazolyl)phenyl]thio]pentyl}-3-methylisoxazole (Example 103c) in 30 ml of chloroform cooled to 0° C. in an ice bath. The reaction mixture was allowed to warm to room temperature and then concentrated in vacuo. The residue was dissolved in 600 ml of ethyl acetate and the solution was washed with sodium bicarbonate solution and saturated sodium chloride solution, then dried and concentrated in vacuo to give 2.43 g of solid product. Purification by recrystallization from triethylamine gave 5-{5-[[4-(4,5-dihydro-2-oxazolyl)phenyl]sulfinyl]pentyl}-3-methylisoxazole, m.p. 110°-111° C.

EXAMPLE 105

(a) 3,5-Dichloro-4-hydroxy-N-(2-hydroxyethyl)benzamide [XV; R$_1$=3-Cl, R$_2$=5-Cl, R$_4$', R$_5$' and R$_6$'=H, OH at 4-position]

A 2 L, 3 necked, round bottom flask was charged with 2-aminoethanol (240 gm; 3.93 moles) and heated to 80° C. Methyl 3,5-dichloro-4-hydroxybenzoate (432 gm; 1.96 moles) was added in portions through a powder funnel. The resulting amber solution was heated to 145° C. and the liberated methanol distilled into a Dean Stark trap. The reaction required about 3.5 hrs. Upon completion, the solution was cooled to 90°–100° C. and dissolved in 1.95 L $H_2O$. The aqueous solution was cooled to 25° C., placed in an ice bath and made slightly acidic with concentrated hydrochloric acid (196 ml; 2.35 moles). The product precipitated and filtration afforded a white solid. After drying at 50° C. in a vacuum oven, the product darkened slightly. The crude material (384.4 gm; 78.8%) was ground and passed through a No. 20 mesh screen to produce 3,5-dichloro-4-hydroxy-N-(2-hydroxyethyl)benzamide as a cream colored solid (m.p. 174°–178° C.) which is suitable for use in the next step.

(b) 2,6-Dichloro-4-(4,5-dihydro-2-oxazolyl)phenol [XVI; $R_1$=2-Cl, $R_2$=6-Cl, $R_4'$, $R_5'$ and $R_6'$=H, oxazole at 4-position]

3,5-Dichloro-4-hydroxy-N-(2-hydroxyethyl)benzamide (400 gm, 1.61 moles) was ground and sifted through a No. 20 mesh screen prior to use. To a stirred suspension of the above in 2.8 L isopropyl acetate was added thionyl chloride (285 gm, 2.41 moles) in a steady stream. An exotherm to 45°–50° C. developed and the gray suspension appeared lighter after a short time. After stirring 2.5 hr, the suspension was cooled to room temperature and filtered. The cake was rinsed with isopropyl acetate and dried in a vacuum oven at room temperature overnight. There was obtained 371 gm (86% yield) of 2,6-dichloro-4-(4,5-dihydro-2-oxazolyl)-phenol in the form of its hydrochloride salt, m.p. 189°–191° C., acceptable for use in the next step. The purified free base had the m.p. 195° C. (decompn.).

(c) 5-{5-[2,6-Dichloro-4-(4,5-dihydro-2-oxazolyl)-phenoxy]pentyl}-3-methylisoxazole [IX; R=$CH_3$, $R_1$=2-Cl, $R_2$=6-Cl, $R_3$, $R_4$, $R_5$ and $R_6$=H, Y=$(CH_2)_5$, oxazole at 4-position]

To a stirred suspension of milled potassium carbonate (172.5 gm, 1.25 moles) in 1.35 L dimethylformamide (DMF) was added 2,6-dichloro-4-(4,5-dihydro-2-oxazolyl)phenol hydrochloride (133.5 gm, 0.5 moles). Heavy gas evolution ($CO_2$) occurred and the reaction was warmed on the steam bath to 70° C. After stirring for about 5 minutes, 5-(5-bromopentyl)-3-methylisoxazole (121.8 gm, 0.525 moles) was added in one portion. The mixture was heated to 90°–95° C. for 1 hr, allowed to cool to room temperature and then filtered. The filter cake was rinsed with DMF and the filtrate was concentrated under water vacuum to a viscous brown oil (260 gm). This residue was dissolved in 300 ml isopropyl acetate and washed with water and then with brine. The organic layer was dried over $MgSO_4$, charcoaled, filtered and evaporated to dryness. The crude product (220 gm oil) was diluted with 287 ml acetone (1.5 volumes based on theoretical yield) and was cooled and stirred in a Dry Ice/acetone bath to −25° C. The product was collected and air dried to give 115 gm (60% yield) of 5-{5-[2,6-dichloro-4-(4,5-dihydro-2-oxazolyl)-phenoxy]pentyl}-3-methylisoxazole, m.p. 38°–40° C. A sample when recrystallized from triethylamine had the m.p. 42°–43° C.

5-{5-[2,6-Dichloro-4-(4,5-dihydro-2-oxazolyl)-phenoxy]pentyl}-3-methylisoxazole when treated with methanesulfonic acid formed an acid-addition salt with m.p. 98°–101° C.

The intermediate 5-(5-bromopentyl)-3-methylisoxazole was prepared from 1,4-dibromobutane and the lithium salt of 3,5-dimethylisoxazole produced in situ with n-butyllithium and diisopropylamine in tetrahydrofuran solution.

By the processes described above in Example 105 were prepared the following compounds of Examples 106–116:

EXAMPLE 106

5-{6-[2,6-Dichloro-4-(4,5-dihydro-2-oxazolyl)-phenoxy]hexyl}-3-methylisoxazole [IX; R=$CH_3$, $R_1$=2-Cl, $R_2$=6-Cl, $R_3$, $R_4$, $R_5$ and $R_6$=H, Y=$(CH_2)_6$, oxazole at 4-position], m.p. 48°–50° C. (from triethylamine) was prepared in 60% yield by substituting 5-(6-bromohexyl)-3-methylisoxazole for the 5-(5-bromopentyl)-3-methylisoxazole in Example 105(c).

EXAMPLE 107

5-{5-[2,6-Dichloro-4-(4,5-dihydro-4-methyl-2-oxazolyl)phenoxy]pentyl}-3-methylisoxazole [IX; R=$CH_3$, $R_1$=2-Cl, $R_2$=6-Cl, $R_3$, $R_5$ and $R_6$=H, $R_4$=$CH_3$, Y=$(CH_2)_5$, oxazole at 4-position], viscous yellow oil by chromatography, m.p. below room temperature.

Intermediates: 5-(5-bromopentyl)-3-methylisoxazole and 2,6-dichloro-4-(4,5-dihydro-4-methyl-2-oxazolyl)-phenol, m.p. 145°–146° C., in turn prepared from 3,5-dichloro-4-hydroxy-N-(2-hydroxy-1-methylethyl)benzamide, m.p. 168°–170° C. (from acetonitrile).

EXAMPLE 108

5-{5-[2,6-Dichloro-4-(4,5-dihydro-5-methyl-2-oxazolyl)phenoxy]pentyl}-3-methylisoxazole [IX; R=$CH_3$, $R_1$=2-Cl, $R_2$=6-Cl, $R_3$, $R_4$ and $R_5$=H, $R_6$=$CH_3$, Y=$(CH_2)_5$, oxazole at 4-position], yellow oil by chromatography, m.p. below room temperature.

Intermediates: 5-(5-bromopentyl)-3-methylisoxazole and 2,6-dichloro-4-(4,5-dihydro-5-methyl-2-oxazolyl)-phenol, m.p. 173°–174° C., in turn prepared from 3,5-dichloro-4-hydroxy-N-(2-hydroxypropyl)benzamide, m.p. 126°–128° C. (from isopropyl acetate).

EXAMPLE 109

5-{5-[2,6-Dichloro-4-(4,5-dihydro-2-oxazolyl)-phenoxy]hexyl}-3-methylisoxazole [IX; Y=$CH_2CH_2CH_2CH_2CH(CH_3)$, R=$CH_3$, $R_1$=2-Cl, $R_2$=6-Cl, $R_3$, $R_4$, $R_5$ and $R_6$=H], colorless oil by chromatography.

Intermediates: 5-(5-bromohexyl)-3-methylisoxazole and 2,6-dichloro-4-(4,5-dihydro-2-oxazolyl)phenol.

EXAMPLE 110

5-{4-[2,6-Dichloro-4-(4,5-dihydro-2-oxazolyl)-phenoxy]pentyl}-3-methylisoxazole [IX; Y=$CH_2CH_2CH_2CH(CH_3)$, R=$CH_3$, $R_1$=2-Cl, $R_2$=6-Cl, $R_3$, $R_4$, $R_5$ and $R_6$=H], yellow oil by chromatography.

Intermediates: 5-(4-bromopentyl)-3-methylisoxazole and 2,6-dichloro-4-(4,5-dihydro-2-oxazolyl)phenol.

EXAMPLE 111

5-{5-[2-Bromo-4-(4,5-dihydro-2-oxazolyl)-6-nitrophenoxy]-pentyl}-3-methylisoxazole [IX; R=$CH_3$, $R_1$=2-Br, $R_2$=6-$NO_2$, $R_3$, $R_4$, $R_5$ and $R_6$=H, oxazole at 4-position], yellow oil by chromatography.

Intermediates: 5-(5-bromopentyl)-3-methylisoxazole and 2-bromo-4-(4,5-dihydro-2-oxazolyl)-6-nitrophenol. The latter, a bright yellow solid, was prepared by cyclization of 3-bromo-4-hydroxy-N-(2-hydroxyethyl)-5-nitrobenzamide, yellow solid, m.p. 163°–164° C. (from methanol-isopropyl acetate). The latter was in turn prepared by bromination of 4-hydroxy-3-nitrobenzoic acid to form 5-bromo-4-hydroxy-3-nitrobenzoic acid, m.p. 233°–234° C. (yellow solid from isopropyl acetate), esterification to the corresponding methyl ester, m.p. 128°–130° C. (yellow solid from carbon tetrachloride) and reaction of the latter with 2-hydroxyethylamine.

EXAMPLE 112

5-{5-[2,6-Dichloro-4-(4,5-dihydro-2-oxazolyl)-phenoxy]-3-pentenyl}-3-methylisoxazole (Z-isomer) [IX; Y=(CH$_2$)$_2$CH=CHCH$_2$, R=CH$_3$, R$_1$=2-Cl, R$_2$=6-Cl, R$_3$, R$_4$, R$_5$ and R$_6$=H, oxazole at 4-position], colorless solid, m.p. 52°–54° C. (from t-butyl methyl ether).

Intermediates: 2,6-dichloro-4-(4,5-dihydro-2-oxazolyl)phenol and the isomer of 5-(5-chloro-3-pentenyl)-3-methylisoxazole prepared from cis-1,4-dichloro-2-butene and 3,5-dimethylisoxazole.

EXAMPLE 113

5-{5-[2,6-Dichloro-4-(4,5-dihydro-2-oxazolyl)-phenoxy]-3-pentenyl}-3-methylisoxazole (E-isomer) [IX; Y=(CH$_2$)$_2$CH=CHCH$_2$, R=CH$_3$, R$_1$=2-Cl, R$_2$=6-Cl, R$_3$, R$_4$, R$_5$ and R$_6$=H, oxazole at 4-position], colorless solid, m.p. 59°–61° C. (from ether-hexane).

Intermediates: 2,6-dichloro-4-(4,5-dihydro-2-oxazolyl)phenol and the isomer of 5-(5-chloro-3-pentenyl)-3-methylisoxazole prepared from trans-1,4-dichloro-2-butene and 3,5-dimethylisoxazole.

EXAMPLE 114

5-{7-[2,6-Dichloro-4-(4,5-dihydro-2-oxazolyl)-phenoxy]heptyl}-3-methylisoxazole [IX; Y=(CH$_2$)$_7$, R=CH$_3$, R$_1$=2-Cl, R$_2$=6-Cl, R$_3$, R$_4$, R$_5$ and R$_6$=H, oxazole at 4-position], colorless solid, m.p. 36°–37° C. (from hexane-ether).

Intermediates: 5-(7-bromoheptyl)-3-methylisoxazole and 2,6-dichloro-4-(4,5-dihydro-2-oxazolyl)phenol.

EXAMPLE 115

5-{3-[2,6-Dichloro-4-(4,5-dihydro-2-oxazolyl)-phenoxy]propyl}-3-methylisoxazole [IX; Y=(CH$_2$)$_3$, R=CH$_3$, R$_1$=2-Cl, R$_2$=6-Cl, R$_3$, R$_4$, R$_5$ and R$_6$=H, oxazole at 4-position], colorless solid, m.p. 67°–68° C. (from ether).

Intermediates: 5-(3-iodopropyl)-3-methylisoxazole and 2,6-dichloro-4-(4,5-dihydro-2-oxazolyl)phenol.

EXAMPLE 116

5-{5-[2,6-Dichloro-4-(4,5-dihydro-2-oxazolyl)-phenoxy]pentyl}-3-isoxazolemethanol [IX; R=HOCH$_2$, R$_1$=2-Cl, R$_2$=6-Cl, R$_3$, R$_4$, R$_5$ and R$_6$=H, oxazole at 4-position], colorless solid, m.p. 65°–66° C. (from hexane-isopropyl acetate).

Intermediates: 2,6-dichloro-4-(4,5-dihydro-2-oxazolyl)phenol and 5-(5-chloropentyl)-3-hydroxymethylisoxazole, prepared from 3-hydroxymethyl-5-methylisoxazole and 1-chloro-4-bromobutane.

EXAMPLE 117

5-{-5-[2,6-Dichloro-4-(4,5-dihydro-2-oxazolyl)-phenoxy]pentyl}-3-(methoxymethyl)isoxazole [IX; Y=(CH$_2$)$_5$, R=CH$_3$O—CH$_2$, R$_1$=2-Cl, R$_2$=6-Cl, R$_3$, R$_4$, R$_5$ and R$_6$=H, oxazole at 4-position]

To a solution of 6.8 g of 5-{5-[2,6-dichloro-4-(4,5-dihydro-2-oxazolyl)phenoxy]pentyl}-3-isoxazolemethanol (Example 116) in 100 ml of dry tetrahydrofuran was added 0.45 g of sodium hydride. After hydrogen evolution had ceased, the solution was cooled in an ice-bath and 1.1 ml of methyl iodide was added. The reaction mixture was stirred at room temperature for 48 hrs, then diluted with ether and washed well with water. Evaporation of the solvent and chromatography provided 3.1 g of the product as a viscous yellow oil.

EXAMPLE 118

(a) 4-(4,5-Dimethyl-2-oxazolyl)-2,6-dimethylphenol N-oxide

Hydrogen chloride gas was passed through a mixture of 13.45 g 3,5-dimethyl-4-hydroxybenzaldehyde and 9.3 g 2,3-butanedione mono-oxime in 66.7 ml glacial acetic acid for 11 minutes. The reaction mixture was held at room temperature overnight, and the solid product was collected, washed with ether and dried to give 14.86 g 4-(4,5-dimethyl-2-oxazolyl)-2,6-dimethylphenol N-oxide in the form of its hydrochloride salt, m.p. 198°–201° C.

(b) 4-(4,5-Dimethyl-2-oxazolyl)-2,6-dimethylphenol

To a mixture of 14.86 g 4-(4,5-dimethyl-2-oxazolyl)-2,6-dimethylphenol N-oxide hydrochloride and 220 ml of acetic acid stirred at 100° C. was added portionwise 28 g of zinc dust. The reaction mixture was stirred at 100° C. for 1.5 hr and held at room temperature for three days. The product was isolated by partitioning between ethyl acetate and water. From the ethyl acetate fraction was obtained 11 g of product which was recrystallized from acetonitrile to give 7.31 g of 4-(4,5-dimethyl-2-oxazolyl)-2,6-dimethylphenol, m.p. 203°–205° C.

(c) 5-{5-[4-(4,5-Dimethyl-2-oxazolyl)-2,6-dimethylphenoxy]-pentyl}-3-methylisoxazole [I; R=CH$_3$, R$_1$=2-CH$_3$, R$_2$=6-CH$_3$, R$_3$=H, Y=(CH$_2$)$_5$, X=O, Het=4-(4,5-dimethyl-2-oxazolyl)], hydrochloride salt, m.p. 136°–140° C. (colorless granules from ethanol) was prepared from 4-(4,5-dimethyl-2-oxazolyl)-2,6-dimethylphenol and 5-(5-bromopentyl)-3-methylisoxazole.

EXAMPLE 119

(a) 2-(3,5-Dichloro-4-hydroxyphenyl)-4,5-dimethyloxazole N-oxide was prepared from 19.1 g 3,5-dichloro-4-hydroxybenzaldehyde and 10.1 g butanedione mono-oxime in formic acid in the presence of hydrogen chloride gas. There was obtained 12.2 g of product, m.p. 221°–223° C.

(b) 3,5-Dichloro-4-(4,5-dimethyl-2-oxazolyl)phenol

Titanium trichloride solution (20%, 100 ml) was added dropwise over a 30 minute period to a stirred mixture of 16.0 g of the N-oxide of part (a) in 1000 ml of tetrahydrofuran. The product was isolated and there was obtained 9.0 g 3,5-dichloro-4-(4,5-dimethyl-2-oxazolyl)-phenol, m.p. 228°–229° C.

(c) 5-{5-[2,6-Dichloro-4-(4,5-dimethyl-2-oxazolyl)-phenoxy]-pentyl}-3-methylisoxazole [I; R=CH$_3$, R$_1$=2-Cl, R$_2$=6-Cl, R$_3$=H, Y=(CH$_2$)$_5$, X=O, Het=4-(4,5-dimethyl-2-oxazolyl)], m.p. 61°–62° C. (colorless solid from triethylamine), was prepared from 3,5-dichloro-4-(4,5-dimethyl-2-oxazolyl)phenol and 5-(5-bromopentyl)-3-methylisoxazole.

EXAMPLE 120

5-{4-[2,6-Dichloro-4-(4,5-dimethyl-2-oxazolyl)-phenoxy]-butyl}-3-methylisoxazole [I; Y=(CH$_2$)$_4$, X=O, R=CH$_3$, R$_1$=2-Cl, R$_2$=6-Cl, R$_3$=H, Het=4-(4,5-dimethyl-2-oxazolyl)], m.p. 64°–65° C. (from ether-hexane) was prepared from 3,5-dichloro-4-(4,5-dimethyl-2-oxazolyl)phenol (Example 119b) and 5-(4-bromobutyl)-3-methylisoxazole.

The compounds of the following Examples 121–130 were prepared according to the procedure of Examples 1(c) and 2(c) using the appropriate optically active amino alcohol in place of the 2-hydroxyethylamine of those examples:

EXAMPLE 121

(S)-5-{5-[4-(4,5-Dihydro-4-methyl-2-oxazolyl)-phenoxy]-pentyl}-3-methylisoxazole [IX; Y=$(CH_2)_5$, R=$CH_3$, $R_1$, $R_2$, $R_3$, $R_4$ and $R_6$=H, $R_5$=$CH_3$, oxazole at 4-position]; tan powder, m.p. 66°–67° C. (from isopropyl acetate), $[\alpha]_D^{25}$= −34.3° (1% in ethanol).

EXAMPLE 122

(S)-5-{7-[4-(4,5-Dihydro-5-methyl-2-oxazolyl)-phenoxy]heptyl}-3-methylisoxazole [IX; Y=$(CH_2)_7$, R=$CH_3$, $R_1$, $R_2$, $R_3$, $R_4$ and $R_5$=H, $R_6$=$CH_3$, oxazole at 4-position], colorless solid, m.p. 83°–84° C. (from methanol), $[\alpha]_D^{25}$= +14.5° (1% in ethanol).

EXAMPLE 123

(R)-5-{7-[4-(4,5-Dihydro-5-methyl-2-oxazolyl)-phenoxy]heptyl}-3-methylisoxazole [IX; Y=$(CH_2)_7$, R=$CH_3$, $R_1$, $R_2$, $R_3$, $R_4$ and $R_5$=H, $R_6$=$CH_3$, oxazole at 4-position], colorless powder, m.p. 83°–85° C., $[\alpha]_D^{25}$= −12.3° (1% in ethanol).

EXAMPLE 124

(S)-5-{7-[4-(4-Ethyl-4,5-dihydro-2-oxazolyl)phenoxy]heptyl}-3-methylisoxazole [IX; Y=$(CH_2)_7$, R=$CH_3$, $R_1$, $R_2$, $R_3$, $R_5$ and $R_6$=H, $R_4$=$C_2H_5$, oxazole at 4-position], colorless solid, m.p. 74°–75° C. (from methanol); $[\alpha]_D^{25}$= −26.8° (1% in ethanol).

EXAMPLE 125

(R)-5-{7-[4-(4-Ethyl-4,5-dihydro-2-oxazolyl)phenoxy]heptyl}-3-methylisoxazole [IX; Y=$(CH_2)_7$, R=$CH_3$, $R_1$, $R_2$, $R_3$, $R_4$ and $R_6$=H, $R_5$=$C_2H_5$, oxazole at 4-position], colorless solid, m.p. 72°–73° C. (from methanol); $[\alpha]_D^{25}$= +21.4° (1% in ethanol).

EXAMPLE 126

(S)-5-{7-[4-(4,5-Dihydro-4-isopropyl-2-oxazolyl)-phenoxy]-heptyl}-3-methylisoxazole [IX; Y=$(CH_2)_7$, R=$CH_3$, $R_1$, $R_2$, $R_3$, $R_5$ and $R_6$=H, $R_4$=$CH(CH_3)_2$, oxazole at 4-position], colorless needles, m.p. 67°–68° C. (from hexane); $[\alpha]_D^{25}$= −23.3° (1% in ethanol).

EXAMPLE 127

(R)-5-{7-[4-(4,5-Dihydro-4-isopropyl-2-oxazolyl)-phenoxy]-heptyl}-3-methylisoxazole [IX; Y=$(CH_2)_7$, R=$CH_3$, $R_1$, $R_2$, $R_3$, $R_4$ and $R_6$=H, $R_5$=$CH(CH_3)_2$, oxazole at 4-position], colorless crystals, m.p. 66°–68° C. (from hexane); $[\alpha]_D^{25}$= −24.7° (1% in ethanol).

EXAMPLE 128

(S)-5-{7-[4-(4,5-Dihydro-4-propyl-2-oxazolyl)-phenoxy]heptyl}-3-methylisoxazole [IX; Y=$(CH_2)_7$, R=$CH_3$, $R_1$, $R_2$, $R_3$, $R_5$ and $R_6$=H, $R_4$=$CH_2CH_2CH_3$, oxazole at 4-position], colorless solid, m.p. 80°–81° C. (from methanol); $[\alpha]_D^{25}$= −29.7° (1% in ethanol).

EXAMPLE 129

(R)-5-{7-[4-(4,5-Dihydro-4-propyl-2-oxazolyl)-phenoxy]heptyl}-3-methylisoxazole [IX; Y=$(CH_2)_7$, R=$CH_3$, $R_1$, $R_2$, $R_3$, $R_4$ and $R_6$=H, $R_5$=$CH_2CH_2CH_3$, oxazole at 4-position], colorless solid, m.p. 79°–80° C. (from ethanol); $[\alpha]_D^{25}$= +30.8° (1% in ethanol).

EXAMPLE 130

(S)-5-{7-[4-(4-Butyl-4,5-dihydro-2-oxazolyl)phenoxy]heptyl}-3-methylisoxazole [IX; Y=$(CH_2)_7$, R=$CH_3$, $R_1$, $R_2$, $R_3$, $R_5$ and $R_6$=H, $R_4$=$(CH_2)_3CH_3$, oxazole at 4-position], colorless needles, m.p. 83°–84° C. (from ethanol); $[\alpha]_D^{25}$= −27.7° (1% in ethanol).

EXAMPLE 131

(R)-5-{7-[4-(4-Butyl-4,5-dihydro-2-oxazolyl)phenoxy]heptyl}-3-methylisoxazole [IX; Y=$(CH_2)_7$, R=$CH_3$, $R_1$, $R_2$, $R_3$, $R_4$ and $R_6$=H, $R_5$=$(CH_2)_3CH_3$, oxazole at 4-position], colorless solid, m.p. 83°–84° C. (from ethanol); $[\alpha]_D^{25}$= −27.8° (1% in ethanol).

EXAMPLE 132

(S)-5-{2-[4-(4,5-Dihydro-4-methyl-2-oxazolyl)-phenoxy]ethyl}-3-hexylisoxazole [IX; Y=$(CH_2)_2$, R=$(CH_2)_5CH_3$, $R_1$, $R_2$, $R_3$, $R_5$ and $R_6$=H, $R_4$=$CH_3$, oxazole at 4-position] was prepared from 4-[2-(3-hexyl-3-isoxazolyl)ethoxy]benzoic acid [XL; Y=$(CH_2)_2$, $R'$=$(CH_2)_5CH_3$, $R_1'$ and $R_2'$=H], m.p. 122°–123° C., by conversion of the latter to its acid chloride with oxalyl chloride, reaction of the acid chloride with S-(+)-2-amino-1-propanol, and finally cyclization with 1,8-diazabicyclo[5.4.0]undec-7-ene (DBU).

EXAMPLE 133

5-{5-[4-(4-Methyl-2-oxazolyl)phenoxy]pentyl}-3-methylisoxazole [I; Het=4-(4-methyl-2-oxazolyl), R=$CH_3$, $R_1$, $R_2$ and $R_3$=H, X=O, Y=$(CH_2)_5$] was prepared from 4-(4-methyl-2-oxazolyl)phenol, m.p. 192°–193° C., and 3-methyl-5-(5-bromopentyl)isoxazole, and was obtained in 48% yield as a colorless solid, m.p. 83°–84° C.

EXAMPLE 134

5-{5-[2-Chloro-4-(4,5-dimethyl-2-oxazolyl)phenoxy]-pentyl}-3-methylisoxazole [I; Het=4-(4,5-dimethyl-2-oxazolyl), R=$CH_3$, $R_1$=2-Cl, $R_2$ and $R_3$=H, X=O, Y=$(CH_2)_5$], colorless solid, m.p. 89°–90° C. (from methyl t-butyl ether), was prepared by a procedure analogous to that of Example 89. The starting material was 3,5-dichloro-4-methoxybenzaldehyde; however one of the chlorine atoms was lost during the course of the subsequent reactions.

EXAMPLE 135

5-{7-[4-(4-Methyl-2-oxazolyl)phenoxy]heptyl}-3-methylisoxazole [I; Het=4-(4-methyl-2-oxazolyl), R=$CH_3$, $R_1$, $R_2$ and $R_3$=H, X=O, Y=$(CH_2)_7$] was prepared from 4-(4-methyl-2-oxazolyl)phenol and 5-(7-bromoheptyl)-3-methylisoxazole, and was obtained in 60% yield as a colorless solid, m.p. 92°–92.5° C.

EXAMPLE 136

(a) 5-{7-[4-(4,5-Dihydro-2-oxazolyl)phenoxy]heptyl}-3-isoxazolemethanol methanesulfonyl ester To a solution of 4.0 g 5-{7-[4-(4,5-dihydro-2-oxazolyl)phenoxy]heptyl}-3-isoxazolemethanol (Example 11) in 135 ml anhydrous tetrahydrofuran was added 2.3 g triethylamine and 1.33 g methanesulfonyl chloride. The reaction mixture was stirred for 10 min., an additional one-third molar equivalent of acid chloride was then added and the mixture stirred for 7 min. longer. The amine hydrochloride was removed by filtration and the product isolated to give 4.78 g of ester, m.p. 96°–98° C.

(b) 5-{7-[4-(4,5-Dihydro-2-oxazolyl)phenoxy]heptyl}-3-(dimethylaminomethyl)isoxazole [IX; Y=(CH$_2$)$_7$, R=(CH$_3$)$_2$N—CH$_2$, R$_1$, R$_2$, R$_3$, R$_4$, R$_5$ and R$_6$=H, oxazole at 4-position].

A solution of 1.6 g of the product of part (a) in 25 ml tetrahydrofuran and an excess of dimethylamine (40% aqueous solution) was heated at reflux until reaction was complete. Isolation of the resulting product and recrystallization from hexane gave 0.92 g 5-{7-[4-(4,5-dihydro-2-oxazolyl)phenoxy]heptyl}-3-(dimethylaminomethyl)isoxazole, colorless solid, m.p. 69.5°-70° C.

EXAMPLE 137

5-{7-[4-(4,5-Dihydro-2-oxazolyl)phenoxy]heptyl}-3-(diethylaminomethyl)isoxazole [IX; Y=(CH$_2$)$_7$, R=(C$_2$H$_5$)$_2$NCH$_2$, R$_1$, R$_2$, R$_3$, R$_4$, R$_5$ and R$_6$=H, oxazole at 4-position], m.p. 64°-64.5° C., colorless flakes from hexane, was prepared according to Example 136(b), replacing the dimethylamine by diethylamine.

EXAMPLE 138

5-{5-[2,6-Dichloro-4-(4,5-dihydro-4-hydroxymethyl-2-oxazolyl)phenoxyl]pentyl}-3-methylisoxazole [IX; Y=(CH$_2$)$_5$, R=CH$_3$, R$_1$=2-Cl, R$_2$=6-Cl, R$_3$, R$_5$ and R$_6$=H, R$_4$=CH$_2$OH, oxazole at 4-position], m.p. 51°-52° C., colorless powder from methanol, was prepared from the imino-ester hydrochloride of Example 2(c) and 2-amino-1,3-propanediol in 92% yield.

EXAMPLE 139

5-{7-[4-(4,5-Dihydro-4-(2-propenyl)-2-oxazolyl)-phenoxyl]-heptyl}-3-methylisoxazole [IX; Y=(CH$_2$)$_7$, R=CH$_3$, R$_1$, R$_2$, R$_3$, R$_5$ and R$_6$=H, R$_4$=CH$_2$CH=CH$_2$, oxazole at 4-position], m.p. 66°-67° C., colorless solid from ethanol, was prepared from the imino-ester hydrochloride of Example 1(c) and D,L-2-aminopent-4-enol in 78% yield.

EXAMPLE 140

5-{7-[4-(4-Chloromethyl-4,5-dihydro-2-oxazolyl)-phenoxy]-heptyl}-3-methylisoxazole [IX; Y=(CH$_2$)$_7$, R=CH$_3$, R$_1$, R$_2$, R$_3$, R$_5$ and R$_6$=H, R$_4$=CH$_2$Cl, oxazole at 4-position], light tan solid, m.p. 54°-55° C., was prepared from the hydroxymethyl compound of Example 33 and thionyl chloride, stirred overnight in methylene chloride solution at room temperature (yield 65%).

EXAMPLE 141

5-{5-[2-Ethenyl-4-(4,5-dihydro-2-oxazolyl)phenoxy]-pentyl}-3-methylisoxazole [IX; Y=(CH$_2$)$_5$, R=CH$_3$, R$_1$=2-CH=CH$_2$, R$_2$, R$_3$, R$_4$, R$_5$ and R$_6$=H, oxazole at 4-position]

To a suspension of 5.22 g triphenylmethylphosphine bromide in 75 ml tetrahydrofuran at 0° C. under nitrogen was added 10.6 ml 1.55 m n-butyllithium, and the mixture was stirred at room temperature for two hours. There was then added dropwise 5 g 4-(4,5-dihydro-2-oxazolyl)-2-formylphenol in 25 ml tetrahydrofuran and the reaction mixture allowed to stand at room temperature overnight. The product was isolated and recrystallized from ethyl acetate to give 1.8 g 5-{5-[2-ethenyl-4-(4,5-dihydro-2-oxazoly)phenoxy]pentyl}-3-methylisoxazole, colorless powder, m.p. 116°-117° C.

EXAMPLE 142

5-{6-[4-(4,5-Dihydro-2-oxazolyl)phenyl]hexyl}-3-methylisoxazole [II; n=6, R=CH$_3$, R$_1$, R$_2$, R$_3$, R$_4$, R$_5$ and R$_6$=H, oxazole at 4-position], m.p. 56°-58° C., colorless solid from ethyl acetate/hexane, was prepared in 33% yield from 4-[6-(3-methyl-5-isoxazolyl)hexyl]-benzoic acid by conversion to its acid chloride with thionyl chloride, reaction of the latter with 2-hydroxyethylamine to form the hydroxyethylamide, conversion to the chloroamide with thionyl chloride and then cyclization with DBU.

The intermediate benzoic acid derivative was prepared by alkylation of p-toluic acid with 6-(6-bromohexyl)-3-methylisoxazole in the presence of lithium diethylamide.

EXAMPLE 143

5-{7-[2-Chloro-4-(4,5-dihydro-2-oxazolyl)phenoxy]-hepty}-3-methyl-4-isoxazolemethanol [IX; Y=(CH$_2$)$_7$, R=CH$_3$, R$_1$=2-Cl, R$_2$=H, R$_3$=CH$_2$OH, R$_4$, R$_5$ and R$_6$=H, oxazole at 4-position], m.p. 71°-73° C., colorless powder from acetonitrile, was prepared in 22% yield according to the procedure of Example 29 from 2,5-dimethyl-4-hydroxymethylisoxazole and 2-[4-(6-bromohexyloxy)-3-chlorophenyl]-4,5-dihydro-oxazole, m.p. 60°-61° C. (from isopropyl acetate/hexane).

EXAMPLE 144

5-{5-[2,6-Dimethyl-4-(4-oxazolyl)phenoxy]pentyl}-3-methylisoxazole [XXIX; n=5, R$_1$ and R$_2$=CH$_3$], m.p. 47°-48° C. (pale yellow powder from isopropyl acetate/hexane) was prepared in 38% yield by reacting 4-(4-oxazoly)-2,6-dimethylphenol, m.p. 113°-115° C., with 5-(5-bromopentyl)-3-methylisoxazole according to the procedure of Example 9(c) but using potassium hydroxide in place of potassium carbonate.

The intermediate phenol was prepared by reacting 4-bromoacetyl-2,6-dimethylphenol with formamide and formic acid, heated under reflux for two hours.

EXAMPLE 145

5-{5-[4-(5-Chloro-2-oxazolyl)phenoxy]pentyl}-3-methylisoxazole [XXX; n=5, R$_1$ and R$_2$=H, Hal=Cl], m.p. 79°-80° C. (colorless solid from triethylamine), was prepared in 51% yield from 4-(5-chloro-2-oxazolyl)phenol and 5-(5-bromopentyl)-3-methylisoxazole according to the procedure of Example 9(c).

The intermediate phenol was prepared by reacting 4-(2-oxazolyl)phenol (Example 87a) with sulfuryl chloride in ether/methylene dichloride solution, three hours at reflux.

EXAMPLE 146

5-{5-[2-Ethoxycarbonyl-4-(4,5-dihydro-2-oxazolyl)-phenoxyl]-pentyl}-3-methylisoxazole [XXXI; n=5, lower-alkyl=C$_2$H$_5$], m.p. 72°-73° C. (colorless needles from ethyl acetate/hexane), was prepared by esterification of the corresponding carboxylic acid (Example 86) with ethyl iodide and potassium carbonate in acetonitrile solution, two hours at reflux.

EXAMPLE 147

5-{5-[2-(2-Bromoethenyl)-4-(4,5-dihydro-2-oxazolyl)-phenoxy]pentyl}-3-methylisoxazole [XXXII; n=5, Hal=Br]

To a solution of 1.255 g piperidine in 100 ml ether at 0° under nitrogen was added 12 ml n-butyllithium (1.23 m) followed by 5 g triphenylphosphine bromide. The mixture was then stirred two hours at room temperature and 4.78 g 5-{5-[2-formyl-4-(4,5-dihydro-2-oxazolyl)-phenoxy]pentyl}-3-methylisoxazole (Example 70) in 35 ml tetrahydrofuran was added dropwise. The reaction mixture was kept overnight at room temperature and worked up by chromatography to give 0.53 g 5-{5-[2-(2-bromoethenyl)-4-(4,5-dihydro-2-oxazolyl)phenoxy]-pentyl}-3-methylisoxazole, colorless needles, m.p. 94°–96° C. after recrystallization from isopropyl acetate and hexane.

EXAMPLE 148

5-{5-[2,6-Dichloro-4-(4,5-dihydro-2-oxazolyl)-phenoxy]pentyl}-3-isoxazolylmethyl methyl butanedioate [XXXIII; n=5, $R_1$ and $R_2$=Cl, Lower-alkyl=$CH_3$]

To a solution of 5.0 g of 5-{5-[2,6-dichloro-4-(4,5-dihydro-2-oxazolyl)phenoxy]pentyl}-3-isoxazolemethanol (Example 116), 1.75 g of monomethyl succinate and a catalytic amount of p-dimethylaminopyridine in 100 ml of chloroform at 0° C. was added 2.6 g of dicyclohexylcarbodiimide. The reaction mixture was stirred at room temperature for 24 hrs, and then filtered and concentrated to give 4.5 g of product which upon recrystallization from isopropyl acetate-hexane gave 4.2 g of 5-{5-[2,6-dichloro-4-(4,5-dihydro-2-oxazolyl)phenoxy]pentyl}-3-isoxazolylmethyl methyl butanedioate, m.p. 39°–41° C.

EXAMPLE 149

(a) 5-{5-[2,6-Dichloro-4-(4,5-dihydro-2-oxazolyl)-phenoxy]-pentyl}-3-isoxazolylmethoxymethoxyethyl acetate [XXIV; n=5, $R_1$ and $R_2$=Cl] was prepared from 4.0 g of 5-{5-[2,6-dichloro-4-(4,5-dihydro-2-oxazolyl)phenoxy]pentyl}-3-isoxazolemethanol (Example 116) and 2.0 g of 2-acetoxyethoxymethyl bromide [$CH_3COCH_2CH_2OCH_2Br$] in the presence of sodium hydride according to the procedure of Example 117, and was obtained in the form of a colorless oil (2.4 g).

(b) 5-{5-[2,6-Dichloro-4-(4,5-dihydro-2-oxazolyl)-phenoxy]-pentyl}-3-isoxazolylmethoxymethoxyethanol [I; Y=$(CH_2)_5$, X=O, Z=N, m=O, R=HO($CH_2$)$_2$O$CH_2$O$CH_2$, $R_1$ and $R_2$=Cl, $R_3$ and $R_4$=H] was prepared by hydrolysis of the acetate of part (a) with lithium hydroxide in methanol, 12 hrs at room temperature and obtained as a pale yellow oil (2.8 g).

EXAMPLE 150

(a) 5-(5-Chloropentyl)-3-methylisothiazole

To a solution of 6.4 g 3-methylisothiazole in 100 ml dry tetrahydrofuran at −78° C. under nitrogen was slowly added 7.6 ml n-butyllithium (9.5 m). After 15 min. at −78° C., a solution of 12.0 g 1-bromo-5-chloropentane in 10 ml dry ether was added. The reaction mixture was allowed to reach room temperature where it was stirred for 90 min., then diluted with ether, washed with water and sodium chloride solution, and dried over sodium sulfate. Concentration and flash filtration (silica gel, 4:1 hexane/ethyl acetate) gave 6.5 g of 5-(5-chloropentyl)-3-methylisothiazole as a red oil, sufficiently pure (NMR) for use in the subsequent reaction.

(b) 2-{3,5-Dichloro-4-[(5-(3-methyl-5-isothiazolyl)-penyl)-oxy]phenyl}-4,5-dihydro-oxazole [XXXV; n=5, $R_1$ and $R_2$=Cl]

A suspension of 6.5 g 5-(5-chloropentyl)-3-methylisothiazole, 5.3 g potassium iodide, 9.1 g 2,6-dichloro-4-(4,5-dihydro-2-oxazolyl)phenol and 3.9 g potassium hydroxide in 300 ml acetonitrile was heated at reflux for 40 hours. Filtration, concentration and flash filtration (silica gel; 1:1 hexane/ethyl acetate) gave 9.8 g of oily product which when crystallized from hexane at Dry Ice temperature gave 5.3 g 2-{3,5-dichloro-4-[(5-(3-methyl-5-isothiazolyl)pentyl)oxy]phenyl}-4,5-dihydro-oxazole as a colorless solid, m.p. 38°–39.5° C.

EXAMPLE 151

5-{5-[2,6-Dichloro-4-(4,5-dihydro-2-oxazolyl)-phenoxy]-3-pentynyl}-3-methylisoxazole [XXXVI; Y'=$CH_2CH_2C\equiv CCH_2$, $R_1$ and $R_2$=Cl], m.p. 70°–72° C. (colorless powder from ether/hexane) was prepared from 5-(5-chloro-3-pentynyl)-3-methylisoxazole and 2,6-dichloro-4-(4,5-dihydro-2-oxazolyl)phenol according to the procedure of Example 9(c).

The intermediate 5-(5-chloro-3-pentynyl)-3-methylisoxazole was prepared from 3,5-dimethylisoxazole and 1,4-dichloro-2-butyne in the presence of n-butyllithium.

EXAMPLE 152

(a) Methyl 3-bromo-5-chloro-4-{[5-(3-methyl-5-isoxazolyl)-pentyl]oxy}benzoate [XXXIX; Y=$(CH_2)_5$, $R_1'$=Cl, $R_2'$=Br, Alk=$CH_3$] was prepared from 41.3 g methyl 3-bromo-5-chloro-4-hydroxybenzoate (prepared by bromination of 3-chloro-4-hydroxybenzoic acid and esterification), 40.6 g 5-(5-bromopentyl)-3-methylisoxazole, 61.7 g potassium carbonate and 0.2 g sodium iodide in 500 ml of dimethylformamide, 3 hrs at 90°–95° C., and was obtained in the form of a colorless oil after chromatography on silica.

(b) 3-Bromo-5-chloro-4-{[5-(3-methyl-5-isoxazolyl)-pentyl]-oxy}benzoic acid [XL; Y=$(CH_2)_5$, $R_1'$=Cl, $R_2'$=Br] was prepared by hydrolysis of 51.3 g of the ester of part (a) with 3.1 g lithium hydroxide in 500 ml methanol and 10 ml water, heated at reflux overnight. The reaction mixture was diluted, acidified and extracted with ethyl acetate. From the latter was obtained 42.8 g product, m.p. 104°–105° C. after recrystallization from ether-hexane.

(c) 3-Bromo-5-chloro-N-(2-chloroethyl)-4-{[5-(3-methyl-5-isoxazolyl)pentyl]oxy}benzamide [XXXVII; Y=$(CH_2)_5$, m=0, R'=$CH_3$, $R_1'$=Cl, $R_2'$=Br, $R_4'$, $R_5'$ and $R_6'$=H, Hal'=Cl]

The acid of part (b) (29.2 g) was stirred with excess thionyl chloride (about 35 ml) for about 16 hrs. The unreacted thionyl chloride was aspirated off and 250 ml chloroform was added, followed by 21 g 2-chloroethylamine hydrochloride. This mixture was cooled to 0° C. and 80 ml triethylamine was added dropwise. The reaction mixture was stirred overnight, then diluted with chloroform and washed with dilute hydrochloric acid. From the chloroform solution was obtained 30.9 g product of sufficient purity to be used in the next step. A sample of the compound when purified by chromatography and recrystallized from isopropyl alcohol had the m.p. 84°–86° C.

(d) 5-{5-[2-Bromo-6-chloro-4-(4,5-dihydro-2-oxazolyl)phenoxy]pentyl}-3-methylisoxazole [IX; Y=$(CH_2)_5$, $R_1$=2-Br, $R_2$=6-Cl, R=$CH_3$, $R_3$, $R_4$, $R_5$ and $R_6$=H, oxazole at 4-position]

A mixture of 19.0 g of the chloroamide of part (c) and 12.0 g 1,8-diazabicyclo[5.4.0]undec-7-ene in 250 ml methylene dichloride was heated at reflux for two days. The product was isolated, purified through silica gel and recrystallized from ether to give 10.0 g of 5-{5-[2-bromo-6-chloro-4-(4,5-dihydro-2-oxazolyl)phenoxy]-pentyl}-3-methylisoxazole, m.p. 41°–42° C.

The following Examples 153–162 were prepared by procedures analogous to those described in Example 152.

EXAMPLE 153

(a) Methyl 3-chloro-4-{[5-(3-methyl-5-isoxazolyl)pentyl]-oxy}-5-nitrobenzoate [XXXIX; Y=(CH$_2$)$_5$, R$_1'$=Cl, R$_2'$=NO$_2$, Alk=CH$_3$], m.p. 65°–67° C. (from t-butyl methyl ether).

The intermediate methyl 3-chloro-4-hydroxy-5-nitrobenzoate was a yellow solid, m.p. 118°–119° C. (from carbon tetrachloride).

(b) 3-Chloro-4-{[5-(3-methyl-5-isoxazolyl)phentyl]oxy}-5-nitrobenzoic acid [XL; Y=(CH$_2$)$_5$, R$_1'$=Cl, R$_2'$=NO$_2$], m.p. 94°–95° C. (from hexane-isopropyl acetate).

(c) 3-Chloro-N-(2-chloroethyl)-4-{[5-(3-methyl-5-isoxazolyl)pentyl]oxy}-5-nitrobenzamide [XXXVII; Y=(CH$_2$)$_5$, m=0, R'=CH$_3$, R$_1'$=Cl, R$_2'$=NO$_2$, R$_4'$, R$_5'$ and R$_6'$=H, Hal'=Cl], m.p. 73°–74° C. (from t-butyl methyl ether).

(d) 5-{5-[2-Chloro-4-(4,5-dihydro-2-oxazolyl)-6-nitrophenoxy]pentyl}-3-methylisoxazole [IX; Y=(CH$_2$)$_5$, R$_1$=2-Cl, R$_2$=6-NO$_2$, R=CH$_3$, R$_3$, R$_4$, R$_5$ and R$_6$=H, oxazole at 4-position], viscous yellow oil after chromatography.

EXAMPLE 154

(a) 3-Chloro-5-methyl-4-{[5-(3-methyl-5-isoxazolyl)pentyl]oxy}benzoic acid [XL; Y=(CH$_2$)$_5$, R$_1'$=Cl, R$_2'$=CH$_3$], m.p. 98°–99° C. (from ether-hexane).

The foregoing compound was prepared from 3-chloro-4-hydroxy-5-methylbenzaldehyde, brownish-orange flakes, m.p. 114°–116° C. (prepared from 2-chloro-6-methylphenol and hexamethylenetetramine in trifluoroacetic acid), by alkylation with 5-(5-bromopentyl)-3-methylisoxazole to produce 3-chloro-5-methyl-4-{[5-(3-methyl-5-isoxazolyl)pentyl]oxy}benzaldehyde, and oxidation of the latter with silver nitrate.

(b) 3-Chloro-N-(2-chloroethyl)-5-methyl-4-{[5-(3-methyl-5-isoxazolyl)pentyl]oxy}benzamide [XXXVII; Y=(CH$_2$)$_5$, m=0, R'=CH$_3$, R$_1'$=Cl, R$_2'$=CH$_3$, R$_4'$, R$_5'$ and R$_6'$=H, Hal'=Cl], m.p. 84°–85° C. (from ether).

(c) 5-{5-[2-Chloro-4-(4,5-dihydro-2-oxazolyl)-6-methylphenoxy]pentyl}-3-methylisoxazole [IX; Y=(CH$_2$)$_5$, R$_1$=2-Cl, R$_2$=6-CH$_3$, R=CH$_3$, R$_3$, R$_4$, R$_5$ and R$_6$=H, oxazole at 4-position], colorless liquid.

EXAMPLE 155

(a) 3-Chloro-4-{[5-(3-methyl-5-isoxazolyl)pentyl]oxy}-5-trifluoromethylbenzoic acid [XL; Y=(CH$_2$)$_5$, R$_1'$=Cl, R$_2'$=CF$_3$].

The foregoing compound was prepared by chlorination of 3-trifluoromethyl-4-hydroxybenzonitrile, alkylation of the latter with 5-(5-iodopentyl)-3-methylisoxazole to produce 3-chloro-4-{[5-(3-methyl-5-isoxazolyl)pentyl]oxy}-5-trifluoromethylbenzonitrile, followed by hydrolysis of the nitrile group to a carboxy group.

(b) 3-Chloro-N-(2-chloroethyl)-4-{[5-(3-methyl-5-isoxazolyl)pentyl]-5-trifluoromethylbenzamide [XXXVII; Y=(CH$_2$)$_5$, m=0, R'=CH$_3$, R$_1'$=CF$_3$, R$_4'$, R$_5'$ and R$_6'$=H, Hal'=Cl].

(c) 5-{5-[2-Chloro-4-(4,5-dihydro-2-oxazolyl)-6-(trifluoromethyl)phenoxy]pentyl}-3-methylisoxazole [IX; Y=(CH$_2$)$_5$, R$_1$=2-Cl, R$_2$=6-CF$_3$, R=CH$_3$, R$_3$, R$_4$, R$_5$ and R$_6$=H, oxazole at 4-position], pale yellow liquid by chromatography.

EXAMPLE 156

(a) 3,5-Dichloro-N-(3-chloropropyl)-4-{[5-(3-methyl-5-isoxazolyl)pentyl]oxy}benzamide [XXXVII; Y=(CH$_2$)$_5$, m=1, R'=CH$_3$, R$_1'$ and R$_2'$=Cl, R$_4'$, R$_5'$, R$_6'$ and R$_7'$=H, Hal'=Cl], colorless needles, m.p. 72°–73° C.

(b) 5,6-Dihydro-2-{2,6-dichloro-4-[5-(3-methyl-5-isoxazolyl)pentyloxy]phenyl}-4H-1,3-oxazine [I; Y=(CH$_2$)$_5$, X=O, R=CH$_3$, R$_1$=2-Cl, R$_2$=6-Cl, R$_3$=H, Het=5,6-dihydro-4H-1,3-oxazin-2-yl], colorless oil.

EXAMPLE 157

(a) Methyl 3-ethyl-5-methyl-4-{[5-(3-methyl-5-isoxazolyl)pentyl]oxy}benzoate [XXXIX; Y=(CH$_2$)$_5$, R$_1'$=CH$_3$, R$_2'$=C$_2$H$_5$, Alk=CH$_3$], pale yellow viscous liquid.

(b) 3-Ethyl-5-methyl-4-{[5-(3-methyl-5-isoxazolyl)pentyl]oxy}benzoic acid [XL; Y=(CH$_2$)$_5$, R$_1'$=CH$_3$, R$_2'$=C$_2$H$_5$], colorless solid, m.p. 74°–75° C.

(c) N-(2-Chloroethyl)-3-ethyl-5-methyl-4-{[5-(3-methyl-5-isoxazolyl)pentyl]oxy}benzamide [XXXVII; Y=(CH$_2$)$_5$, m=0, R'=CH$_3$, R$_1'$=CH$_3$, R$_2'$=C$_2$H$_5$, R$_4'$, R$_5'$ and R$_6'$=H, Hal'=Cl], colorless solid, m.p. 96°–96.2° C. (from ether).

(d) 5-{5-[4-(4,5-Dihydro-2-oxazolyl)-2-ethyl-6-methylphenoxy]pentyl}-3-methylisoxazole [IX; Y=(CH$_2$)$_5$, R$_1$=2-CH$_3$, R$_2$=6-C$_2$H$_5$, R=CH$_3$, R$_3$, R$_4$, R$_5$ and R$_6$=H, oxazole at 4-position], clear colorless viscous liquid.

EXAMPLE 158

(a) 3,5-Dimethoxy-4-{[5-(3-methyl-5-isoxazolyl)pentyl]oxy}benzoic acid [XL; Y=(CH$_2$)$_5$, R$_1'$ and R$_2'$=OCH$_3$], m.p. 110°–111° C., colorless crystals from ether/hexane; in this instance prepared by oxidation of 3,5-dimethoxy-4-{[5-(3-methyl-5-isoxazolyl)pentyl]oxy}benzaldehyde with silver nitrate and potassium hydroxide. The aldehyde in turn was prepared from 3,5-dimethoxy-4-hydroxybenzaldehyde and 5-(5-bromopentyl)-3-methylisoxazole.

(b) N-(2-Chloroethyl)-3,5-dimethoxy-4-{[5-(3-methyl-5-isoxazolyl)pentyl]oxy}benzamide [XXXVII; Y=(CH$_2$)$_5$, m=0, R'=CH$_3$, R$_1'$ and R$_2'$=OCH$_3$, R$_4'$, R$_5'$ and R$_6'$=H, Hal'=Cl], light tan powder, m.p. 78°–80° C.

(c) 5-{5-[4-(4,5-Dihydro-2-oxazolyl)-2,6-dimethoxyphenoxy]pentyl}-3-methylisoxazole [IX; Y=(CH$_2$)$_5$, R$_1$ and R$_2$=OCH$_3$, R=CH$_3$, R$_3$, R$_4$, R$_5$ and R$_6$=H, oxazole at 4-position], chromatographed, clear colorless oil.

EXAMPLE 159

(a) 3,5-Difluoro-4-{[5-(3-methyl-5-isoxazolyl)pentyl]oxy}benzoic acid [XL; Y=(CH$_2$)$_5$, R$_1'$ and R$_2'$=F].

(b) N-(2-Chloroethyl)-3,5-difluoro-4-{[5-(3-methyl-5-isoxazolyl)pentyl]oxy}benzamide [XXXVII; Y=(CH$_2$)$_5$, m=0, R'=CH$_3$, R$_1'$ and R$_2'$=F, R$_4'$, R$_5'$ and R$_6'$=H, Hal=Cl].

(c) 5-{5-[4-(4,5-Dihydro-2-oxazolyl)-2,6-difluorophenoxy]pentyl}-3-methylisoxazole [IX; Y=(CH$_2$)$_5$, R$_1$ and R$_2$=F, R=CH$_3$, R$_3$, R$_4$, R$_5$ and R$_6$=H, oxazole at 4-position], colorless solid, m.p. 49°–50° C.

EXAMPLE 160

5-{5-[3-Chloro-4-(4,5-dihydro-2-oxazolyl)-2,6-dimethylphenoxyl]pentyl}-3-methylisoxazole, m.p. 49°–50°

C., colorless powder from triethylamine, was obtained as a byproduct in the preparation of 5-{5-[4-(4,5-dihydro-2-oxazolyl)-2,6-dimethylphenoxy]pentyl}-3-methylisoxazole.

EXAMPLE 161

(a) 2,3,5,6-Tetrafluoro-4-{[5-(3-methyl-5-isoxazolyl)pentyl]oxy}benzoic acid, colorless powder, m.p. 123°–125° C., was prepared by hydrolysis of the corresponding methyl ester, in turn prepared by reacting methyl 4-hydroxy-2,3,5,6-tetrafluorobenzoate with 5-(5-bromopentyl)-3-methylisoxazole.

(b) N-(2-Chloroethyl-2,3,5,6-tetrafluoro-4-{[5-(3-methyl-5-isoxazolyl)pentyl]oxy}benzamide (c) 5-{5-[4-(4,5-Dihydro-2-oxazolyl)-2,3,5,6-tetrafluorophenoxy]pentyl}-3-methylisoxazole, m.p. 43°–45° C. (colorless crystals from methylene dichloride/ether/hexane).

EXAMPLE 162

(a) Methyl 3,5-dichloro-4-{[5-(3-methyl-5-isoxazolyl)pentyl]oxy}benzoate [XXXIX; $Y=(CH_2)_5$, $R_1'$ and $R_2'=Cl$, $Alk=CH_3$], pale yellow oil by chromatography.

(b) 3,5-Dichloro-4-{[5-(3-methyl-5-isoxazolyl)pentyl]oxy}benzoic acid [XL; $Y=(CH_2)_5$, $R_1'$ and $R_2'=Cl$], m.p. 77°–79° C.

(c) 3,5-Dichloro-N-(2-chloroethyl)-4-{[5-(3-methyl-5-isoxazolyl)pentyl]oxy}benzamide [XXXVII; $Y=(CH_2)_5$, $m=0$, $R'=CH_3$, $R_1'$ and $R_2'=Cl$, $R_4'$, $R_5'$ and $R_6'=H$, $Hal'=Cl$], m.p. 88°–90° C.

(d) 5-{5-[2,6-Dichloro-4-(4,5-dihydro-2-oxazolyl)phenoxy]pentyl}-3-methylisoxazole [IX; $Y=(CH_2)_5$, $R_1=2$-Cl, $R_2=6$-Cl, $R=CH_3$, $R_3$, $R_4$, $R_5$ and $R_6=H$, oxazole at 4-position]

To a solution of 1.0 g 3,5-dichloro-N-(2-chloroethyl)-4-{[5-(3-methyl-5-isoxazolyl)pentyl]oxy}benzamide in 75 ml methylene dichloride was added 0.92 g 1,8-diazabicyclo[5.4.0]undec-7-ene, and the mixture was heated at reflux for about 16 hrs. The reaction mixture was concentrated in vacuo and the residue partitioned between 150 ml ethyl acetate and 50 ml water. The organic layer was separated, washed with water and saturated sodium chloride solution, dried over anhydrous magnesium sulfate and concentrated in vacuo. The residue was chromatographed on silica gel and eluted with 1:1 ethyl acetate:hexane. The eluted material was isolated, dissolved in ether and crystallized upon seeding to give 0.60 g (66%) of 5-{5-[2,6-dichloro-4-(4,5-dihydro-2-oxazolyl)phenoxy]pentyl}-3-methylisoxazole, light yellow solid, m.p. 39°–40° C., identical with the compound of Example 105, as confirmed by thin layer chromatography.

EXAMPLE 163

(a) Ethyl 3,5-dichloro-4-[6-(3-methyl-5-isoxazolyl)hexyl]benzoate

To a solution of 1.2 ml hexamethylphosphoramide and 6.7 ml 1.75M lithium diisopropylamide in 9 ml tetrahydrofuran at 0° C. under nitrogen was slowly added a solution of 1.00 g 3,5-dichloro-4-methylbenzoic acid in 3 ml tetrahydrofuran. After 1 hr the solution was cooled to −78° C. and 1.00 g 5-(5-bromopentyl)-3-methylisoxazole was added. The reaction mixture was stirred at room temperature for 19 hrs and worked up by acid-base extraction to give 1.3 g crude acid product. The latter was treated with 1 ml ethyl iodide and 4.9 g potassium carbonate in 10 ml dimethylformamide, stirred 12 hrs at room temperature. Extraction with ether and washing with water provided 1 g of ethyl 3,5-dichloro-4-[6-(3-methyl-5-isoxazolyl)hexyl]benzoate suitable for subsequent reactions.

(b) 5-{6-[2,6-Dichloro-4-(4,5-dihydro-2-oxazolyl)phenyl]hexyl}-3-methylisoxazole [II; $n=6$, $R=CH_3$, $R_1=2$-Cl, $R_2=6$-Cl, $R_3$, $R_4$, $R_5$ and $R_6=H$, oxazole at 4-position]

A solution of 2.6 g ethyl 3,5-dichloro-4-[6-(3-methyl-5-isoxazolyl)hexyl]benzoate and 0.21 g lithium hydroxide in 30 ml methanol and 10 ml water was heated at reflux for 12 hrs. Work-up provided 2.2 g of the corresponding benzoic acid which was stirred with 2 ml thionyl chloride in chloroform for 14 hrs. The mixture was concentrated and added to a solution of 1.00 g ethanolamine in 50 ml of methylene dichloride. Flash filtration provided the 2-hydroxyethylamide (1.7 g) as a yellow solid. The latter was converted to its methanesulfonate ester with 0.33 ml methanesulfonyl chloride and 0.7 ml triethylamine in methylene dichloride, and said mesylate was dissolved in 100 ml acetonitrile containing 1.0 g 1,8-diazabicyclo[5.4.0]undec-7-ene and heated at reflux for 4 hrs. Concentration and flash filtration provided 1.0 g 5-{6-[2,6-dichloro-4-(4,5-dihydro-2-oxazolyl)phenyl]hexyl}-3-methylisoxazole, colorless solid, m.p. 65°–66° C. when recrystallized from isopropyl acetate-hexane.

Alternatively, the 2-hydroxyethylamide intermediate was treated with thionyl chloride to form N-(2-chloroethyl)-3,5-dichloro-4-[6-(3-methyl-5-isoxazolyl)hexyl]benzamide, and the latter then cyclized to the final product.

Biological evaluation of compounds of Formulas I and III has shown that they possess antiviral activity. They are useful in inhibiting virus replication in vitro and are primarily active against picornaviruses, including enteroviruses, polioviruses, echovirus and coxsackie virus, and especially numerous strains of rhinoviruses. The in vitro testing of the compounds of the invention against picornaviruses showed that viral replication was inhibited at minimum inhibitory concentrations (MIC) ranging from about 0.003 to about 5 micrograms per milliliter.

The MIC values were determined by a standard plaque reduction assay as follows: HeLa (Ohio) cells in monolayers were infected at a concentration of virus to give approximately 80 plaques per monolayer in the virus control (no drug present). The compound to be tested was serially diluted and included in the agar medium overlay and in some cases, during the adsorption period as well. The MIC was determined to be that concentration of compound which reduced the number of plaques by 50% with respect to the untreated virus control.

In the standard test procedure, the compounds were tested against a panel of fifteen human rhinovirus (HRV) serotypes, namely HRV-2, -1A, -1B, -6, -14, -21, -22, -15, -25, -30, -50, -67, -89, -86 and -41. The MIC value for each rhinovirus serotype was determined, and the efficacy of each compound was determined in terms of $MIC_{50}$ and $MIC_{80}$ values, which is the concentration of the compound required to inhibit 50% and 80%, respectively, of the tested serotypes.

In the in vivo studies, white Swiss mice averaging 20 g in weight were infected with 2 $LD_{50}$'s of poliovirus, type 2, MEF strain, by injecting 0.03 ml of the virus (540 pfu) into the left cerebral hemisphere. The mice were medicated intragastrically with the test compound as a suspension in gum tragacanth one hour prior to infection, 6 hrs post-infection and then b.i.d. for a total of 10 days. Appropriate placebo-medicated mice were included in the test, and all mice were checked twice daily for deaths. The test was terminated at 14 days post-infection.

The blood plasma concentrations of the compounds of the invention were measured in beagle dogs by the following procedure: Animals ranging in weight from 8.5 to 11.5 kg were fasted overnight prior to oral administration of 25 mg/kg of the test compound dissolved in corn oil (125 mg/ml) and contained in gelatin capsules. Blood samples were collected at selected time intervals up to six hours post-medication and analyzed by standard chromatographic procedures to determine the mean maximum concentration of the test compound in micrograms per milliliter [Mean $C_{max}$, µg/ml].

The following Tables give the testing results with the compounds of the invention. In Table I, for some of the compounds, the $MIC_{50}$ and $MIC_{80}$ values are based on the testing of fewer than 15 rhinovirus serotypes. In these cases the number of serotypes (N) is indicated in parentheses after the $MIC_{80}$ figure.

TABLE I

| | In vitro Activity A. Final Products | | | Plasma Concentration (Dog) |
|---|---|---|---|---|
| Example No. | Polio 2 MIC (µg/ml) | Rhinovirus $MIC_{50}$ | $MIC_{80}$ (N) | Mean $C_{Max}$ µg/ml |
| 1(c) | 0.04 | 1.7 | 99(a) | |
| 2 | 0.6 | 0.38 | 2.2 | |
| 3 | 1.2 | 0.07 | 1.6 | |
| 4 | NT | 0.025 | 0.03 (2) | |
| 5 | IA | 1.3 | 99(a) | |
| 6(g) | 0.09 | | 0.06(b) | |
| 7(k) | 0.0012 | 1.3 | 74.6 (4) | |
| 11 | 0.02 | | 0.3(b) | |
| 12 | 0.08 | | 1.4(b) | |
| 13(c) | 0.17 | 0.34 | 1.06 | |
| 14(b) | 0.017 | 0.8 | 25.46 (6) | |
| 15(b) | 0.12 | 0.08 | 0.35 | |
| 16 | 0.13 | 0.08 | 0.43 | |
| 17(b) | IA | 0.89 | 25.99 (6) | |
| 18(b) | NT | 1.75 | 2.1 (2) | |
| 19(b) | 0.3 | 0.8 | 99(a) (7) | |
| 20 | 0.1 | 0.38 | 26.85 (6) | |
| 21(b) | 0.5(c) | | 0.5(b)(c) | |
| 22 | 1.1 | | 0.4(b) | |
| 23 | IA | 1.55 | 2.9 (2) | |
| 24 | 1.7 | 0.087 | 1.2 | |
| 25 | IA | | 2.1(b) | |
| 26(b) | NT | 0.94 | 1.12 (2) | |
| 27(b) | IA | 0.405 | 25.8 (6) | |
| 28 | 0.007(c) | | 0.1(b)(c) | |
| 29(b) | 0.02 | 1.245 | 1.7 (2) | |
| 30 | >0.2(c) | | 0.08(b)(c) | |
| 31(b) | 0.36 | 0.15 | 0.56 | |
| 32 | 1.3 | 0.09 | 0.27 | |
| 33 | 3 | 51 | 99(a) (6) | |
| 34(b) | 0.49 | 0.2 | 26.47 (6) | |
| 35 | 0.05 | 1.385 | 1.8 (2) | |
| 37 | 0.4 | | 0.12(b) | |
| 38(b) | 0.3 | 0.69 | 0.9 (2) | |
| 39 | IA | 0.87 | 99(a) (6) | |
| 40 | IA | 0.535 | 99(a) (6) | |
| 41(b) | 1.0 | 0.55 | 4 (7) | |
| 42 | 0.12 | 0.35 | 0.64 | |
| 43 | 0.3 | 0.31 | 1.0 | |
| 44 | 0.3 | 0.08 | 0.54 | |
| 45 | 0.5 | 0.16 | 0.7 | |
| 46 | 0.1 | 0.09 | 0.2 | |
| 47 | 0.02 | 0.36 | 2.4 | |
| 48 | 2.3 | 0.13 | 0.37 | |
| 49 | 2.0 | 1.1 | 4.6 | |
| 50 | 0.7 | 5.05 | 99(a) (6) | |
| 51 | 0.045 | 0.56 | 1.6 | |
| 52 | 0.003 | 0.084 | 1.9 | |
| 53 | 0.08 | 0.087 | 0.64 | |
| 54 | 1.3 | 0.08 | 0.42 | |
| 55 | NT | 49.64 | 99(a) (2) | |
| 56 | 0.07 | 0.164 | 25.27 (6) | |
| 57 | IA | 50.1 | 99(a) (6) | |
| 58 | 3.1 | 0.15 | 0.43 | 4.26 ± 0.47 |
| 59 | 0.04 | 0.435 | 25.22 (6) | |
| 60 | 0.24 | 0.1 | 0.7 | |
| 61 | 0.54 | 0.39 | 0.75 | |
| 62 | 0.51 | 1.5 | 2.4 | |
| 63 | 2.3 | 0.55 | 1.05 | |
| 64 | 2.4 | 0.485 | 25.59 (6) | |
| 65 | IA | 0.26 | 0.45 | |
| 66 | IA | 0.78 | 99(a) | |
| 67 | IA | | 2.6(b) | |
| 68 | 0.23 | 0.4 | 1.0 | |
| 69 | 0.44 | | 0.5(b) | |
| 70 | 0.1 | 0.85 | 1.6 (12) | |
| 71 | IA | | 0.075(b) | |
| 72 | IA | 0.27 | 0.69 | |
| 73 | 0.46 | | NT | |
| 74 | 2.0 | 0.13 | 0.59 | |
| 75 | 0.69 | 9.95 | 35.25 (6) | |
| 76 | IA | 50.14 | 99(a) (2) | |
| 77 | 0.05 | 0.088 | 1.47 | |
| 78 | IA | | 3.1(b) | |
| 79 | 2.3 | 0.3 | 0.7 | |
| 80 | 0.11 | 0.13 | 0.27 | |
| 81 | IA | | 2.1(b) | |
| 82 | 2.9 | 1.2 | 5.4 | |
| 83 | 5.0 | 3.75 | 99(a) (6) | |
| 84 | 0.11 | 0.082 | 0.72 | |
| 85 | IA | | 2.46(b) | |
| 86 | 2.6 | 99 | 99(a) (6) | |
| 87(b) | 0.04 | | 0.4(b) | |
| 88 | 0.025 | 0.38 | 25.2 (6) | |
| 89 (d) | 0.16 | 0.19 | 0.77 | |
| 90 | 1.5 | 0.2 | 0.49 | |
| 91 | IA | 0.75 | 1.4 | |
| 92 | 0.07 | 0.07 | 0.61 | |
| 93(f) | 0.09 | 0.09 | 1.3 | |
| 94(c) | 0.8 | 1.06 | 99(a) (6) | |
| 95 | 0.15 | 1.65 | 26.3 (6) | |
| 96(b) | 0.095 | 1.4 | 2.5 | |
| 97(b) | 5.4 | 0.135 | 0.76 | |
| 98 | 12.5 | 0.21 | 2.8 | |
| 99 | 0.27 | 1.3 | 2.3 (2) | |
| 100 | 6.2 | 0.76 | 99(a) | |
| 101(b) | 0.65 | | 1.9(b) | |
| 102 | 12.5 | 12.5 | 99(a) (6) | |
| 103(c) | 0.37 | 0.57 | 27.1 (6) | |
| 104 | 12.5 | 9.85 | 12.5 (2) | |
| 105(c) | 0.59 | 0.07 | 0.126 | 1.57 ± 0.35 |
| 106 | 0.58 | 0.18 | 0.41 | 1.53 ± 0.15 |
| 107 | 4.6 | 0.12 | 0.37 | 1.53 ± 0.14 |
| 108 | 2.6 | 0.13 | 0.34 | |
| 109 | 2.9 | 0.16 | 0.89 | 2.11 ± 0.61 |
| 110 | IA | 0.24 | 0.64 | |
| 112 | IA | 0.079 | 0.74 | |
| 113 | 0.4 | 0.09 | 0.167 | |
| 114 | 0.48 | 0.22 | 0.62 | |
| 115 | 3.1 | 0.04 | 0.58 | |
| 116 | 3.1 | 0.13 | 0.5 | |
| 117 | 0.39 | 0.09 | 0.31 | |
| 118(c) | IA | 0.37 | 0.84 | |
| 119(c) | NT | 0.32 | 0.53 | 2.13 ± 0.48 |
| 120 | IA | 0.16 | 0.67 | |
| 121 | NT | 0.09 | 26.0 (6) | |
| 122 | NT | 0.24 | 50.3 (5) | |
| 123 | 1.01 | | 0.4(b) | |
| 124 | NT | 0.36 | 2.4 | |
| 125 | NT | 0.69 | 2.3 | |
| 126 | IA | 1.23 | 26.2 (6) | |
| 127 | IA | 0.76 | 1.4 (2) | |
| 128 | IA | 0.245 | 27.1 (6) | |

TABLE I-continued

In vitro Activity
A. Final Products

| Example No. | Polio 2 MIC (µg/ml) | Rhinovirus MIC$_{50}$ | Rhinovirus MIC$_{80}$ (N) | Plasma Concentration (Dog) Mean C$_{Max}$ µg/ml |
|---|---|---|---|---|
| 129 | IA | 1.33 | 2.6 (2) | |
| 130 | NT | 1.08 | 2.07 (2) | |
| 131 | NT | 1.44 | 2.38 (2) | |
| 132 | NT | 1.025 | 1.9 (2) | |
| 133 | 0.09 | 0.16 | 0.68 | |
| 134 | 1.9 | 0.29 | 0.5 | |
| 135 | 2.6 | 0.335 | 0.6 (2) | |
| 136(b) | 0.62 | 0.88 | 1.47 (2) | |
| 137 | 2.0 | 3.255 | 6.2 (2) | |
| 138 | NT | 0.2 | 1.2 (4) | |
| 139 | NT | 0.795 | 25.9 (6) | |
| 140 | NT | 0.49 | 26.9 (6) | |
| 141 | 0.23 | 0.25 | 0.54 | |
| 142 | 0.37 | 0.26 | 6.2 (7) | |
| 143 | 0.3 | 0.31 | 1.0 | |
| 144 | 12.5 | 0.14 | 1.1 | |
| 145 | 0.033 | 0.2 | 0.29 | |
| 146 | 4.2 | 0.29 | 0.55 | |
| 147 | 0.4 | 0.23 | 0.76 | |
| 148 | 8.5 | 0.17 | 0.45 | |
| 149(b) | IA | 0.13 | 1.1 | |
| 150(b) | NT | 0.12 | 0.35 | |
| 151 | 0.4 | 0.2 | 1.2 | |
| 152(d) | 0.97 | 0.095 | 0.23 | |
| 153(d) | 0.4 | 0.09 | 0.18 | |
| 154(c) | 0.8 | 0.22 | 0.33 | |
| 155(c) | IA | 0.11 | 0.56 | |
| 156(b) | IA | 0.705 | 28.6 (6) | |
| 157(d) | 3.3 | 1.25 | 2.5 | |
| 158(d) | 1.0 | 2.1 | 5.0 | |
| 159(c) | 0.12 | 0.15 | 0.66 | |
| 160 | IA | 0.24 | 0.4 | |
| 161(c) | 0.05 | 0.25 | 3.5 | |
| 163(b) | 1.4 | 0.49 | 0.73 | |

(a) Inactive against more than 20% of the serotypes tested
(b) Against HRV-2 only
(c) Compound present during adsorption and in the overlay media
NT = Not tested
IA = Inactive A particularly preferred species, the compound of Example 105(c), namely, 5-{5-[2,6-dichloro-4-(4,5-dihydro-2-oxazolyl)phenoxy]pentyl}-3-methylisoxazole, has been tested against 53 rhinovirus serotypes and found to have an MIC$_{80}$ value of 0.23 µg/ml.

B. Intermediates of Formula XXXVII

| Example No. | Polio 2 MIC (µg/ml) | Rhinovirus MIC$_{50}$ | Rhinovirus MIC$_{80}$ (N) |
|---|---|---|---|
| 152(c) | 2.1 | 0.14 | 0.6 |
| 153(c) | 0.86 | 0.08 | 0.23 |
| 154(b) | 1.13 | 0.17 | 0.63 |
| 156(a) | IA | 0.795 | 99(a) (6) |
| 157(c) | 2.1 | 0.49 | 1.2 |
| 158(b) | 2.0 | 1.73 | 4.7 |
| 162(c) | 0.48 | 0.16 | 0.28 |

IA = Inactive
(a) Inactive against more than 20% of the serotypes tested

TABLE II

In vivo vs Poliovirus-2

| Example No. | Survivors Day 14 Post Infection |
|---|---|
| 1(c) | 50 mg/kg/day - 14/20 |
| | 100 mg/kg/day - 18/20 |
| | placebo - 1/20 |
| 2 | 77 mg/kg/day - 17/20 |
| | placebo - 6/20 |
| 3 | 100 mg/kg/day - 9/20 |
| | 200 mg/kg/day - 12/20 |

TABLE II-continued

In vivo vs Poliovirus-2

| Example No. | Survivors Day 14 Post Infection |
|---|---|
| | 400 mg/kg/day - 14/20 |
| | placebo - 6/20 |
| 6(g) | 50 mg/kg/day - 5/20 |
| | 100 mg/kg/day - 17/20 |
| | 200 mg/kg/day - 19/20 |
| | placebo - 1/20 |
| 7(k) | 100 mg/kg/day - 16/20 |
| | placebo - 6/20 |
| 13(c) | 25 mg/kg/day - 4/20 |
| | 50 mg/kg/day - 11/18 |
| | 100 mg/kg/day - 16/20 |
| | placebo - 2/18 |
| 15(b) | 50 mg/kg/day - 8/20 |
| | 100 mg/kg/day - 12/20 |
| | placebo - 5/20 |
| 105(c) | 50 mg/kg/day - 2/20 |
| | 100 mg/kg/day - 5/20 |
| | 200 mg/kg/day - 6/20 |
| | placebo - 1/20 |

The compound of Example 105(c), namely, 5-{5-[2,6-dichloro-4-(4,5-dihydro-2-oxazolyl)phenoxy]pentyl}-3-methylisoxazole, was also found to be active against 27 enteroviruses (MIC$_{80}$=1.6 µg/ml). In vivo efficacy studies in mouse infection models showed that this compound had potent oral activity in echovirus-9 and coxsackie virus A-9 infections; the PD$_{50}$ in coxsackie-A-9 infected mice was 2.5 mg/kg, and the compound was effective against echovirus-9 induced paralysis in mice with twice a day dosing with 12.5 mg/kg.

The compounds of Examples 13(c), 17(b) and 19(b) were also found to possess in vitro activity against herpes virus type 2 at concentrations of 1.6, 0.4 and 3.1 µg/ml, respectively.

The antiviral compositions are formulated for use by preparing a dilute solution or suspension in a pharmaceutically acceptable aqueous, organic or aqueous-organic medium for topical and parenteral administration by intravenous or intramuscular injection, or for intranasal or ophthalmic application; or are prepared in tablet, capsule, or aqueous suspension form with conventional excipients for oral administration.

I claim:

1. A compound of the formula

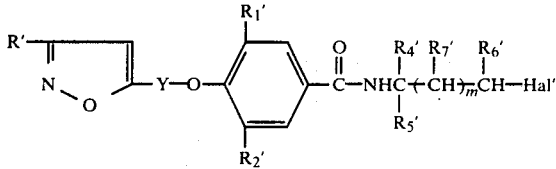

wherein:
Y is an alkylene bridge of 3-9 carbon atoms;
m is 0 or 1;
R$_1'$ and R$_2'$ are selected from the group consisting of hydrogen, lower-alkyl, halogen, nitro, loweralkoxy, lower-alkoxycarbonyl and trifluoromethyl;
R', R$_4'$, R$_5'$, R$_6'$ and R$_7'$ are hydrogen or alkyl of 1-5 carbon atoms; R' being other than hydrogen; and
Hal is chlorine or bromine.

2. 3,5-Dichloro-N-(2-chloroethyl-4-{[5-(3-methyl-5-isoxazolyl)pentyl]oxy}benzamide, according to claim 1.

3. A composition for combating picornaviruses which comprises an antivirally effective amount of a compound according to claim 1 in admixture with a suitable carrier or diluent.

4. A composition according to claim 3 for combating rhinoviruses.

5. A method for combating picornaviruses which comprises contacting the locus of said viruses with a composition according to claim 3.

6. A method according to claim 5 for combating rhinoviruses.

7. A method for combating a picornaviral infection in a mammalian host which comprises administering to said host an antivirally effective amount of a compound according to claim 1.

* * * * *

UNITED STATES PATENT AND TRADEMARK OFFICE
CERTIFICATE OF CORRECTION

PATENT NO. : 5,002,960
DATED : March 26, 1991
INVENTOR(S) : Guy D. Diana

It is certified that error appears in the above-identified patent and that said Letters Patent is hereby corrected as shown below:

Column 13, formula XXXVII,

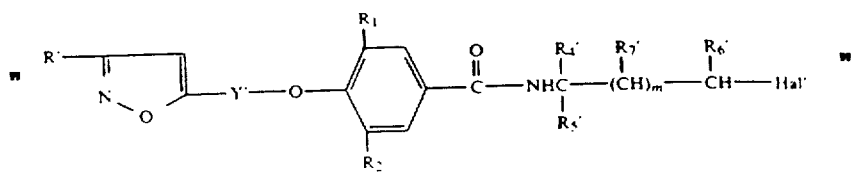

should read --  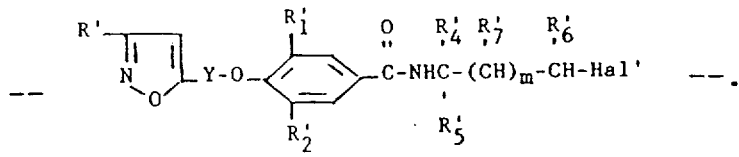  --.

UNITED STATES PATENT AND TRADEMARK OFFICE
CERTIFICATE OF CORRECTION

PATENT NO. : 5,002,960
DATED : March 26, 1991
INVENTOR(S) : Guy D. Diana

It is certified that error appears in the above-identified patent and that said Letters Patent is hereby corrected as shown below:

Column 14, lines 10-16,

" ↓ " should read -- ↓ --.

XLII            XXXVI

Signed and Sealed this

Twentieth Day of July, 1993

Attest:

MICHAEL K. KIRK

Attesting Officer     Acting Commissioner of Patents and Trademarks